US007375086B2

(12) United States Patent
Nuñez et al.

(10) Patent No.: US 7,375,086 B2
(45) Date of Patent: May 20, 2008

(54) MODULATORS OF NOD2 SIGNALING

(75) Inventors: Gabriel Nuñez, Ann Arbor, MI (US);
Naohiro Inohara, Ann Arbor, MI (US);
Yasunori Ogura, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 47 days.

(21) Appl. No.: 11/331,240

(22) Filed: Jan. 12, 2006

(65) Prior Publication Data
US 2006/0160118 A1 Jul. 20, 2006

Related U.S. Application Data

(60) Division of application No. 10/314,506, filed on Dec. 9, 2002, now Pat. No. 7,060,442, which is a continuation-in-part of application No. 10/014,269, filed on Oct. 26, 2001, now Pat. No. 6,835,815.

(60) Provisional application No. 60/244,289, filed on Oct. 30, 2000.

(51) Int. Cl.
A61K 38/00 (2006.01)
A61K 39/02 (2006.01)
C07K 5/00 (2006.01)

(52) U.S. Cl. .................... 514/19; 514/8; 530/300; 424/185.1; 424/190.1

(58) Field of Classification Search .................. None
See application file for complete search history.

(56) References Cited

U.S. PATENT DOCUMENTS

| 4,496,778 | A | 1/1985 | Myers et al. ............... 568/860 |
|---|---|---|---|
| 4,650,764 | A | 3/1987 | Temin et al. ............... 435/240 |
| 4,657,760 | A | 4/1987 | Kung et al. ................. 424/85 |
| 4,683,195 | A | 7/1987 | Mullis et al. ................. 435/6 |
| 4,683,202 | A | 7/1987 | Mullis .......................... 435/91 |
| 4,797,368 | A | 1/1989 | Carter et al. ............... 435/320 |
| 4,861,719 | A | 8/1989 | Miller ......................... 435/236 |
| 4,873,191 | A | 10/1989 | Wagner et al. ........... 435/172.3 |
| 4,940,838 | A | 7/1990 | Schilperoort et al. ....... 800/205 |
| 4,946,787 | A | 8/1990 | Eppstein et al. ......... 435/240.2 |
| 4,965,188 | A | 10/1990 | Mullis et al. .................. 435/6 |
| 4,980,289 | A | 12/1990 | Temin et al. ............... 435/235 |
| 5,096,815 | A | 3/1992 | Ladner et al. ............. 435/69.1 |
| 5,124,263 | A | 6/1992 | Temin et al. ............. 435/240.2 |
| 5,139,941 | A | 8/1992 | Myzyczka et al. ........ 435/172.3 |
| 5,173,410 | A | 12/1992 | Ahlquist ..................... 435/91 |
| 5,198,346 | A | 3/1993 | Ladner et al. ............. 435/69.1 |
| 5,206,344 | A | 4/1993 | Katre et al. ................. 530/351 |
| 5,223,409 | A | 6/1993 | Ladner et al. ............. 435/69.7 |
| 5,225,212 | A | 7/1993 | Martin et al. ............... 424/450 |
| 5,399,346 | A | 3/1995 | Anderson et al. ......... 424/93.21 |
| 5,459,127 | A | 10/1995 | Felgner et al. ................ 514/7 |
| 5,474,796 | A | 12/1995 | Brennan ..................... 427/2.13 |
| 5,500,360 | A | 3/1996 | Ahlquist et al. ......... 435/172.3 |
| 5,501,967 | A | 3/1996 | Offringa et al. ......... 435/172.3 |
| 5,538,848 | A | 7/1996 | Livak et al. .................... 435/5 |
| 5,580,859 | A | 12/1996 | Felgner et al. ................ 514/44 |
| 5,584,807 | A | 12/1996 | McCabe ....................... 604/71 |
| 5,589,466 | A | 12/1996 | Felgner et al. ................ 514/44 |
| 5,589,616 | A | 12/1996 | Hoffman ..................... 800/205 |
| 5,605,798 | A | 2/1997 | Koster ........................... 435/6 |
| 5,608,153 | A | 3/1997 | Ueyanagi ......................... 73/1 |
| 5,614,396 | A | 3/1997 | Bradley et al. ........... 435/172.3 |
| 5,618,682 | A | 4/1997 | Scheirer ......................... 435/8 |
| 5,674,713 | A | 10/1997 | McElroy et al. ........... 435/69.7 |
| 5,733,731 | A | 3/1998 | Schatz et al. .................. 436/6 |
| 5,777,324 | A | 7/1998 | Hillenkamp ................ 250/288 |
| 5,811,238 | A | 9/1998 | Stemmer et al. .............. 435/6 |
| 5,824,877 | A | 10/1998 | Hinchee et al. ............ 800/205 |
| 5,830,721 | A | 11/1998 | Stemmer et al. ......... 435/172.1 |
| 5,837,458 | A | 11/1998 | Minshull et al. ............... 435/6 |
| 5,843,654 | A | 12/1998 | Heisler et al. ................. 435/6 |
| 5,843,669 | A | 12/1998 | Kaiser et al. .................. 435/6 |
| 5,846,717 | A | 12/1998 | Brow et al. .................... 435/6 |
| 5,846,795 | A | 12/1998 | Ahlquist et al. ......... 435/172.3 |
| 5,858,659 | A | 1/1999 | Sapolsky et al. .............. 435/6 |
| 5,866,785 | A | 2/1999 | Donson et al. ............. 800/205 |
| 5,888,780 | A | 3/1999 | Dahlberg et al. ......... 435/91.53 |
| 5,891,840 | A | 4/1999 | Cady et al. .................... 514/2 |
| 5,919,626 | A | 7/1999 | Shi et al. ........................ 435/6 |

(Continued)

FOREIGN PATENT DOCUMENTS

| EP | 0 025 949 | 9/1980 |
|---|---|---|
| EP | 078 220 | 10/1985 |
| EP | 0 185 573 | 11/1985 |

(Continued)

OTHER PUBLICATIONS

Chou et al., Cell, 94:171 [1991].
Takeuchi et al., Immunity, 4:443 [1999].
Bertin et al., J. Biol. Chem. 274:12955-12958 [1999].
Li et al., Cell 91:479-489 [1997].
Zou et al., J. Biol. Chem. 274:11549-11556 [1999].
Snivasula et al., Mol. Cell 1:949-957 [1998].
Hu et al., J. Bio. Chem. 273: 33489-34494 [1998].
Inohara et al., J. Biol. Chem. 273:12296-12300 [1998].
McCarthy et al., J. Bio. Chem. 273:16968-16975 [1998].
Thome et al., Curr. Biol. 8:885-888 [1998].
Inohara et al., J. Biol. Chem. 275:27823-27831 [2000].
Parniske et al., Cell 91:821-832 [1997].
Yang et al., Nature, 395:284-288 [1998].

(Continued)

Primary Examiner—Robert Mondesi
Assistant Examiner—Anand Desai
(74) Attorney, Agent, or Firm—Casimir Jones, S.C.

(57) ABSTRACT

The present invention relates to intracellular signaling molecules, in particular the Nod2 protein and nucleic acids encoding the Nod2 protein. The present invention provides methods of identifying modulators of Nod2 signaling. In particular, the present invention additionally provides methods of screening immune modulators such as adjuvants using Nod2. The present invention further provides methods of altering Nod2 signaling.

3 Claims, 36 Drawing Sheets

U.S. PATENT DOCUMENTS

| | | | | |
|---|---|---|---|---|
| 5,925,525 | A | 7/1999 | Fodor et al. | 435/6 |
| 5,952,174 | A | 9/1999 | Nikiforov et al. | 435/6 |
| 5,965,794 | A | 10/1999 | Turpen | 800/288 |
| 5,976,796 | A | 11/1999 | Szalay et al. | 435/6 |
| 5,977,438 | A | 11/1999 | Turpen et al. | 800/288 |
| 5,981,839 | A | 11/1999 | Knauf et al. | 800/287 |
| 5,985,551 | A | 11/1999 | Brennan | 435/6 |
| 5,985,557 | A | 11/1999 | Prudent et al. | 435/6 |
| 5,994,069 | A | 11/1999 | Hall et al. | 435/6 |
| 6,001,311 | A | 12/1999 | Brennan | 422/131 |
| 6,001,567 | A | 12/1999 | Brow et al. | 435/6 |
| 6,017,696 | A | 1/2000 | Heller | 435/6 |
| 6,043,031 | A | 3/2000 | Koster et al. | 435/6 |
| 6,045,996 | A | 4/2000 | Cronin et al. | 435/6 |
| 6,051,380 | A | 4/2000 | Sosnowski et al. | 435/6 |
| 6,051,757 | A | 4/2000 | Barton et al. | 800/294 |
| 6,063,947 | A | 5/2000 | DeBonte et al. | 554/223 |
| 6,068,818 | A | 5/2000 | Ackley et al. | 422/50 |
| 6,074,859 | A | 6/2000 | Hirokawa et al. | 435/189 |
| 6,080,912 | A | 6/2000 | Bremel et al. | 800/23 |
| 6,090,543 | A | 7/2000 | Prudent et al. | 435/6 |

FOREIGN PATENT DOCUMENTS

| | | |
|---|---|---|
| EP | 0 453 242 | 4/1991 |
| EP | 0 488 528 A1 | 10/1991 |
| WO | WO 93/03367 | 2/1983 |
| WO | WO 84/03564 | 9/1984 |
| WO | WO 90/08832 | 8/1990 |
| WO | WO 91/18088 | 11/1991 |
| WO | WO 92/05263 | 4/1992 |
| WO | WO 94/12649 | 6/1994 |
| WO | WO 94/21807 | 9/1994 |
| WO | WO 94/26914 | 11/1994 |
| WO | WO 94/28152 | 12/1994 |
| WO | WO 94/28938 | 12/1994 |
| WO | WO 95/02697 | 1/1995 |
| WO | WO 95/21931 | 8/1995 |
| WO | WO 96/25508 | 8/1996 |
| WO | WO 99/67641 | 12/1999 |
| WO | WO 00/39587 | 7/2000 |

OTHER PUBLICATIONS

Aliprantis et al., Science, 285:736-739 [1999].
Poltorak et al., Science, 282:2085-2088 [1998].
Zou et al., Cell, 90:405-413 [1997].
Inohara et al., J. Biol. Chem., 274:14560-14568 [1999].
Shimada et al., Int. Immunol., 11:1357-1362 [1999].
Huang et al., PNAS, 94:12829-12832 [1997].
Medzhitov et al., Mol. Cell, 2:253-258 [1998].
Hsu et al., Immunity, 4:387-396 [1996].
Yamaoka et al., Cell 93: 1231-1240 [1998].
Kobe and Deisenhofer, Curr. Opin. Struct. Biol. 5: 409-416 [1995].
Hu et al., EMBO J. 18: 3586-3595 [1991].
Karin, J. Biol. Chem. 274: 27339-27342 [1999].
Hofmann et al., Trends Biochem. Sci. 22: 155-156 [1997].
MacCorkle et al., Proc. Nat. Acad. Sci. U. S. A. 95: 3655-3660 [1998].
Schwandner et al., J. Biol. chem., 274:17406-17409 [1999].
Aderem and Ulevitch, Nature, 406:782-787 [2000].
Philpott et al., J. Immunol., 165:903-914 [2000].
Chow et al., J. Biol. Chem., 274:10689-10692 [1999].
Anderson and Young, Quantitative Filter Hybridization, in Nucleic Acid Hybridization [1985].
Smith and Waterman, Adv. Appl. Math. 2: 482 [1981].
Needleman and Wunsch, J. Mol. Biol. 48:443 [1970].
Pearson and Lipman, Proc., Natl. Acad. Sci. (U.S.A.) 85:2444 [1988].
Chamberlin et al., Nature 228:227 [1970].
H.A. Erlich (ed.), *PCR Technology*, Stockton Press [1989].
J. Sambrook et al., *Molecular Cloning: A Laboratory Manual*, Cold Spring Harbor Press, NY, pp. 9.31-9.58 [1989].
Graham and van der Eb, Virol., 52;456 [1973].
Neer, 1995. Cell 80:249-257 [1995].
Sternweis and Smrcka, Trends in Biochem. Sci. 17:502-506 [1992.
Carbounneau, H. and Tonks, Annu. Rev. Cell Biol. 8:463-93 [1992].
Saito et al., Cell Growth and Diff. 2:59-65 [1991].
DeWet et al., Mol. Cell. Biol. 7:725 [1987].
Wahl, et al., Meth. Enzymol., 152:399-407 [1987].
Sudarickov et al., Nucleic Acids Res., 16:8187 [(1988].
Parker et al., Nucleic Acids Res., 19:3055-60 [1991].
Stryer ed., *Biochemistry*, p. 17-21, 2nd ed. WH Freeman and Co., [1981].
Murray et al., Nucl. Acids Res., 17 [1989].
Gluzman, Cell 23:175 [1981].
Davis et al., Basic Methods in Molecular Biology, [1986].
Wilson et al., Cell, 37:767 [1984].
Ben-Bassat et al., J. Bacteriol., 169:751-757 [1987].
Miller et al., Proc. Natl. Acad. Sci. USA 84:2718-1722 [1990].
Evans et al., Nature 339:385 [1989].
Huang et al., J. Virol., 62:3855 [1988].
Schlienger et al., J. Virol., 66:2 [1992].
Posnett et al., J. Biol. Chem., 263:1719 [1988].
Nardelli et al., J. Immunol., 148:914 [1992].
Hochuli et al., J. Chromatogr., 411:177 [1987].
Janknecht et al., Proc. Natl. Acad. Sci. USA 88:8972.
Narang, Tetrahedron Lett., 39:3 9 [1983].
Scott et al., Science 249:386-390 [1980].
Roberts et al., Proc. Natl. Acad. Sci. USA 89:2429-2433 [1992].
Cwirla et al., Proc. Natl. Acad. Sci. USA 87: 6378-6382 [1990].
Moore and Arnold, Nat. Biotech., 14, 458-67 [1996].
Leung et al., Technique, 1:11-15 [1989].
Eckert and Kunkel, PCR Methods Appl., 1:17-24 [1991].
Caldwell and Joyce, PCR Methods Appl., 2:28-33 [1992].
Zhao and Arnold, Nuc. Acids. Res., 25:1307-08 [1997].
Stemmer, Nature, 370:398-91 [1994].
Stemmer, Proc. Natl. Acad. Sci. USA, 91:10747-51 [1994].
Crameri et al., Nat. Biotech., 14:315-19 [1996].
Zhang et al., Proc. Natl. Acad. Sci. USA, 94:4504-09 [1997].
Crameri et al., Nat. Biotech., 15:436-38 [1997].
Kühler and Milstein, Nature 256:495-497 [1975].
Kozbor et al., Immunol. Tod., 4:72 [1983].
Cole et al., in *Monoclonal Antibodies and Cancer Therapy*, Alan R. Liss, Inc., pp. 77-96 [1985].
Cote et al., Proc. Natl. Acad. Sci. USA 80:2026-2030 [1983].
Huse et al., Science 246:1275-1281 [1989].
Miller and Rosman, BioTech., 7:980-990 [1992].
Kaplitt et al., Mol. Cell. Neurosci., 2:320-330 [1991].
Stratford-Perricaudet et al., J. Clin. Invest., 90:626-630 [1992].
La Salle et al., Science 259:988-990 [1993].
Samulski et al., J. Virol., 61:3096-3101 [1987].
Samulski et al., J. Virol., 63:3822-3828 [1989].
Lebkowski et al., Mol. Cell. Biol., 8:3988-3996 [1988].
Beard et al., Virol., 75-81 [1990].
Levrero et al., Gene 101:195 [1991].
Graham, EMBO J., 3:2917 [1984].
Graham et al., J. Gen. Virol., 36:59 [1977].
Mann et al., Cell 33:153 [1983].
Markowitz et al., J. Virol., 62:1120 [1988].
McCormick, BioTechnol., 3:689 [1985].
Kuo et al., Blood 82:845 [1993].
Bender et al., J. Virol., 61:1639 [1987].
Felgner et al., Proc. Natl. Acad. Sci. USA 84:7413-7417 [1987].
Machy et al., Proc. Natl. Acad. Sci. USA 85:8027-8031 [1988].
Ulmer et al., Science 259:1745-1748 [1993].
Felgner and Ringold, Science 337:387-388 [1989].
Wilson et al., J. Biol. Chem., 267:963-967 [1992].
Wu and Wu, J. Biol. Chem., 263:14621-14624 [1988].
Williams et al., Proc. Natl. Acad. Sci. USA 88:2726-2730 [1991].
Curiel et al., Hum. Gene Ther., 3:147-154 [1992].
Wu and Wu, J. Biol. Chem., 262:4429-4432 [1987].
Brinster et al., Proc. Natl. Acad. Sci. USA 82:4438-4442 [1985].
Janenich, Proc. Natl. Acad. Sci. USA 73:1260-1264 [1976].

Jahner et al., Proc. Natl. Acad Sci. USA 82:6927-693 [1985].
Stewart et al., EMBO J., 6:383-388 [1987].
Jahner et al., Nature 298:623-628 [1982].
Haskell and Bowen, Mol. Reprod. Dev., 40:386 [1995].
Evans et al., Nature 292:154-156 [1981].
Bradley et al., Nature 309:255-258 [1984].
Gossler et al., Proc. Acad. Sci. USA 83:9065-9069 [1986].
Robertson et al., Nature 322:445-448 [1986].
Jaenisch, Science 240:1468-1474 [1988].
Hooykas-Van Slogteren et al., Nature 311:763-764 [1984].
Klee et al., Ann. Rev. Plant Phys. 38:467-486 [1987].
Sheikoleslam et al., Plant Molec. Biol. 8:291-298 [1987].
Bidney et al., Plant Molec. Biol. 18:301-313 [1992].
Van der Krol et al., Biotechniques 6:958-976 [1988].
Sheehy et al., Proc. Natl. Acad. Sci. USA 85:8805-8809 [1988].
Cannon et al., Plant Mol. Biol. 15:39-47 [1990].
Ch'ng et al., Proc. Natl. Acad. Sci. USA 86:10006-10010 [1989].
Haseloff, et al., Nature 334:585-591 [1988].
Napoli et al., Plant Cell 2:279-289 [1990].
Van der Krol et al., Plant Cell 2:291-299 [1990].
Smith et al., Mol. Gen. Genetics 224:477-481 [1990].
Bolton et al., Gene 67:31 [1988].
Denyer et al., Drug Discov. Today 3:323-32 [1998].
Gonzales et al., Drug. Discov. Today 4:431-39 [1999].
Schroeder and Neagle, J. Biomol. Screening 1:75-80 [1996].
Rietschel et al., Curr Top. Microbiol. Immunol., 216:39-81 [1997].
Wu and R. B. Wallace, Genomics 4:560 [1989].
Dixon et al., Proc. Natl. Acad. Sci. U. S. A. 97:8807-8814 [2000].
Leister and Katagiri, Plant J., 22:345-354 [2000].

Krueger et al., Proc. Natl. Acad. Sci. USA 89:7417-7421 [1992].
Ausabel et al. (eds.), Current Protocols in Molecular Biology, John Wiley & Sons, NY [1991].
Itakura et al., Recombinant DNA, in Walton (ed.), *Proceedings of the 3rd Cleveland Symposium on Macromolecules*, Elsevier, Amsterdam, pp. 273-289 [1991].
Itakura et al., Science 198:1056 [1984].
Ike et al., Nucl. Acid Res., 11:477 [1983].
Devlin et al., Science 249: 404-406 [1990].
Smith, Nature, 370:324-25 [1994].
Caruthers et al., Nucl. Acids Res. Symp. Ser., 7:215-233 [1990].
Crea and Horn, Nucl. Acids Res., 9:2331 [1980].
Matteucci and Caruthers, Tetrahedron Lett., 21:719 [1980].
Chow and Kempe, Nucl. Acids Res., 9:2807-2817 [1981].
Creighton, *Proteins Structures And Molecular Principles*, W H Freeman and Co, New York N.Y. [1983].
Roberge et al., Science 269:202-204 [1995].
Bernstein et al., Genet. Eng., 7:235 [1985].
Hogan et al., in *Manipulating the Mouse Embryo*, Cold Spring Harbor Laboratory Press, Cold Spring Harbor, N.Y. [1986].
Cho et al., Inflammatory Bowl Diseases 3:186 [1997].
Brant et al., Gastroenterology 115:1056 [1998].
Cho et al., Proc. Natl. Acad. Sci. 95:7502 [1998].
Cavanaugh et al., Ann. Hum. Gent. 62:291 [1998].
Hugot et al., Nature 379:821 [1996].
Tysk et al., Gut 29:990 [1988].
Cho et al., Hum. Mol. Gent. 9:1425 [2000].
Itakura et al., Ann. Rev. Biochem. 53:323-356 (1984).

SEQ ID NO:33

Nod2 cDNA sequence

| | | | | | |
|---|---|---|---|---|---|
| gtagacagat | ccaggctcac | cagtcctgtg | ccactgggct | tttggcgttc | tgcacaaggc | 60 |
| ctacccgcag | atgccatgcc | tgctccccca | gcctaatggg | ctttgatggg | ggaagagggt | 120 |
| ggttcagcct | ctcacgatga | ggaggaaaga | gcaagtgtcc | tcctcggaca | ttctccgggt | 180 |
| tgtgaaatgt | gctcgcagga | ggcttttcag | gcacagagga | gccagctggt | cgagctgctg | 240 |
| gtctcagggt | ccctggaagg | cttcgagagt | gtcctggact | ggctgctgtc | ctgggaggtc | 300 |
| ctctcctggg | aggactacga | gggcttccac | ctcctgggcc | agcctctctc | ccacttggcc | 360 |
| aggcgccttc | tggacaccgt | ctggaataag | ggtacttggg | cctgtcagaa | gctcatcgcg | 420 |
| gctgcccaag | aagcccaggc | cgacagccag | tcccccaagc | tgcatggctg | ctgggacccc | 480 |
| cactcgctcc | acccagcccg | agacctgcag | agtcaccggc | cagccattgt | caggaggctc | 540 |
| cacagccatg | tggagaacat | gctggacctg | gcatgggagc | ggggtttcgt | cagccagtat | 600 |
| gaatgtgatg | aaatcaggtt | gccgatcttc | acacgtccc | agagggcaag | aaggctgctt | 660 |
| gatcttgcca | cggtgaaagc | gaatggattg | gctgccttcc | ttctacaaca | tgttcaggaa | 720 |
| ttaccagtcc | cattggccct | gcctttggaa | gctgccacat | gcaagaagta | tatggccaag | 780 |
| ctgaggacca | cggtgtctgc | tcagtctcgc | ttcctcagta | cctatgatgg | agcagagacg | 840 |
| ctctgcctgg | aggacatata | cacagagaat | gtcctggagg | tctgggcaga | tgtgggcatg | 900 |
| gctggacccc | cgcagaagag | cccagccacc | ctgggcctgg | aggagctctt | cagcacccct | 960 |
| ggccacctca | atgacgatgc | ggacactgtg | ctggtggtgg | gtgaggcggg | cagtggcaag | 1020 |
| agcacgctcc | tgcagcggct | gcacttgctg | tgggctgcag | ggcaagactt | ccaggaattt | 1080 |
| ctctttgtct | tcccattcag | ctgccggcag | ctgcagtgca | tggccaaacc | actctctgtg | 1140 |
| cggactctac | tctttgagca | ctgctgttgg | cctgatgttg | gtcaagaaga | catcttccag | 1200 |
| ttactccttg | accaccctga | ccgtgtcctg | ttaacctttg | atggctttga | cgagttcaag | 1260 |
| ttcaggttca | cggatcgtga | acgccactgc | tccccgaccg | acccacctc | tgtccagacc | 1320 |

FIGURE 11A
SEQ ID NO:33

Nod2 cDNA sequence

```
gtagacagat ccaggctcac cagtcctgtg ccactgggct tttggcgttc tgcacaaggc    60
ctacccgcag atgccatgcc tgctccccca gcctaatggg ctttgatggg ggaagagggt   120
ggttcagcct ctcacgatga ggaggaaaga gcaagtgtcc tcctcggaca ttctccgggt   180
tgtgaaatgt gctcgcagga ggcttttcag gcacagagga ccagctggt cgagctgctg    240
gtctcagggt ccctggaagg cttcgagagt gtcctggact ggctgctgtc ctgggaggtc   300
ctctcctggg aggactacga gggcttccac ctcctgggcc agcctctctc ccacttggcc   360
aggcgccttc tggacaccgt ctggaataag ggtacttggg cctgtcagaa gctcatcgcg   420
gctgcccaag aagcccaggc cgacagccag tcccccaagc tgcatggctg ctgggacccc   480
cactcgctcc acccagcccg agacctgcag agtcaccggc cagccattgt caggaggctc   540
cacagccatg tggagaacat gctggacctg gcatgggagc ggggtttcgt cagccagtat   600
gaatgtgatg aaatcaggtt gccgatcttc acccgtccc agagggcaag aaggctgctt   660
gatcttgcca cggtgaaagc gaatggattg gctgccttcc ttctacaaca tgttcaggaa   720
ttaccagtcc cattggccct gcctttggaa gctgccacat gcaagaagta tatggccaag   780
ctgaggacca cggtgtctgc tcagtctcgc ttcctcagta cctatgatgg agcagagacg   840
ctctgcctgg aggacatata cacagagaat gtcctggagg tctgggcaga tgtgggcatg   900
gctggacccc cgcagaagag cccagccacc ctgggcctgg aggagctctt cagcacccct   960
ggccacctca tgacgatgc ggacactgtg ctggtggtgg gtgaggcggg cagtggcaag  1020
agcacgctcc tgcagcggct gcacttgctg tgggctgcag ggcaagactt ccaggaattt  1080
ctctttgtct tcccattcag ctgccggcag ctgcagtgca tggccaaacc actctctgtg  1140
cggactctac tctttgagca ctgctgttgg cctgatgttg gtcaagaaga tatcttccag  1200
ttactccttg accaccctga ccgtgtcctg taaccttg atggctttga cgagttcaag  1260
ttcaggttca cggatcgtga acgccactgc tccccgaccg accccacctc tgtccagacc  1320
ctgctcttca accttctgca gggcaacctg ctgaagaatg cccgcaaggt ggtgaccagc  1380
cgtccggccg ctgtgtcggc gttcctcagg aagtacatcc gcaccgagtt caacctcaag  1440
```

FIGURE 11 B

```
ggcttctctg aacagggcat cgagctgtac ctgaggaagc gccatcatga gcccggggtg     1500
gcggaccgcc tcatccgcct gctccaagag acctcagccc tgcacggttt gtgccacctg     1560
cctgtcttct catggatggt gtccaaatgc caccaggaac tgttgctgca ggagggggggg   1620 tccccaaaga ccactacaga tatgtacctg ctgattctgc agcattttct gctgcatgcc     1680 accccccag actcagcttc ccaaggtctg gacccagtc ttcttcgggg ccgcctcccc       1740
accctcctgc acctgggcag actggctctg tggggcctgg gcatgtgctg ctacgtgttc     1800
tcagcccagc agctccaggc agcacaggtc agccctgatg acattttctct tggcttcctg   1860 gtgcgtgcca aaggtgtcgt gccagggagt acggcgcccc tggaattcct tcacatcact   1920
ttccagtgct tctttgccgc gttctacctg gcactcagtg ctgatgtgcc accagctttg    1980
ctcagacacc tcttcaattg tggcaggcca ggcaactcac caatggccag gctcctgccc    2040
acgatgtgca tccaggcctc ggagggaaag gacagcagcg tggcagcttt gctgcagaag   2100
gccgagccgc acaaccttca gatcacagca gccttcctgg cagggctgtt gtcccgggag   2160
cactggggcc tgctggctga gtgccagaca tctgagaagg ccctgctccg gcgccaggcc   2220
tgtgcccgct ggtgtctggc ccgcagcctc gcaagcact tccactccat cccgccagct     2280
gcaccgggtg aggccaagag cgtgcatgcc atgcccgggt tcatctggct catccggagc    2340
ctgtacgaga tgcaggagga gcggctggct cggaaggctg cacgtggcct gaatgttggg    2400
cacctcaagt tgacatttg cagtgtgggc cccactgagt gtgctgccct ggcctttgtg     2460
ctgcagcacc tccggcggcc cgtggccctg cagctggact acaactctgt gggtgacatt   2520
ggcgtggagc agctgctgcc ttgccttggt gtctgcaagg ctctgtattt gcgcgataac   2580
aatatctcag accgaggcat ctgcaagctc attgaatgtg ctcttcactg cgagcaattg   2640
cagaagttag ctctattcaa caacaaattg actgacggct gtgcacactc catggctaag   2700
ctccttgcat gcaggcagaa cttcttggca ttgaggctgg ggaataacta catcactgcc   2760
gcgggagccc aagtgctggc cgaggggctc cgaggcaaca cctccttgca gttcctggga   2820
ttctggggca acagagtggg tgacgagggg gcccaggccc tggctgaagc cttgggtgat   2880
caccagagct tgaggtggct cagcctggtg gggaacaaca ttggcagtgt gggtgcccaa   2940
gccttggcac tgatgctggc aaagaacgtc atgctagaag aactctgcct ggaggagaac   3000
```

FIGURE 11 C

```
catctccagg atgaaggtgt atgttctctc gcagaaggac tgaagaaaaa ttcaagtttg   3060
aaaatcctga agttgtccaa taactgcatc acctacctag ggcagaagc cctcctgcag    3120 gccccttgaa aggaatgaca ccatcctgga agtctggctc cgagggaaca ctttctctct   3180
agaggaggtt gacaagctcg gctgcaggga caccagactc ttgctttgaa gtctccggga   3240
ggatgttcgt ctcagtttgt ttgtgagcag gctgtgagtt tgggcccag aggctgggtg    3300 acatgtgttg gcagcctctt caaaatgagc cctgtcctgc ctaaggctga acttgttttc   3360
tgggaacacc ataggtcacc tttattctgg cagaggaggg agcatcagtg ccctccagga   3420 tagactttc ccaagcctac ttttgccatt gacttcttcc caagattcaa tcccaggatg    3480
tacaaggaca gcccctcctc catagtatgg gactggcctc tgctgatcct cccaggcttc   3540
cgtgtgggtc agtggggccc atggatgtgc ttgttaactg agtgccttt ggtggagagg    3600 cccggcctct cacaaaagac cccttaccac tgctctgatg aagaggagta cacagaacac   3660
ataattcagg aagcagcttt ccccatgtct cgactcatcc atccaggcca ttccccgtct   3720
ctggttcctc ccctcctcct ggactcctgc acacgctcct tcctctgagg ctgaaattca   3780
gaatattagt gacctcagct ttgatatttc acttacagca cccccaaccc tggcacccag   3840
ggtgggaagg gctacacctt agcctgccct cctttccggt gtttaagaca tttttggaag   3900
gggacacgtg acagccgttt gttccccaag acattctagg tttgcaagaa aaatatgacc   3960
acactccagc tgggatcaca tgtggacttt tatttccagt gaaatcagtt actcttcagt   4020 taagccttg gaaacagctc gactttaaaa agctccaaat gcagctttaa aaaattaatc    4080
tgggccagaa tttcaaacgg cctcactagg cttctggttg atgcctgtga actgaactct   4140
gacaacagac ttctgaaata gacccacaag aggcagttcc atttcatttg tgccagaatg   4200
ctttaggatg tacagttatg gactgaaagt ttacaggaaa aaaaattagg ccgttccttc   4260
aaagcaaatg tcttcctgga ttattcaaaa tgatgtatgt tgaagccttt gtaaattgtc   4320
agatgctgtg caaatgttat tattttaaac attatgatgt gtgaaaactg gttaatattt   4380
ataggtcact ttgctttact gtcttaagtt tatactctta tagacaacat ggccgtgaac   4440
tttatgctgt aaataatcag aggggaataa actgttgagt caaaac                  4486
```

Figure 12

SEQ ID NO:1

Nod2 cDNA sequence

| | | | | | |
|---|---|---|---|---|---|
| gtagacagat | ccaggctcac | cagtcctgtg | ccactgggct | tttggcgttc | tgcacaaggc | 60 |
| ctaccgcag | atgccatgcc | tgctccccca | gcctaatggg | ctttgatggg | ggaagagggt | 120 |
| ggttcagcct | ctcacgatga | ggaggaaaga | gcaagtgtcc | tcctcggaca | ttctccgggt | 180 |
| tgtgaaatgt | gctcgcagga | ggcttttcag | gcacagagga | gccagctggt | cgagctgctg | 240 |
| gtctcagggt | ccctggaagg | cttcgagagt | gtcctggact | ggctgctgtc | ctggaggtc | 300 |
| ctctcctggg | aggactacga | gggcttccac | ctcctgggcc | agcctctctc | ccacttggcc | 360 |
| aggcgccttc | tggacaccgt | ctggaataag | ggtacttggg | cctgtcagaa | gctcatcgcg | 420 |
| gctgcccaag | aagcccaggc | cgacagccag | tcccccaagc | tgcatggctg | ctgggacccc | 480 |
| cactcgctcc | acccagcccg | agacctgcag | agtcaccggc | cagccattgt | caggaggctc | 540 |
| cacagccatg | tggagaacat | gctggacctg | gcatgggagc | ggggtttcgt | cagccagtat | 600 |
| gaatgtgatg | aaatcaggtt | gccgatcttc | acaccgtccc | agagggcaag | aaggctgctt | 660 |
| gatcttgcca | cggtgaaagc | gaatggattg | gctgccttcc | ttctacaaca | tgttcaggaa | 720 |
| ttaccagtcc | cattggccct | gcctttggaa | gctgccacat | gcaagaagta | tatggccaag | 780 |
| ctgaggacca | cggtgtctgc | tcagtctcgc | ttcctcagta | cctatgatgg | agcagagacg | 840 |
| ctctgcctgg | aggacatata | cacagagaat | gtcctggagg | tctgggcaga | tgtgggcatg | 900 |
| gctggaccc | cgcagaagag | cccagccacc | ctgggcctgg | aggagctctt | cagcaccct | 960 |
| ggccacctca | atgacgatgc | ggacactgtg | ctggtggtgg | gtgaggcggg | cagtggcaag | 1020 |
| agcacgctcc | tgcagcggct | gcacttgctg | tgggctgcag | ggcaagactt | ccaggaattt | 1080 |
| ctctttgtct | tcccattcag | ctgccggcag | ctgcagtgca | tggccaaacc | actctctgtg | 1140 |
| cggactctac | tctttgagca | ctgctgttgg | cctgatgttg | gtcaagaaga | catcttccag | 1200 |
| ttactccttg | accaccctga | ccgtgtcctg | ttaacctttg | atggctttga | cgagttcaag | 1260 |
| ttcaggttca | cggatcgtga | acgccactgc | tccccgaccg | accccacctc | tgtccagacc | 1320 |

FIGURE 12 A
SEQ ID NO:1

Nod2 cDNA sequence

| | | | | | |
|---|---|---|---|---|---:|
| gtagacagat | ccaggctcac | cagtcctgtg | ccactgggct | tttggcgttc | tgcacaaggc | 60 |
| ctaccgcag | atgccatgcc | tgctccccca | gctaatggg | ctttgatggg | ggaagagggt | 120 |
| ggttcagcct | ctcacgatga | ggaggaaaga | gcaagtgtcc | tcctcggaca | ttctccgggt | 180 |
| tgtgaaatgt | gctcgcagga | ggcttttcag | gcacagagga | cccagctggt | cgagctgctg | 240 |
| gtctcagggt | ccctggaagg | cttcgagagt | gtcctggact | ggctgctgtc | ctgggaggtc | 300 |
| ctctcctggg | aggactacga | gggcttccac | ctcctgggcc | agcctctctc | ccacttggcc | 360 |
| aggcgccttc | tggacaccgt | ctggaataag | ggtacttggg | cctgtcagaa | gctcatcgcg | 420 |
| gctgcccaag | aagcccaggc | cgacagccag | tcccccaagc | tgcatggctg | ctgggacccc | 480 |
| cactcgctcc | acccagcccg | agacctgcag | agtcaccggc | cagccattgt | caggaggctc | 540 |
| cacagccatg | tggagaacat | gctggacctg | gcatgggagc | ggggtttcgt | cagccagtat | 600 |
| gaatgtgatg | aaatcaggtt | gccgatcttc | acacgtccc | agagggcaag | aaggctgctt | 660 |
| gatcttgcca | cggtgaaagc | gaatggattg | gctgccttcc | ttctacaaca | tgttcaggaa | 720 |
| ttaccagtcc | cattggccct | gcctttggaa | gctgccacat | gcaagaagta | tatggccaag | 780 |
| ctgaggacca | cggtgtctgc | tcagtctcgc | ttcctcagta | cctatgatgg | agcagagacg | 840 |
| ctctgcctgg | aggacatata | cacagagaat | gtcctggagg | tctgggcaga | tgtgggcatg | 900 |
| gctggacccc | cgcagaagag | cccagccacc | ctgggcctgg | aggagctctt | cagcacccct | 960 |
| ggccacctca | atgacgatgc | ggacactgtg | ctgctggtgg | gtgaggcggg | cagtggcaag | 1020 |
| agcacgctcc | tgcagcggct | gcacttgctg | tgggctgcag | ggcaagactt | ccaggaattt | 1080 |
| ctctttgtct | tcccattcag | ctgccggcag | ctgcagtgca | tggccaaacc | actctctgtg | 1140 |
| cggactctac | tctttgagca | ctgctgttgg | cctgatgttg | gtcaagaaga | catcttccag | 1200 |
| ttactccttg | accacctga | ccgtgtcctg | ttaacctttg | atggctttga | cgagttcaag | 1260 |
| ttcaggttca | cggatcgtga | acgccactgc | tccccgaccg | accccacctc | tgtccagacc | 1320 |
| ctgctcttca | accttctgca | gggcaacctg | ctgaagaatg | cccgcaaggt | ggtgaccagc | 1380 |
| cgtccggccg | ctgtgtcggc | gttcctcagg | aagtacatcc | gcaccgagtt | caacctcaag | 1440 |

FIGURE 12 B

```
ggcttctctg aacagggcat cgagctgtac ctgaggaagc gccatcatga gcccggggtg    1500
gcggaccgcc tcatccgcct gctccaagag acctcagccc tgcacggttt gtgccacctg    1560
cctgtcttct catggatggt gtccaaatgc caccaggaac tgttgctgca ggagggggggg   1620 tccccaaaga ccactacaga tatgtacctg ctgattctgc agcattttct gctgcatgcc    1680
acccccccag actcagcttc caaggtctg ggacccagtc ttcttcgggg ccgcctcccc     1740
accctcctgc acctgggcag actggctctg tggggcctgg gcatgtgctg ctacgtgttc    1800
tcagcccagc agctccaggc agcacaggtc agccctgatg acatttctct tggcttcctg    1860
gtgcgtgcca aggtgtcgt gccagggagt acggcgcccc tggaattcct tcacatcact     1920
ttccagtgct ctttgccgc gttctacctg gcactcagtg ctgatgtgcc accagctttg     1980
ctcagacacc tcttcaattg tggcaggcca ggcaactcac caatggccag gctcctgccc    2040
acgatgtgca tccaggcctc ggagggaaag gacagcagcg tggcagcttt gctgcagaag    2100
gccgagccgc acaaccttca gatcacagca gccttcctgg cagggctgtt gtcccgggag    2160
cactggggcc tgctggctga gtgccagaca tctgagaagg ccctgctccg gcgccaggcc    2220
tgtgcccgct ggtgtctggc ccgcagcctc cgcaagcact ccactccat ccgccagct     2280 gcaccgggtg aggccaagag cgtgcatgcc atgcccgggt tcatctggct catccggagc    2340
ctgtacgaga tgcaggagga gcggctggct cggaaggctg cacgtggcct gaatgttggg    2400
cacctcaagt tgacattttg cagtgtgggc cccactgagt gtgctgccct ggcctttgtg    2460
ctgcagcacc tccggcggcc cgtggccctg cagctggact acaactctgt gggtgacatt    2520
ggcgtggagc agctgctgcc ttgccttggt gtctgcaagg ctctgtattt gcgcgataac    2580
aatatctcag accgaggcat ctgcaagctc attgaatgtg ctcttcactg cgagcaattg    2640
cagaagttag ctctattcaa caacaaattg actgacggct gtgcacactc catggctaag    2700
ctccttgcat gcaggcagaa cttcttggca ttgaggctgg ggaataacta catcactgcc    2760
gcgggagccc aagtgctggc cgaggggctc cgaggcaaca cctccttgca gttcctggga    2820
ttctggggca acagagtggg tgacgagggg gcccaggccc tggctgaagc cttgggtgat    2880
caccagagct tgaggtggct cagcctggtg gggaacaaca ttggcagtgt gggtgcccaa    2940
gccttggcac tgatgctggc aaagaacgtc atgctagaag aactctgcct ggaggagaac    3000
catctccagg atgaaggtgt atgttctctc gcagaaggac tgaagaaaaa ttcaagtttg   3060
```

FIGURE 12 C

```
aaaatcctga agttgtccaa taactgcatc acctacctag gggcagaagc cctcctgcag      3120
gcccttgaaa ggaatgacac catcctggaa gtctggctcc gagggaacac tttctctcta      3180
gaggaggttg acaagctcgg ctgcagggac accagactct gctttgaag tctccgggag       3240 gatgttcgtc tcagtttgtt tgtgagcagg ctgtgagttt gggccccaga ggctgggtga      3300
catgtgttgg cagcctcttc aaaatgagcc ctgtcctgcc taaggctgaa cttgttttct      3360
gggaacacca taggtcacct ttattctggc agaggaggga gcatcagtgc cctccaggat      3420
agacttttcc caagcctact tttgccattg acttcttccc aagattcaat cccaggatgt      3480
acaaggacag cccctcctcc atagtatggg actggcctct gctgatcctc ccaggcttcc      3540
gtgtgggtca gtggggccca tggatgtgct tgttaactga gtgccttttg gtggagaggc      3600
ccggcctctc acaaaagacc ccttaccact gctctgatga agaggagtac acagaacaca      3660
taattcagga agcagctttc cccatgtctc gactcatcca tccaggccat tccccgtctc      3720
tggttcctcc cctcctcctg gactcctgca cacgctcctt cctctgaggc tgaaattcag      3780
aatattagtg acctcagctt tgatatttca cttacagcac ccccaaccct ggcacccagg      3840
gtgggaaggg ctacacctta gcctgccctc ctttccggtg tttaagacat ttttggaagg      3900
ggacacgtga cagccgtttg ttccccaaga cattctaggt ttgcaagaaa aatatgacca      3960
cactccagct gggatcacat gtggactttt atttccagtg aaatcagtta ctcttcagtt      4020
aagcctttgg aaacagctcg actttaaaaa gctccaaatg cagcttaaa aaattaatct       4080 gggccagaat ttcaaacggc ctcactaggc ttctggttga tgcctgtgaa ctgaactctg      4140
acaacagact tctgaaatag acccacaaga ggcagttcca tttcatttgt gccagaatgc      4200
tttaggatgt acagttatgg attgaaagtt tacaggaaaa aaaattaggc cgttccttca      4260
aagcaaatgt cttcctggat tattcaaaat gatgtatgtt gaagcctttg taaattgtca      4320
gatgctgtgc aaatgttatt attttaaaca ttatgatgtg tgaaaactgg ttaatattta      4380
taggtcactt tgttttactg tcttaagttt atactcttat agacaacatg gccgtgaact      4440
ttatgctgta ataatcaga ggggaataaa ctgttgagtc aaaac                       4485
```

Figure 13

SEQ ID NO:2

```
MGEEGGSASH DEEERASVLL GHSPGCEMCS QEAFQAQRSQ LVELLVSGSL EGFESVLDWL
LSWEVLSWED YEGFHLLGQP LSHLARRLLD TVWNKGTWAC QKLIAAAQEA QADSQSPKLH
GCWDPHSLHP ARDLQSHRPA IVRRLHSHVE NMLDLAWERG FVSQYECDEI RLPIFTPSQR
ARRLLDLATV KANGLAAFLL QHVQELPVPL ALPLEAATCK KYMAKLRTTV SAQSRFLSTY
DGAETLCLED IYTENVLEVW ADVGMAGPPQ KSPATLGLEE LFSTPGHLND DADTVLVVGE
AGSGKSTLLQ RLHLLWAAGQ DFQEFLFVFP FSCRQLQCMA KPLSVRTLLF EHCCWPDVGQ
EDIFQLLLDH PDRVLLTFDG FDEFKFRFTD RERHCSPTDP TSVQTLLFNL LQGNLLKNAR
KVVTSRPAAV SAFLRKYIRT EFNLKGFSEQ GIELYLRKRH HEPGVADRLI RLLQETSALH
GLCHLPVFSW MVSKCHQELL LQEGGSPKTT TDMYLLILQH FLLHATPPDS ASQGLGPSLL
RGRLPTLLHL GRLALWGLGM CCYVFSAQQL QAAQVSPDDI SLGFLVRAKG VVPGSTAPLE
FLHITFQCFF AAFYLALSAD VPPALLRHLF NCGRPGNSPM ARLLPTMCIQ ASEGKDSSVA
ALLQKAEPHN LQITAAFLAG LLSREHWGLL AECQTSEKAL LRRQACARWC LARSLRKHFH
SIPPAAPGEA KSVHAMPGFI WLIRSLYEMQ EERLARKAAR GLNVGHLKLT FCSVGPTECA
ALAFVLQHLR RPVALQLDYN SVGDIGVEQL LPCLGVCKAL YLRDNNISDR GICKLIECAL
HCEQLQKLAL FNNKLTDGCA HSMAKLLACR QNFLALRLGN NYITAAGAQV LAEGLRGNTS
LQFLGFWGNR VGDEGAQALA EALGDHQSLR WLSLVGNNIG SVGAQALALM LAKNVMLEEL
CLEENHLQDE GVCSLAEGLK KNSSLKILKL SNNCITYLGA EALLQALERN DTILEVWLRG
NTFSLEEVDK LGCRDTRLLL *
```

Figure 14

SEQ ID NO:3

```
MCSQEAFQAQ RSQLVELLVS GSLEGFESVL DWLLSWEVLS WEDYEGFHLL GQPLSHLARR
LLDTVWNKGT WACQKLIAAA QEAQADSQSP KLHGCWDPHS LHPARDLQSH RPAIVRRLHS
HVENMLDLAW ERGFVSQYEC DEIRLPIFTP SQRARRLLDL ATVKANGLAA FLLQHVQELP
VPLALPLEAA TCKKYMAKLR TTVSAQSRFL STYDGAETLC LEDIYTENVL EVWADVGMAG
PPQKSPATLG LEELFSTPGH LNDDADTVLV VGEAGSGKST LLQRLHLLWA AGQDFQEFLF
VFPFSCRQLQ CMAKPLSVRT LLFEHCCWPD VGQEDIFQLL LDHPDRVLLT FDGFDEFKFR
FTDRERHCSP TDPTSVQTLL FNLLQGNLLK NARKVVTSRP AAVSAFLRKY IRTEFNLKGF
SEQGIELYLR KRHHEPGVAD RLIRLLQETS ALHGLCHLPV FSWMVSKCHQ ELLLQEGGSP
KTTTDMYLLI LQHFLLHATP PDSASQGLGP SLLRGRLPTL LHLGRLALWG LGMCCYVFSA
QQLQAAQVSP DDISLGFLVR AKGVVPGSTA PLEFLHITFQ CFFAAFYLAL SADVPPALLR
HLFNCGRPGN SPMARLLPTM CIQASEGKDS SVAALLQKAE PHNLQITAAF LAGLLSREHW
GLLAECQTSE KALLRRQACA RWCLARSLRK HFHSIPPAAP GEAKSVHAMP GFIWLIRSLY
EMQEERLARK AARGLNVGHL KLTFCSVGPT ECAALAFVLQ HLRRPVALQL DYNSVGDIGV
EQLLPCLGVC KALYLRDNNI SDRGICKLIE CALHCEQLQK LALFNNKLTD GCAHSMAKLL
ACRQNFLALR LGNNYITAAG AQVLAEGLRG NTSLQFLGFW GNRVGDEGAQ ALAEALGDHQ
SLRWLSLVGN NIGSVGAQAL ALMLAKNVML EELCLEENHL QDEGVCSLAE GLKKNSSLKI
LKLSNNCITY LGAEALLQAL ERNDTILEVW LRGNTFSLEE VDKLGCRDTR LLL*
```

Figure 15
SEQ ID NO:34

Nod2a AA sequence, Mutant

```
MGEEGGSASH DEEERASVLL GHSPGCEMCS QEAFQAQRSQ LVELLVSGSL EGFESVLDWL
LSWEVLSWED YEGFHLLGQP LSHLARRLLD TVWNKGTWAC QKLIAAAQEA QADSQSPKLH
GCWDPHSLHP ARDLQSHRPA IVRRLHSHVE NMLDLAWERG FVSQYECDEI RLPIFTPSQR
ARRLLDLATV KANGLAAFLL QHVQELPVPL ALPLEAATCK KYMAKLRTTV SAQSRFLSTY
DGAETLCLED IYTENVLEVW ADVGMAGPPQ KSPATLGLEE LFSTPGHLND DADTVLVVGE
AGSGKSTLLQ RLHLLWAAGQ DFQEFLFVFP FSCRQLQCMA KPLSVRTLLF EHCCWPDVGQ
EDIFQLLLDH PDRVLLTFDG FDEFKFRFTD RERHCSPTDP TSVQTLLFNL LQGNLLKNAR
KVVTSRPAAV SAFLRKYIRT EFNLKGFSEQ GIELYLRKRH HEPGVADRLI RLLQETSALH
GLCHLPVFSW MVSKCHQELL LQEGGSPKTT TDMYLLILQH FLLHATPPDS ASQGLGPSLL
RGRLPTLLHL GRLALWGLGM CCYVFSAQQL QAAQVSPDDI SLGFLVRAKG VVPGSTAPLE
FLHITFQCFF AAFYLALSAD VPPALLRHLF NCGRPGNSPM ARLLPTMCIQ ASEGKDSSVA
ALLQKAEPHN LQITAAFLAG LLSREHWGLL AECQTSEKAL LRRQACARWC LARSLRKHFH
SIPPAAPGEA KSVHAMPGFI WLIRSLYEMQ EERLARKAAR GLNVGHLKLT FCSVGPTECA
ALAFVLQHLR RPVALQLDYN SVGDIGVEQL LPCLGVCKAL YLRDNNISDR GICKLIECAL
HCEQLQKLAL FNNKLTDGCA HSMAKLLACR QNFLALRLGN NYITAAGAQV LAEGLRGNTS
LQFLGFWGNR VGDEGAQALA EALGDHQSLR WLSLVGNNIG SVGAQALALM LAKNVMLEEL
CLEENHLQDE GVCSLAEGLK KNSSLKILKL SNNCITYLGA EALLQAP*
```

FIGURE 16

Nod2 Exon11, Wild type cagacatgag caggatgtgt ctaagggaca ggtgggcttc agtagactgg ctaactcctg cagtctcttt aactggacag tttcaagagg aaaaccaaga atccttgaag ctcaccattg tatcttcttt tccag<u>GTTGT CCAATAACTG CATCACCTAC CTAGGGGCAG AAGCCCTCCT</u>
                L  S   N  N  C   I  T  Y  L   G  A  E   A  L  L <u>GCAGGCCCTT GAAAGGAATG ACACCATCCT GGAAGTCTG</u>g taaggcccct gggcaggcct
 Q  A  L   E  R  N   D  T  I   L   E  V gttttagctc tccgaacctc agtttttcta tctgtaaaat ggggtgacgg gagagaggaa tggcagaatt ttgaggatcc cttctgattc tgacattcag tgagaatgat tctgcatgtg Nod2 Exon11, Mutant cagacatgag caggatgtgt ctaagggaca ggtgggcttc agtagactgg ctaactcctg cagtctcttt aactggacag tttcaagagg aaaaccaaga atccttgaag ctcaccattg tatcttcttt tccag<u>GTTGT CCAATAACTG CATCACCTAC CTAGGGGCAG AAGCCCTCCT</u>
                L  S   N  N  C   I  T  Y  L   G  A  E   A  L  L <u>GCAGGCCCCT TGAAAGGAAT GACACCATCC TGGAAGTCTG</u> gtaaggcccc tgggcaggcc

FIGURE 16A

Nod2 Exon11, Wild type cagacatgag caggatgtgt ctaagggaca ggtgggcttc agtagactgg ctaactcctg cagtctcttt aactggacag tttcaagagg aaaaccaaga atccttgaag ctcaccattg tatcttcttt tccag<u>GTTGT CCAATAACTG CATCACCTAC CTAGGGCAG AAGCCCTCCT</u>
                 L   S    N  N   C    I  T  Y    L  G  A    E  A    L  L <u>GCAGGCCCTT GAAAGGAATG ACACCATCCT GGAAGTCTG</u>g taaggcccct gggcaggcct
 Q  A  L    E  R  N    D  T  I    L  E    V gttttagctc tccgaacctc agtttttcta tctgtaaaat ggggtgacgg gagagaggaa tggcagaatt ttgaggatcc cttctgattc tgacattcag tgagaatgat tctgcatgtg Nod2 Exon11, Mutant cagacatgag caggatgtgt ctaagggaca ggtgggcttc agtagactgg ctaactcctg cagtctcttt aactggacag tttcaagagg aaaaccaaga atccttgaag ctcaccattg tatcttcttt tccag<u>GTTGT CCAATAACTG CATCACCTAC CTAGGGCAG AAGCCCTCCT</u>
                 L   S    N  N   C    I  T  Y    L  G  A    E  A    L  L <u>GCAGGCCCCT TGAAAGGAAT GACACCATCC TGGAAGTCTG</u> gtaaggcccc tgggcaggcc

FIGURE 16 B

Q  A  P  * tgttttagct ctccgaacct cagtttttct atctgtaaaa tggggtgacg ggagagagga atggcagaat tttgaggatc ccttctgatt ctgacattca gtgagaatga ttctgcatgt g

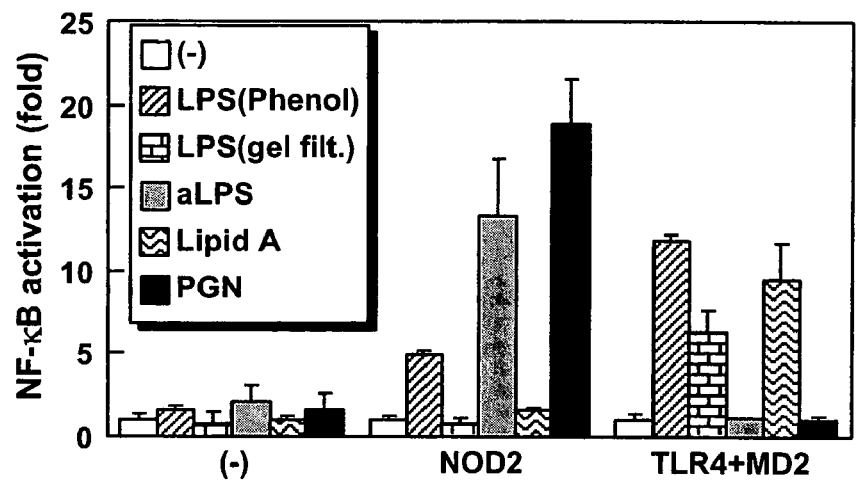
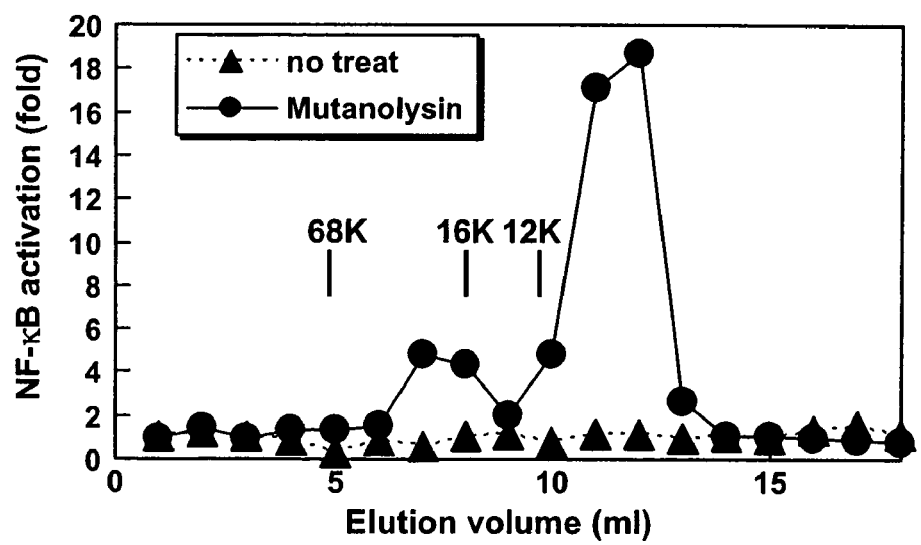
Figure 17

A
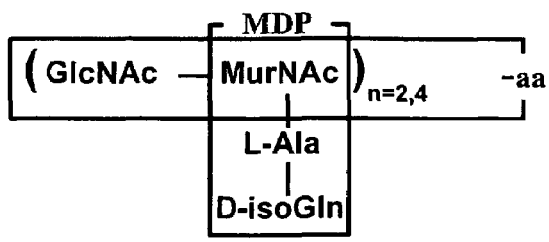
B
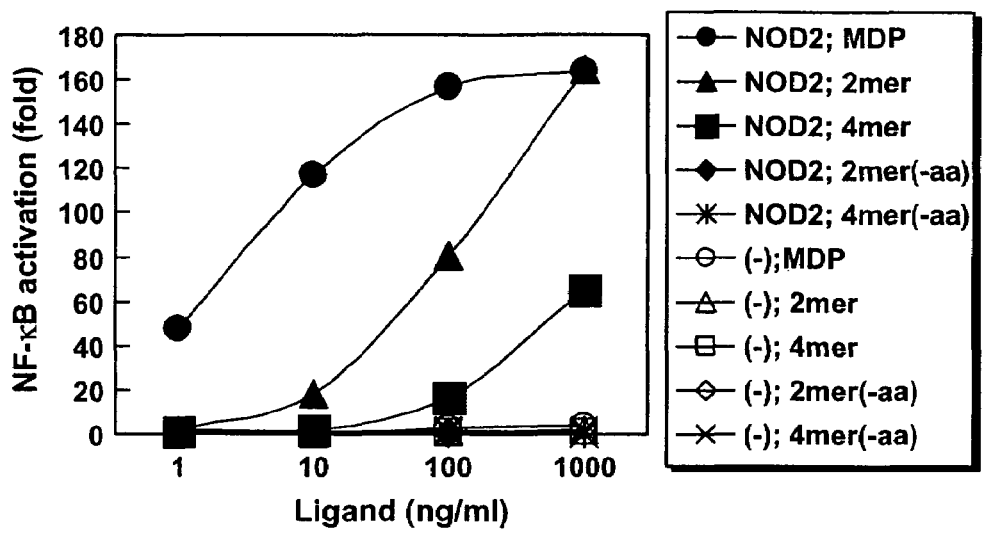
C
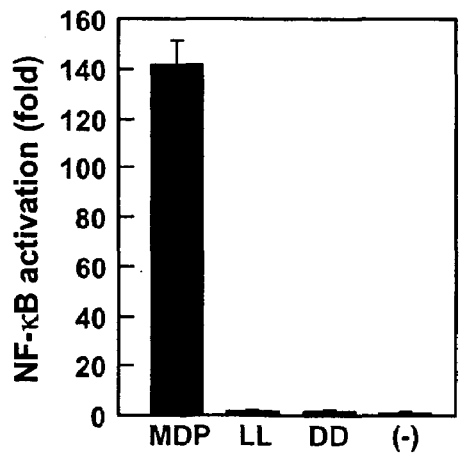
D
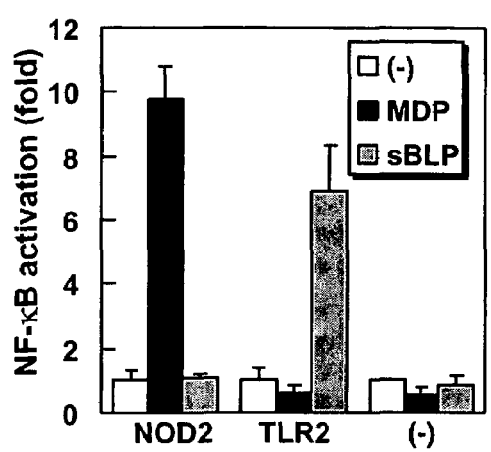
Figure 18

Figure 21
SEQ ID NO: 54

```
atgggggaagagggtggttcagcctctcacgatgaggaggaaagagcaagtgtcctcctcggacattctccggggttgtga
aatgtgctcgcaggaggcttttcaggcacagaggagccagctggtcgagctgctggtctcagggtccctggaaggcttcg
agagtgtcctggactggctgctgtcctgggaggtcctctcctggggaggactacgagggcttccacctcctgggccagcct
ctctcccacttggccaggcgccttctggacaccgtctggaataagggtacttgggcctgtcagaagctcatcgcggctgc
ccaagaagcccaggccgacagccagtcccccaagctgcatggctgctgggaccccactcgctccacccagcccgagacc
tgcagagtcaccggccagccattgtcaggaggctccacagccatgtggagaacatgctggacctggcatgggagcggggt
ttcgtcagccagtatgaatgtgatgaaatcaggttgccgatcttcacaccgtcccagagggcaagaaggctgcttgatct
tgccacggtgaaagcgaatggattggctgccttccttctacaacatgttcaggaattaccagtcccattggccctgcctt
tggaagctgccacatgcaagaagtatatggccaagctgaggaccacggtgtctgctcagtctcgcttcctcagtacctat
gatggagcagagacgctctgcctggaggacatatacacagagaatgtcctggaggtctgggcagatgtgggcatggctgg
atccccgcagaagagcccagccaccctgggcctggaggagctcttcagcacccctggccacctcaatgacgatgcggaca
ctgtgctggtggtgggtgaggcgggcagtggcaagagcacgctcctgcagcggctgcacttgctgtgggctgcagggcaa
gacttccaggaatttctctttgtcttcccattcagctgccggcagctgcagtgcatggccaaaccactctctgtgcggac
tctactctttgagcactgctgttggcctgatgttggtcaagaagacatcttccagttactccttgaccaccctgaccgtg
tcctgttaacctttgatggctttgacgagttcaagttcaggttcacggatcgtgaacgccactgctccccgaccgacccc
acctctgtccagaccctgctcttcaaccttctgcagggcaacctgctgaagaatgcccgcaaggtggtgaccagccgtcc
ggccgctgtgtcggcgttcctcaggaagtacatccgcaccgagttcaacctcaagggcttctctgaacagggcatcgagc
tgtacctgaggaagcgccatcatgagcccggggtggcggaccgcctcatccgcctgctccaagagacctcagccctgcac
ggtttgtgccacctgcctgtcttctcatggatggtgtccaaatgccaccaggaactgttgctgcaggagggggggtcccc
aaagaccactacagatatgtacctgctgattctgcagcattttctgctgcatgccaccccccagactcagcttcccaag
gtctgggacccagtcttcttcggggccgcctccccaccctcctgcacctgggcagactggctctgtggggcctggcatg
tgctgctacgtgttctcagcccagcagctccaggcagcacaggtcagccctgatgacatttctcttggcttcctggtgcg
tgccaaaggtgtcgtgccagggagtacggcgcccctggaattccttcacatcactttccagtgcttctttgccgcgttct
acctggcactcagtgctgatgtgccaccagctttgctcagacacctcttcaattgtggcaggccaggcaactcaccaatg
gccaggctcctgcccacgatgtgcatccaggcctcggagggaaaggacagcagcgtggcagctttgctgcagaaggccga
gccgcacaaccttcagatcacagcagccttcctgcagggctgttgtcccgggagcactggggcctgctggctgagtgcc
agacatctgagaaggccctgctccggcgccaggcctgtgcccgctggtgtctggcccgcagcctccgcaagcacttccac
tccatcccgccagctgcaccgggtgaggccaagagcgtgcatgccatgcccgggttcatctggctcatccggagcctgta
cgagatgcaggaggagcggctggctcggaaggctgcacgtggcctgaatgtgggcacctcaagttgacattttgcagtg
tgggccccactgagtgtgctgccctggcctttgtgctgcagcacctccggcggcccgtggccctgcagctggactacaac
tctgtgggtgacattggcgtggagcagctgctgccttgccttggtgtctgcaaggctctgtatttgcgcgataacaatat
ctcagaccgaggcatctgcaagctcattgaatgtgctcttcactgcgagcaattgcagaagttagctctattcaacaaca
aattgactgacggctgtgcacactccatggctaagctccttgcatgcaggcagaacttcttggcattgaggctggggaat
aactacatcactgccgcgggagcccaagtgctggccgaggggctccgaggcaacacctccttgcagttcctgggattctg
gggcaacagagtgggtgacgaggggcccaggccctggctgaagccttgggtgatcaccagagcttgaggtggctcagcc
tggtgggga`acaacattggcagtgtgggtgcccaagccttggcactgatgctggcaaagaacgtcatgctagaagaactc
tgcctggaggagaaccatctccaggatgaaggtgtatgttctctcgcagaaggactgaagaaaattcaagtttgaaaat
cctgaagttgtccaataactgcatcacctacctaggggcagaagccctcctgcaggcccttgaaaggaatgacaccatc
ctggaagtctggctccgagggaacactttctctctagaggaggttgacaagctcggctgcagggacaccagactcttgct
ttga
```

Figure 22
SEQ ID NO: 55

```
     MGEEGGSASH DEEERASVLL GHSPGCEMCS QEAFQAQRSQ LVELLVSGSL EGFESVLDWL
 60
     LSWEVLSWED YEGFHLLGQP LSHLARRLLD TVWNKGTWAC QKLIAAAQEA QADSQSPKLH
120
     GCWDPHSLHP ARDLQSHRPA IVRRLHSHVE NMLDLAWERG FVSQYECDEI RLPIFTPSQR
180
     ARRLLDLATV KANGLAAFLL QHVQELPVPL ALPLEAATCK KYMAKLRTTV SAQSRFLSTY
240
     DGAETLCLED IYTENVLEVW ADVGMAGSPQ KSPATLGLEE LFSTPGHLND DADTVLVVGE
300
     AGSGKSTLLQ RLHLLWAAGQ DFQEFLFVFP FSCRQLQCMA KPLSVRTLLF EHCCWPDVGQ
360
     EDIFQLLLDH PDRVLLTFDG FDEFKFRFTD RERHCSPTDP TSVQTLLFNL LQGNLLKNAR
420
     KVVTSRPAAV SAFLRKYIRT EFNLKGFSEQ GIELYLRKRH HEPGVADRLI RLLQETSALH
480
     GLCHLPVFSW MVSKCHQELL LQEGGSPKTT TDMYLLILQH FLLHATPPDS ASQGLGPSLL
540
     RGRLPTLLHL GRLALWGLGM CCYVFSAQQL QAAQVSPDDI SLGFLVRAKG VVPGSTAPLE
600
     FLHITFQCFF AAFYLALSAD VPPALLRHLF NCGRPGNSPM ARLLPTMCIQ ASEGKDSSVA
660
     ALLQKAEPHN LQITAAFLAG LLSREHWGLL AECQTSEKAL LRRQACARWC LARSLRKHFH
720
     SIPPAAPGEA KSVHAMPGFI WLIRSLYEMQ EERLARKAAR GLNVGHLKLT FCSVGPTECA
780
     ALAFVLQHLR RPVALQLDYN SVGDIGVEQL LPCLGVCKAL YLRDNNISDR GICKLIECAL
840
     HCEQLQKLAL FNNKLTDGCA HSMAKLLACR QNFLALRLGN NYITAAGAQV LAEGLRGNTS
900
     LQFLGFWGNR VGDEGAQALA EALGDHQSLR WLSLVGNNIG SVGAQALALM LAKNVMLEEL
960
     CLEENHLQDE GVCSLAEGLK KNSSLKILKL SNNCITYLGA EALLQAP*
1007
```

Figure 23
SEQ ID NO: 56

```
atgggggaagagggtggttcagcctctcacgatgaggaggaaagagcaagtgtcctcctcggacattctccgggttgtga
aatgtgctcgcaggaggcttttcaggcacagaggagccagctggtcgagctgctggtctcagggtccctggaaggcttcg
agagtgtcctggactggctgctgtcctggaggtcctctcctggaggactacgagggcttccacctcctgggccagcct
ctctcccacttggccaggcgccttctggacaccgtctggaataagggtacttgggcctgtcagaagctcatcgcggctgc
ccaagaagcccaggccgacagccagtcccccaagctgcatggctgctgggaccccactcgctccacccagcccgagacc
tgcagagtcaccggccagccattgtcaggaggctccacagccatgtggagaacatgctggacctggcatgggagcggggt
ttcgtcagccagtatgaatgtgatgaaatcaggttgccgatcttcacaccgtcccagagggcaagaaggctgcttgatct
tgccacggtgaaagcgaatggattggctgccttccttctacaacatgttcaggaattaccagtcccattggccctgcctt
tggaagctgccacatgcaagaagtatatggccaagctgaggaccacggtgtctgctcagtctcgcttcctcagtacctat
gatggagcagagacgctctgcctggaggacatatacacagagaatgtcctggaggtctgggcagatgtgggcatggctgg
atccccgcagaagagcccagccaccctgggcctggaggagctcttcagcacccctggccacctcaatgacgatgcggaca
ctgtgctggtggtgggtgaggcgggcagtggcaagagcacgctcctgcagcggctgcacttgctgtgggctgcagggcaa
gacttccaggaatttctctttgtcttcccattcagctgccggcagctgcagtgcatggccaaaccactctctgtgcggac
tctactctttgagcactgctgttggcctgatgttggtcaagaagacatcttccagttactccttgaccaccctgaccgtg
tcctgttaacctttgatggctttgacgagttcaagttcaggttcacggatcgtgaacgccactgctccccgaccgaccc
acctctgtccagaccctgctcttcaaccttctgcagggcaacctgctgaagaatgcccgcaaggtggtgaccagccgtcc
ggccgctgtgtcggcgttcctcaggaagtacatccgcaccgagttcaacctcaagggcttctctgaacagggcatcgagc
tgtacctgaggaagcgccatcatgagcccggggtggcggaccgcctcatccgcctgctccaagagacctcagccctgcac
ggtttgtgccacctgcctgtcttctcatggatggtgtccaaatgccaccaggaactgttgctgcaggagggggggtcccc
aaagaccactacagatatgtacctgctgattctgcagcattttctgctgcatgccacccccccagactcagcttcccaag
gtctggacccagtcttcttcggggcgcctccccaccctcctgcacctgggcagactggctctgtggggcctgggcatg
tgctgctacgtgttctcagcccagcagctccaggcagcacaggtcagccctgatgacatttctcttggcttcctggtgcg
tgccaaaggtgtcgtgccagggagtacggcgcccctggaattccttcacatcactttccagtgcttctttgccgcgttct
acctggcactcagtgctgatgtgccaccagctttgctcagacacctcttcaattgtggcaggccaggcaactcaccaatg
gccaggctcctgcccacgatgtgcatccaggcctcggagggaaaggacagcagcgtggcagctttgctgcagaaggccga
gccgcacaaccttcagatcacagcagccttcctggcagggctgttgtcccggggagcactggggcctgctggctgagtgcc
agacatctgagaaggccctgctccggcgccaggcctgtgcccgctggtgtctggcccgcagcctccgcaagcacttccac
tccatcccgccagctgcaccgggtgaggccaagagcgtgcatgccatgcccgggttcatctggctcatccggagcctgta
cgagatgcaggaggagcggctggctcggaaggctgcacgtggcctgaatgttgggcacctcaagttgacattttgcagtg
tgggccccactgagtgtgctgccctggcctttgtgctgcagcacctccggcggcccgtggccctgcagctggactacaac
tctgtgggtgacattggcgtggagcagctgctgccttgccttggtgtctgcaaggctctgtatttgcgcgataacaatat
ctcagaccgaggcatctgcaagctcattgaatgtgctcttcactgcgagcaattgcagaagttagctctattcaacaaca
aattgactgacggctgtgcacactccatggctaagctccttgcatgcaggcagaacttcttggcattgaggctggggaat
aactacatcactgccgcgggagcccaagtgctggccgaggggctccgaggcaacacctccttgcagttcctgggattctg
gggcaacagagtgggtgacgaggggggcccaggccctggctgaagccttgggtgatcaccagagcttgaggtggctcagcc
tggtgggaacaacattggcagtgtgggtgcccaagccttggcactgatgctggcaaagaacgtcatgctagaagaactc
tgcctggaggagaaccatctccaggatgaaggtgtatgttctctcgcagaaggactgaagaaaaattcaagtttgaaaat
cctgaagttgtccaataactgcatcacctacctaggggcagaagccctcctgcaggcccttgaaaggaatgacaccatcc
tggaagtctggctccgagggaacactttctctctagaggaggttgacaagctcggctgcagggacaccagactcttgctt
tga
```

Figure 24
SEQ ID NO: 57

```
MGEEGGSASHDEEERASVLLGHSPGCEMCSQEAFQAQRSQLVELLVSGSLEGFESVLDWLLSWEVLSWEDYEGFHLLGQP
LSHLARRLLDTVWNKGTWACQKLIAAAQEAQADSQSPKLHGCWDPHSLHPARDLQSHRPAIVRRLHSHVENMLDLAWERG
FVSQYECDEIRLPIFTPSQRARRLLDLATVKANGLAAFLLQHVQELPVPLALPLEAATCKKYMAKLRTTVSAQSRFLSTY
DGAETLCLEDIYTENVLEVWADVGMAGSPQKSPATLGLEELFSTPGHLNDDADTVLVVGEAGSGKSTLLQRLHLLWAAGQ
DFQEFLFVFPFSCRQLQCMAKPLSVRTLLFEHCCWPDVGQEDIFQLLLDHPDRVLLTFDGFDEFKFRFTDRERHCSPTDP
TSVQTLLFNLLQGNLLKNARKVVTSRPAAVSAFLRKYIRTEFNLKGFSEQGIELYLRKRHHEPGVADRLIRLLQETSALH
GLCHLPVFSWMVSKCHQELLLQEGGSPKTTTDMYLLILQHFLLHATPPDSASQGLGPSLLRGRLPTLLHLGRLALWGLGM
CCYVFSAQQLQAAQVSPDDISLGFLVRAKGVVPGSTAPLEFLHITFQCFFAAFYLALSADVPPALLRHLFNCGRPGNSPM
ARLLPTMCIQASEGKDSSVAALLQKAEPHNLQITAAFLAGLLSREHWGLLAECQTSEKALLRRQACARWCLARSLRKHFH
SIPPAAPGEAKSVHAMPGFIWLIRSLYEMQEERLARKAARGLNVGHLKLTFCSVGPTECAALAFVLQHLRRPVALQLDYN
SVGDIGVEQLLPCLGVCKALYLRDNNISDRGICKLIECALHCEQLQKLALFNNKLTDGCAHSMAKLLACRQNFLALRLGN
NYITAAGAQVLAEGLRGNTSLQFLGFWGNRVGDEGAQALAEALGDHQSLRWLSLVGNNIGSVGAQALALMLAKNVMLEEL
CLEENHLQDEGVCSLAEGLKKNSSLKILKLSNNCITYLGAEALLQALERNDTILEVWLRGNTFSLEEVDKLGCRDTRLLL
*
```

Figure 25
SEQ ID NO: 58

```
atgggggaagagggtggttcagcctctcacgatgaggaggaaagagcaagtgtcctcctcggacattctccggggttgtga
aatgtgctcgcaggaggcttttcaggcacagaggagccagctggtcgagctgctggtctcagggtccctggaaggcttcg
agagtgtcctggactggctgctgtcctgggaggtcctctcctgggaggactacgagggcttccacctcctgggccagcct
ctctcccacttggccaggcgccttctggacaccgtctggaataagggtacttgggcctgtcagaagctcatcgcggctgc
ccaagaagcccaggccgacagccagtcccccaagctgcatggctgctgggaccccactcgctccacccagcccgagacc
tgcagagtcaccggccagccattgtcaggaggctccacagccatgtggagaacatgctggacctggcatgggagcggggt
ttcgtcagccagtatgaatgtgatgaaatcaggttgccgatcttcacaccgtcccagagggcaagaaggctgcttgatct
tgccacggtgaaagcgaatggattggctgccttccttctacaacatgttcaggaattaccagtcccattggccctgcctt
tggaagctgccacatgcaagaagtatatggccaagctgaggaccacggtgtctgctcagtctcgcttcctcagtacctat
gatggagcagagacgctctgcctggaggacatatacacagagaatgtcctggaggtctgggcagatgtgggcatggctgg
atccccgcagaagagcccagccaccctgggcctggaggagctcttcagcaccctggccacctcaatgacgatgcggaca
ctgtgctggtggtgggtgaggcgggcagtggcaagagcacgctcctgcagcggctgcacttgctgtgggctgcagggcaa
gacttccaggaatttctctttgtcttcccattcagctgccggcagctgcagtgcatggccaaaccactctctgtgcggac
tctactctttgagcactgctgttggcctgatgttggtcaagaagacatcttccagttactccttgaccaccctgaccgtg
tcctgttaacctttgatggctttgacgagttcaagttcaggttcacggatcgtgaacgccactgctccccgaccgacccc
acctctgtccagaccctgctcttcaaccttctgcagggcaacctgctgaagaatgcccgcaaggtggtgaccagccgtcc
ggccgctgtgtcggcgttcctcaggaagtacatccgcaccgagttcaacctcaagggcttctctgaacagggcatcgagc
tgtacctgaggaagcgccatcatgagcccggggtggcggaccgcctcatccgcctgctccaagagacctcagccctgcac
ggtttgtgccacctgcctgtcttctcatggatggtgtccaaatgccaccaggaactgttgctgcaggaggggggtccccc
aaagaccactacagatatgtacctgctgattctgcagcattttctgctgcatgccaccccccagactcagcttcccaag
gtctgggacccagtcttcttcggggccgcctcccaccctcctgcacctgggcagactggctctgtggggcctgggcatg
tgctgctacgtgttctcagcccagcagctccaggcagcacaggtcagccctgatgacatttctcttggcttcctggtgcg
tgccaaaggtgtcgtgccagggagtacggcgccctggaattccttcacatcactttccagtgcttctttgccgcgttct
acctggcactcagtgctgatgtgccaccagctttgctcagacacctcttcaattgtggcaggccaggcaactcaccaatg
gccaggctcctgcccacgatgtgcatccaggcctcggagggaaaggacagcagcgtggcagctttgctgcagaaggccga
gccgcacaaccttcagatcacagcagccttcctggcagggctgttgtcccgggagcactggggcctgctggctgagtgcc
agacatctgagaaggccctgctctggcgccaggcctgtgcccgctggtgtctggcccgcagcctccgcaagcacttccac
tccatcccgccagctgcaccgggtgaggccaagagcgtgcatgccatgcccgggttcatctggctcatccggagcctgta
cgagatgcaggaggagcggctggctcggaaggctgcacgtggcctgaatgttgggcacctcaagttgacattttgcagtg
tgggccccactgagtgtgctgccctggcctttgtgctgcagcacctccggcggcccgtggccctgcagctggactacaac
tctgtgggtgacattggcgtggagcagctgctgccttgccttggtgtctgcaaggctctgtatttgcgcgataacaatat
ctcagaccgaggcatctgcaagctcattgaatgtgctcttcactgcgagcaattgcagaagttagctctattcaacaaca
aattgactgacggctgtgcacactccatggctaagctccttgcatgcaggcagaacttcttggcattgaggctggggaat
aactacatcactgccgcgggagcccaagtgctggccgaggggctccgaggcaacacctccttgcagttcctgggattctg
gggcaacagagtgggtgacgaggggcccaggccctggctgaagccttgggtgatcaccagagcttgaggtggctcagcc
tggtggggaacaacattggcagtgtgggtgcccaagccttggcactgatgctggcaaagaacgtcatgctagaagaactc
tgcctggaggagaaccatctccaggatgaaggtgtatgttctctcgcagaaggactgaagaaaaattcaagtttgaaaat
cctgaagttgtccaataactgcatcacctacctaggggcagaagccctcctgcaggcccttgaaaggaatgacaccatcc
tggaagtctggctccgagggaacactttctctctagaggaggttgacaagctcggctgcagggacaccagactcttgctt
tga
```

Figure 26
SEQ ID NO: 59

```
MGEEGGSASHDEEERASVLLGHSPGCEMCSQEAFQAQRSQLVELLVSGSLEGFESVLDWLLSWEVLSWEDYEGFHLLGQP
LSHLARRLLDTVWNKGTWACQKLIAAAQEAQADSQSPKLHGCWDPHSLHPARDLQSHRPAIVRRLHSHVENMLDLAWERG
FVSQYECDEIRLPIFTPSQRARRLLDLATVKANGLAAFLLQHVQELPVPLALPLEAATCKKYMAKLRTTVSAQSRFLSTY
DGAETLCLEDIYTENVLEVWADVGMAGSPQKSPATLGLEELFSTPGHLNDDADTVLVVGEAGSGKSTLLQRLHLLWAAGQ
DFQEFLFVFPFSCRQLQCMAKPLSVRTLLFEHCCWPDVGQEDIFQLLLDHPDRVLLTFDGFDEFKFRFTDRERHCSPTDP
TSVQTLLFNLLQGNLLKNARKVVTSRPAAVSAFLRKYIRTEFNLKGFSEQGIELYLRKRHHEPGVADRLIRLLQETSALH
GLCHLPVFSWMVSKCHQELLLQEGGSPKTTTDMYLLILQHFLLHATPPDSASQGLGPSLLRGRLPTLLHLGRLALWGLGM
CCYVFSAQQLQAAQVSPDDISLGFLVRAKGVVPGSTAPLEFLHITFQCFFAAFYLALSADVPPALLRHLFNCGRPGNSPM
ARLLPTMCIQASEGKDSSVAALLQKAEPHNLQITAAFLAGLLSREHWGLLAECQTSEKALLWRQACARWCLARSLRKHFH
SIPPAAPGEAKSVHAMPGFIWLIRSLYEMQEERLARKAARGLNVGHLKLTFCSVGPTECAALAFVLQHLRRPVALQLDYN
SVGDIGVEQLLPCLGVCKALYLRDNNISDRGICKLIECALHCEQLQKLALFNNKLTDGCAHSMAKLLACRQNFLALRLGN
NYITAAGAQVLAEGLRGNTSLQFLGFWGNRVGDEGAQALAEALGDHQSLRWLSLVGNNIGSVGAQALALMLAKNVMLEEL
CLEENHLQDEGVCSLAEGLKKNSSLKILKLSNNCITYLGAEALLQALERNDTILEVWLRGNTFSLEEVDKLGCRDTRLLL
*
```

Figure 27
SEQ ID NO: 60

```
atgggggaagagggtggttcagcctctcacgatgaggaggaaagagcaagtgtcctcctcggacattctccggggttgtga
aatgtgctcgcaggaggcttttcaggcacagaggagccagctggtcgagctgctggtctcagggtccctggaaggcttcg
agagtgtcctggactggctgctgtcctgggaggtcctctcctggggaggactacgagggcttccacctcctgggccagcct
ctctcccacttggccaggcgccttctggacaccgtctggaataagggtacttgggcctgtcagaagctcatcgcggctgc
ccaagaagcccaggccgacagccagtcccccaagctgcatggctgctgggaccccactcgctccacccagcccgagacc
tgcagagtcaccggccagccattgtcaggaggctccacagccatgtggagaacatgctggacctggcatgggagcgggt
ttcgtcagccagtatgaatgtgatgaaatcaggttgccgatcttcacaccgtcccagagggcaagaaggctgcttgatct
tgccacggtgaaagcgaatggattggctgccttccttctacaacatgttcaggaattaccagtcccattggccctgcctt
tggaagctgccacatgcaagaagtatatggccaagctgaggaccacggtgtctgctcagtctcgcttcctcagtacctat
gatggagcagagacgctctgcctggaggacatatacacagagaatgtcctggaggtctgggcagatgtgggcatggctgg
atccccgcagaagagcccagccaccctgggcctggaggagctcttcagcaccctggccacctcaatgacgatgcggaca
ctgtgctggtggtgggtgaggcgggcagtggcaagagcacgctcctgcagcggctgcacttgctgtgggctgcagggcaa
gacttccaggaatttctctttgtcttcccattcagctgccggcagctgcagtgcatggccaaaccactctctgtgcggac
tctactctttgagcactgctgttggcctgatgttggtcaagaagacatcttccagttactccttgaccaccctgaccgtg
tcctgttaacctttgatggctttgacgagttcaagttcaggttcacggatcgtgaacgccactgctccccgaccgacccc
acctctgtccagaccctgctcttcaaccttctgcagggcaacctgctgaagaatgcccgcaaggtggtgaccagccgtcc
ggccgctgtgtcggcgttcctcaggaagtacatccgcaccgagttcaacctcaagggcttctctgaacagggcatcgagc
tgtacctgaggaagcgccatcatgagcccggggtggcggaccgcctcatccgcctgctccaagagacctcagccctgcac
ggtttgtgccacctgcctgtcttctcatggatggtgtccaaatgccaccaggaactgttgctgcaggaggggggtcccc
aaagaccactacagatatgtacctgctgattctgcagcattttctgctgcatgccacccccccagactcagcttcccaag
gtctgggacccagtcttcttcggggccgcctcccaccctcctgcacctgggcagactggctctgtggggcctgggcatg
tgctgctacgtgttctcagcccagcagctccaggcagcacaggtcagccctgatgacatttctcttggcttcctggtgcg
tgccaaaggtgtcgtgccaggggagtacggcgccctggaattcctcacatcactttccagtgcttctttgccgcgttct
acctggcactcagtgctgatgtgccaccagctttgctcagacacctcttcaattgtggcaggccaggcaactcaccaatg
gccaggctcctgcccacgatgtgcatccaggcctcggagggaaaggacagcagcgtggcagctttgctgcagaaggccga
gccgcacaaccttcagatcacagcagccttcctggcagggctgttgtcccgggagcactggggcctgctggctgagtgcc
agacatctgagaaggccctgctccggcgccaggcctgtgcccgctggtgtctggcccgcagcctccgcaagcacttccac
tccatcccgccagctgcaccgggtgaggccaagagcgtgcatgccatgcccgggttcatctggctcatccggagcctgta
cgagatgcaggaggagcggctggctcggaaggctgcacgtggcctgaatgttgggcacctcaagttgacattttgcagtg
tgggccccactgagtgtgctgccctggcctttgtgctgcagcacctccggcggcccgtggccctgcagctggactacaac
tctgtgggtgacattggcgtggagcagctgctgccttgccttggtgtctgcaaggctctgtatttgcgcgataacaatat
ctcagaccgaggcatctgcaagctcattgaatgtgctcttcactgcgagcaattgcagaagttagctctattcaacaaca
aattgactgacggctgtgcacactccatggctaagctccttgcatgcaggcagaacttcttggcattgaggctggggaat
aactacatcactgccgcgggagcccaagtgctggccgaggggctccgaggcaacacctccttgcagttcctgggattctg
gcgcaacagagtgggtgacgaggggccccaggccctggctgaagccttgggtgatcaccagagcttgaggtggctcagcc
tggtggggaacaacattggcagtgtgggtgcccaagccttggcactgatgctggcaaagaacgtcatgctagaagaactc
tgcctggaggagaaccatctccaggatgaaggtgtatgttctctcgcagaaggactgaagaaaaattcaagtttgaaaat
cctgaagttgtccaataactgcatcacctacctaggggcagaagccctcctgcaggcccttgaaaggaatgacaccatcc
tggaagtctggctccgagggaacactttctctctagaggaggttgacaagctcggctgcagggacaccagactcttgctt
tga
```

Figure 28
SEQ ID NO: 61

```
MGEEGGSASHDEEERASVLLGHSPGCEMCSQEAFQAQRSQLVELLVSGSLEGFESVLDWLLSWEVLSWEDYEGFHLLGQP
LSHLARRLLDTVWNKGTWACQKLIAAAQEAQADSQSPKLHGCWDPHSLHPARDLQSHRPAIVRRLHSHVENMLDLAWERG
FVSQYECDEIRLPIFTPSQRARRLLDLATVKANGLAAFLLQHVQELPVPLALPLEAATCKKYMAKLRTTVSAQSRFLSTY
DGAETLCLEDIYTENVLEVWADVGMAGSPQKSPATLGLEELFSTPGHLNDDADTVLVVGEAGSGKSTLLQRLHLLWAAGQ
DFQEFLFVFPFSCRQLQCMAKPLSVRTLLFEHCCWPDVGQEDIFQLLLDHPDRVLLTFDGFDEFKFRFTDRERHCSPTDP
TSVQTLLFNLLQGNLLKNARKVVTSRPAAVSAFLRKYIRTEFNLKGFSEQGIELYLRKRHHEPGVADRLIRLLQETSALH
GLCHLPVFSWMVSKCHQELLLQEGGSPKTTTDMYLLILQHFLLHATPPDSASQGLGPSLLRGRLPTLLHLGRLALWGLGM
CCYVFSAQQLQAAQVSPDDISLGFLVRAKGVVPGSTAPLEFLHITFQCFFAAFYLALSADVPPALLRHLFNCGRPGNSPM
ARLLPTMCIQASEGKDSSVAALLQKAEPHNLQITAAFLAGLLSREHWGLLAECQTSEKALLRRQACARWCLARSLRKHFH
SIPPAAPGEAKSVHAMPGFIWLIRSLYEMQEERLARKAARGLNVGHLKLTFCSVGPTECAALAFVLQHLRRPVALQLDYN
SVGDIGVEQLLPCLGVCKALYLRDNNISDRGICKLIECALHCEQLQKLALFNNKLTDGCAHSMAKLLACRQNFLALRLGN
NYITAAGAQVLAEGLRGNTSLQFLGFWRNRVGDEGAQALAEALGDHQSLRWLSLVGNNIGSVGAQALALMLAKNVMLEEL
CLEENHLQDEGVCSLAEGLKKNSSLKILKLSNNCITYLGAEALLQALERNDTILEVWLRGNTFSLEEVDKLGCRDTRLLL
*
```

MODULATORS OF NOD2 SIGNALING

This application is a divisional of application Ser. No. 10/314,506, filed Dec. 9, 2002 now U.S. Pat. No. 7,060,442, which is a continuation in part of U.S. patent application Ser. No. 10/014,269, filed Oct. 26, 2001 now U.S. Pat. No. 6,835,815, which claims priority to U.S. provisional patent application Ser. No. 60/244,289, filed Oct. 30, 2000, each of which is herein incorporated by reference in its entirety.

This patent application was supported in part by grant CA-64556 from the National Institutes of Health. The government has certain rights in the invention.

FIELD OF THE INVENTION

The present invention relates to intracellular signaling molecules, in particular the Nod2 protein and nucleic acids encoding the Nod2 protein. The present invention provides methods of identifying modulators of Nod2 signaling. In particular, the present invention additionally provides methods of screening immune modulators such as adjuvants using Nod2. The present invention further provides methods of altering Nod2 signaling.

BACKGROUND OF THE INVENTION

Inflammatory bowel diseases (IBD) are defined by chronic, relapsing intestinal inflammation of obscure origin. IBD refers to two distinct disorders, Crohn's disease and ulcerative colitis (UC). Both diseases appear to involve either a dysregulated immune response to GI tract antigens, a mucosal barrier breach, and/or an adverse inflammatory reaction to a persistent intestinal infection. The GI tract luminal contents and bacteria constantly stimulate the mucosal immune system, and a delicate balance of proinflammatory and anti-inflammatory cells and molecules maintains the integrity of the GI tract, without eliciting severe and damaging inflammation. It is unknown how the IBD inflammatory cascade begins, but constant GI antigen-dependent stimulation of the mucosal and systemic immune systems perpetuates the inflammatory cascade and drives lesion formation.

There is no known cure for IBD, which afflicts 2 million Americans. Current are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+en-vAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. methods of managing IBD symptoms cost an estimated $1.2 billion annually in the United States alone.

In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer. The risk for cancer begins to rise significantly after eight to ten years of IBD.

Some patients with UC only have disease in the rectum (proctitis). Others with UC have disease limited to the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum (proctitis) or UC limited to the end of the left colon (proctosigmoiditis) is better then that of full colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants cause increased risk of infection, renal insufficiency, and the need for hospitalization.

Clearly there is a great need for identification of the molecular basis of IBD, or its associated disorders Crohn's disease and ulcerative colitis.

SUMMARY OF THE INVENTION

The present invention relates to intracellular signaling molecules, in particular the Nod2 protein and nucleic acids encoding the Nod2 protein. The present invention provides methods of identifying modulators of Nod2 signaling. In particular, the present invention additionally provides methods of screening immune modulators such as adjuvants using Nod2. The present invention further provides methods of altering Nod2 signaling.

Accordingly, in some embodiments the present invention provides a method of screening compounds, comprising providing a cell expressing a Nod2 variant, wherein the Nod2 variant is defective in responding to bacterial muropeptides; and a plurality of test compounds; and contacting the cell with the plurality of test compounds; and determining the presence or absence of a response to a bacterial muropeptide. In some embodiments, the response to a bacterial muropeptide comprises the activation of NF-κB. In some embodiments, the activation of NF-κB is detected using a reporter gene assay. In some embodiments, the Nod2 variant is a Crohn's disease associated variant (e.g., including, but not limited to, SEQ ID NOs: 55, 57, 59, and 61). In some embodiments, the cell expressing a Nod2 variant comprises peripheral blood mononuclear cells isolated from an individual diagnosed with Crohn's disease. In some embodiments, the response to a bacterial muropeptide comprises the activation of NF-κB. In some embodiments, the activation of NF-κB is detected using an electrophoretic mobility shift assay. In some embodiments, the test compound is a drug. In some embodiments, the test compound is a muramyl dipeptides (e.g., including, but not limited to, MurNAc-L-Ala-D-isoGln, MuraNac-L-Ala-D-isoGln, MuraNac-L-Ala-D-Glu, analogs of MurNAc-L-Ala-D-isoGln, analogs of MuraNac-L-Ala-D-isoGln, and analogs of MuraNac-L-Ala-D-Glu). In some embodiments, the present invention provides a drug identified by the method.

The present invention also provides a method of screening compounds, comprising providing a cell expressing Nod2; and a plurality of test compounds; and contacting the cell with the plurality of test compounds; and determining the level of Nod2 activity in the cell in response to the test compound. In some embodiments, the Nod2 activity comprises activation of NF-κB. In some embodiments, the activation of NF-κB is detected using a reporter gene assay. In some embodiments, the test compound is a muramyl dipeptides (e.g., including, but not limited to, MurNAc-L-Ala-D-isoGln, MuraNac-L-Ala-D-isoGln, MuraNac-L-Ala-D-Glu, analogs of MurNAc-L-Ala-D-isoGln, analogs of MuraNac-L-Ala-D-isoGln, and analogs of MuraNac-L-Ala-D-Glu). In some embodiments, the test compound is a vaccine adjuvant. In other embodiments, the test compound in an anti-adjuvant. In some embodiments, the Nod2 activity is increased in response to the test compound. In other embodiments, the Nod2 activity is decreased in response to the test compound.

The present invention further provides a method of modulating Nod2 signaling in a subject, comprising providing a compound that is capable of altering a subject's Nod2 activity in response to bacterial muropeptides; and administering the compound to a subject under conditions such that the subject's Nod2 activity is response to bacterial muropeptides is altered. In some embodiments, the subject is diagnosed with Crohn's disease and the compound increases the subjects Nod2 activity is response to bacterial muropeptides. In other embodiments, the compound is a vaccine adjuvant and the compound increases the subjects Nod2 activity is response to bacterial muropeptides. In still further embodiments, the compound is an anti-adjuvant and the compound decreases the subjects Nod2 activity is response to bacterial muropeptides. In some embodiments, the compound is a muramyl dipeptides (e.g., including, but not limited to, MurNAc-L-Ala-D-isoGln, MuraNac-L-Ala-D-isoGln, MuraNac-L-Ala-D-Glu, analogs of MurNAc-L-Ala-D-isoGin, analogs of MuraNac-L-Ala-D-isoGln, and analogs of MuraNac-L-Ala-D-Glu). In some embodiments, the method further comprises the step of determining the presence or absence of a variant Nod2 allele (e.g., including, but not limited to, SEQ ID NOs: 33, 54, 56, 58, and 60) in the subject diagnosed with Crohn's disease.

DESCRIPTION OF THE FIGURES

FIG. 1A shows the amino acid sequence of Nod2 (SEQ ID NO:4). Caspase recruitment domains (CARD 1 and 2; SEQ ID NOs: 5 and 6), nucleotide binding domain (NBD; SEQ ID NO:7) and leucine-rich repeats (LRRS; SEQ ID NOs:8-17) are indicated by reverse highlight, underline and arrows, respectively. The consensus sequence of the P-loop (Walker A box; SEQ ID NO: 18) and the $Mg^{2+}$ binding site (Walker B box; SEQ ID NO: 19) are indicated by boxes. FIG. 1B shows the domain structure of Nod2. Numbers corresponds to amino acid residues shown in panel A. The region homologous to the CARDS, NBD and LRRs are indicated by black closed, dark closed, and hatched boxes, respectively.

FIG. 2 shows an alignment of Human Nod2 and Related Proteins. FIG. 1A shows an alignment of CARDs of Nod2

(SEQ ID NOs:5 and 6), Nod1 (GeneBank accession number AF113925; SEQ ID NO:20), RICK (AF027706; SEQ ID NO:21), ARC (AF043244; SEQ ID NO:22), RAIDD (U79115; SEQ ID NO:23), Caspase-2 (U13021; SEQ ID NO:24), Ced-3 (L29052; SEQ ID NO:25), Ced-4 (X69016; SEQ ID NO:26), Caspase-9 (U56390; SEQ ID NO:27), Apaf-I (AF013263; SEQ ID NO:28) and c-IAP-1 (L49431; SEQ ID NO:29). Hydrophobic residues are shown in reverse highlighting. Negatively and positively charged residues are highlighted in light and dark gray, respectively. Proline and glycine residues ((αβ breaker) are bolded. The putative (αhelices, H1 to H5, are shown according to the three dimensional structure of the CARD of RAIDD (Chou et al., Cell, 94:171 [1998]). FIG. 2B shows an alignment of NBDs of Nod2 (SEQ ID NO:7), Nod1 (SEQ ID NO:30), Apaf-I (SEQ ID NO:31) and Ced-4 (SEQ ID NO:32). The residues identical and similar to those of Nod2 are shown by reverse and dark highlighting, respectively. The consensus sequence of the P-loop (Walker A box) and the $Mg^{2+}$ binding site (Walker B box) are indicated by boxes. The residues identical and similar to those of Nod2 are shown by reverse and dark highlighting, respectively. FIG. 2C shows an alignment of LRRs of Nod2 (SEQ ID NOs: 8-17). The conserved positions with leucine and other hydrophobic residues are indicated by dark and light gray highlighting, respectively. The putative (α helix and β sheet are shown according to the three dimensional structure of the ribonuclease inhibitor (Kobe and Deisenhofer, Curr. Opin. Struct Biol., 5:409-416 [1995]).

FIG. 3A shows a northern blot analysis of nod2 expression in human tissues; PBL (peripheral blood leukocytes). FIG. 3B shows RT-PCR analysis of nod2 expression in granulocyte, monocyte and lymphocyte enriched populations. Two sets of Nod2 oligonucleotide primers (P1-P2 and P3-P4) were used to amplify the nucleotide sequences of the CARDs and LRRs, respectively. FIG. 3C shows the nucleotide sequence of the 5' region of Nod2. Two potential in-frame translation initiation sites separated by 81 nucleotides are indicated by arrows. FIG. 3D shows immunoblotting of nod2 gene products expressed in HEK293T cells. Cells were transfected with control plasmid (lane 1), or constructs containing both potential translation initiator sites of Nod2 (lane 2), or as a control the second translation initiation site corresponding to that of Nod2b (lane 3) or the most NH2-terminal translation initiation site (lane 4) in the context of a canonical translation initiation motif. In all cases, a Nod2 protein lacking residues 302-1040 and HA tagged at its COOH terminus was expressed to facilitate detection of nod2 gene products. Nod2 proteins were detected by immunoblotting with anti-HA antibody and indicated by a and b.

FIG. 4A shows wt and mutant Nod2 proteins. CARDs, NBD and LRRs are indicated by black closed, dark closed, and hatched boxes, respectively. Numbers represent amino acid residue in Nod2 protein. FIG. 4B shows expression analysis of wt and mutant Nod2 proteins. HEK293T cells were transfected with control plasmid (–) or 5 µg of plasmids producing the indicated HA-tagged Nod2 proteins. Extracts from equal number of cells were immunoprecipitated with rabbit anti-HA antibody and immunoblotted with mouse monoclonal anti-HA antibody. The expected size of CARDs, CARD1 and LRRs mutant proteins are indicated by black arrowheads. FIG. 4C shows NF-κB activation by Nod2 proteins. Induction of NF-κB activation was determined from triplicate culture of HEK293T cells co-transfected with the indicated amount of wt or mutant Nod2 expression plasmids in the presence of pBVIx-Luc and pEF-BOS-β-gal as described below. Values represent mean ±SD of triplicate cultures.

FIG. 5A shows inhibition of Nod2 and TNFα-induced NF-KB activation by dominant negative mutant proteins of the NF-κB pathway. Induction of NF-κB activation was determined in triplicate cultures of HEK293T cells transfected with 30 ng of Nod2 plasmid (open bars) or stimulated with 10 ng/ml of TNFα for 4 h (closed bars) and 70 ng of I-κBα S32A/S36A, IKKα K44A, IKKβ K44A, RICK (406-540) or RIP (558-671) expression plasmid in the presence of pBVIx-Luc and pEF-BOS-β-gal. Results are presented as a percent of values obtained with Nod2 and control plasmid. In the experiment shown, Nod2 and TNFα induced 58±8-fold and 14±1-fold activation of NF-κB, respectively. Values represent mean ±SD of triplicate cultures. FIG. 5B shows induction of NF-κB in parental Rat-1 and derivative 5R cells. Induction of NF-κB activation was determined from triplicate cultures of I×10⁵ HEK293T cells co-transfected with the indicated plasmids and pBVIx-Luc in the presence of control plasmid pEF-BOS-β-gal. Values represent mean ±SD of triplicate cultures.

FIGS. 6A and B show the interaction between wt and mutant Nod2 with RICK. HEK293T cells were co-transfected with wt or mutant Nod2 and RICK expression plasmid. The co-immunoprecipitated RICK was detected by immunoblotting with anti-Flag antibody (upper panel). Nod2 immunoprecipitates are shown in lower panel. Total lysates were blotted with anti-Flag antibody (middle panel). FIG. 6C shows the interaction between Nod2 and wt and mutant RICK. HEK293T cells were co-transfected with wt Nod2 and wt or mutant RICK-ΔCARD (residues 1-374) or RICK-CARD (residues 374540) expression plasmid. The co-immunoprecipitated Nod2 was detected by immunoblotting with anti-HA antibody (upper panel). Total lysates were blotted with anti-Flag (middle panel) or anti-HA (lower panel) antibody. A background band is shown by asterisk.

FIG. 7A shows an expression analysis of wt and mutant Fpk3-Nod2 chimeric proteins. HEK293T cells were transfected with of control plasmid (–) or plasmids producing the indicated Myc-tagged Fpk3Nod2 proteins. Extracts from equal number of cells were immunoprecipitated and immunoblotted with rabbit anti-Myc antibody. FIG. 7B shows that enforced oligomerization of Nod2 induces NF-κB activation. 2×10⁵ HEK293T cells were transfected with 1 ng of the indicated plasmids in the presence of pBVIx-luc and pEF-BOS-β-gal. 8 hr post-transfection, cells were treated with 500 nM AP1510 (black bars) or left untreated (white bars). 24 hr post-transfection, the κB-dependent transcription was determined as described below. Values represent mean ±SD of triplicate cultures.

FIG. 8A shows data from 1×10⁵ HEK293T cells that were transfected with 0.3 ng of pcDNA3-Flag (white bars) or pcDNA3Nod1-Flag (black bars) in the presence of 600 ng of pcDNA3, 73 ng pEFIBOS-βgal and 7.3 ng pBXIV-luc. 8 hr post-transfection, cells were treated with 10 µg/ml of each pathogen product, lipoteichoic acid (LTA) or peptidoglycan (PGN) from *Staphylococcus aureus*, lipopolysaccharide (LPS) from *Escherichia coli* 055:B5, mannan from *Candida albicans* 20A, synthetic soluble bacterial lipoprotein (SBLP) or left untreated (Control). 24 hr post-transfection, κB-dependent transcription was determined by luciferase activity relative and values normalized to β-galactosidase in triplicate cultures. As control, the inset showed Nod1 proteins immunodetected with anti-FLAG Ab in lysates from cells transfected with 10 ng pcDNA3-Nod1 in presence (right) and absence (left) of 10 µg/ml LPS. FIG. 8B shows data from 1×10$^5$ HEK293T cells that were transfected with 0.3 ng of pcDNA3-Flag (−), pcDNA3-Nod1-Flag (Nod1) or pcDNA3-Nod1(I-648)-Flag (Nod1ΔLRR), 300 ng pcDNA3-FLAG-TLR4, 3 ng pCMVIL1R1 plus 100 ng pcDNA3-IL1β-HA (IL1) or I ng pcDNA3-RIP-Flag (RIP) in the presence of 600 ng of pcDNA3, 73 ng pEF 1BOS-βgal and 7.3 ng pBXIV-luc. Eight hr post-transfection, cells were treated with 10 µg/n-A LPS (black bars) or left untreated (white bars). Twenty-four hr post-transfection, κB-dependent transcription was determined as described above.

FIG. 10A shows S100 lysate from transfected cells was incubated with [$^3$H] LPS, anti-FLAG M2 Ab, Protein A-Sepharose and Protein G-Sepharose. FIG. 10B shows data for proteins that were immunopurified first from 20 mg of S100 lysate and incubated with [$^3$H] LPS in the presence of 10 mg BSA. The co-imunoprecipitated radioactivity was determined as described in detail below. Expression of each protein in 50 µg of S100 lysate was immunodetected with anti-FLAG Ab.

FIG. 11 shows the nucleic acid sequence of SEQ ID NO:33.

FIG. 12 shows the nucleic acid sequence of SEQ ID NO:1.

FIG. 13 shows the polypeptide sequence of SEQ ID NO:2.

FIG. 14 shows the polypeptide sequence of SEQ ID NO:3.

FIG. 15 shows the polypeptide sequence of SEQ ID NO:34.

FIG. 16 shows the nucleic acid (SEQ ID NOs: 35 (wild type) and 36 (mutant)) and polypeptide (SEQ ID NO:51 (wild type) and SEQ ID NO:52 (mutant)) of Nod2 Exon 11.

FIG. 17 shows recognition of peptidoglycans by NOD2. FIG. 17A shows that NOD2 and TLR4 recognize different bacterial components. FIG. 17B shows activation of NF-κB by cells stimulated with gel-filtration fractions of PGN from *B. subtilis* digested or undigested with Mutanolysin.

FIG. 18 shows stimulation of NOD2 by synthetic muropeptides. FIG. 18A shows a schematic representation of synthetic muropeptide structures used in the study. FIG. 18B shows the ability of HEK293T cells transfected with 66 ng pMX-puro-NOD2 (NOD2) or vector control (−) and reporter pBxIV-luc and pEF-BOS-β-gal plasmids to activate NF-κB. FIG. 18C shows the ability of MDP and its analogs MurNAc-L-Ala-L-isoGln (LL) and MurNAc-D-Ala-D-isoGln (DD) at 100 ng/ml to stimulate NF-κB activation in the presence of NOD2 or control plasmid (−). FIG. 18D shows the ability of MDP (100 ng/ml) and sBLP (1000 ng/ml) to activate NF-κB.

FIG. 20A shows representative DNA analysis from normal donors (WT) and Crohn's disease patient carrying the L1007fs mutation in one (heterozygous, HT) or both (homozygous, HM) alleles. FIG. 20B shows PBMNC stimulated with 1 µg/ml of LPS from *Salmonella typhimurium* (L), 10 ng/ml of MDP (M) for 1 hour or left untreated. FIG. 20C shows an analysis of nuclear extracts for the presence of NF-κB binding activity by EMSA. FIGS. 20C and D show PBMNC analyzed for expression of IL-1β (C) and A1 (D) transcripts by quantitative RT-PCR.

FIG. 21 shows the nucleic acid sequence of SEQ ID NO: 54.

FIG. 22 shows the amino acid sequence of SEQ ID NO: 55.

FIG. 23 shows the nucleic acid sequence of SEQ ID NO: 56.

FIG. 24 shows the amino acid sequence of SEQ ID NO: 57.

FIG. 25 shows the nucleic acid sequence of SEQ ID NO: 58.

FIG. 26 shows the nucleic acid sequence of SEQ ID NO: 59.

FIG. 27 shows the nucleic acid sequence of SEQ ID NO: 60.

FIG. 28 shows the amino acid sequence of SEQ ID NO: 61.

GENERAL DESCRIPTION OF THE INVENTION

Figure 1:
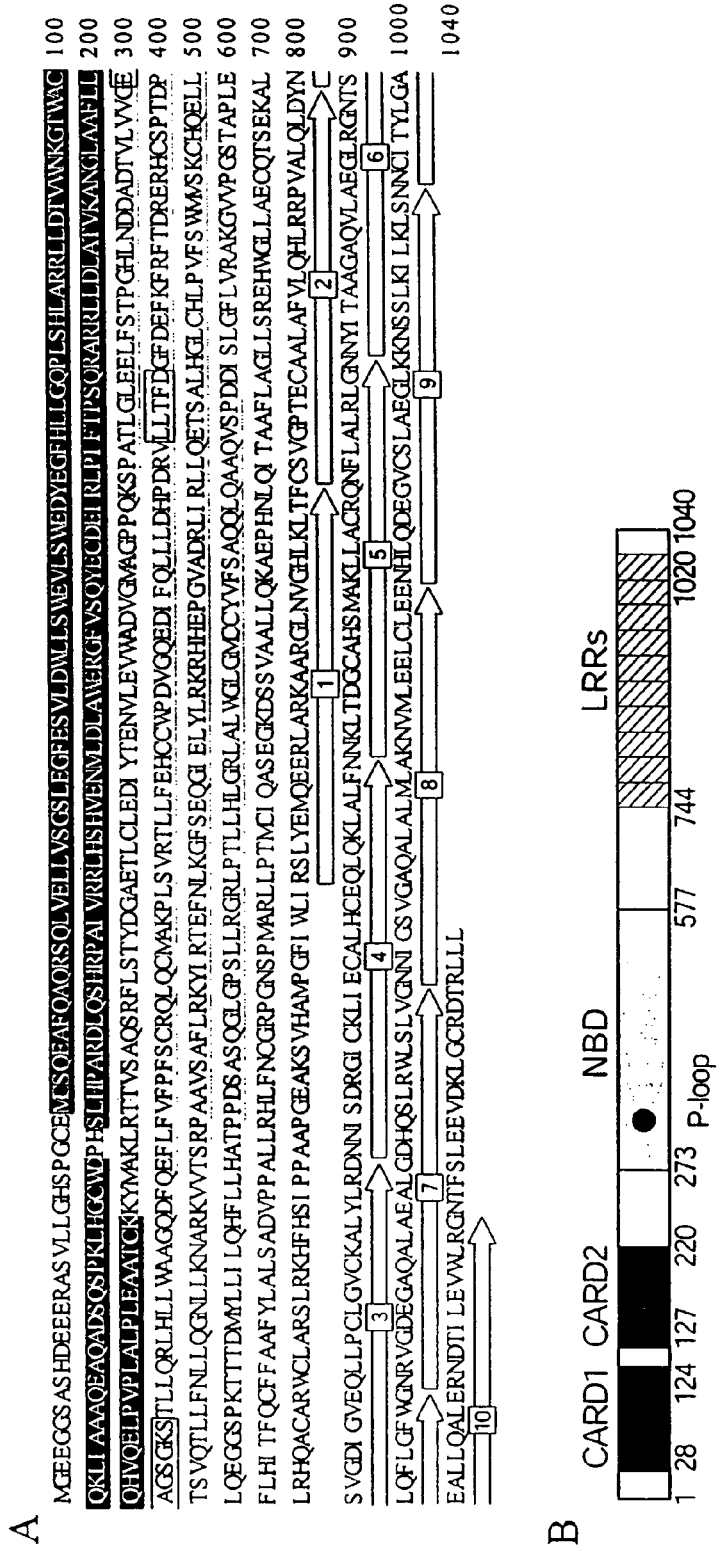
FIG. 1 shows the deduced Amino Acid Sequence and Domain Structure of Human Nod2.

The present invention relates to intracellular signaling molecules, in particular the Nod2 protein and nucleic acids encoding the Nod2 protein. The Nod2 protein was found to have structural homology to the Nod1 protein. Apaf-1 and Nod1 (also called CARD4) are members of a family of intracellular proteins that are composed of an NH2-terminal caspase-recruitment domain (CARD), a centrally located nucleotide-binding domain (NBD) and a COOH-terminal regulatory domain (Bertin et al., J. Biol. Chem. 274: 12955-12958 [1999], Inohara et al., J. Biol. Chem. 274: 14560-14568 [1999]). While Apaf-1 possesses WD40 repeats, Nod1 contains leucine-rich repeats (LRRs) in its C-terminus. The structural and functional similarities between Apaf-1 and Nod1 suggest that these proteins share a common molecular mechanism for activation and effector function. In the case of Apaf-1, the WD-40 repeats act as a recognition domain for mitochondrial damage through binding to cytochrome c, allowing Apaf-1 to oligomerize and interact with procaspase-9 through a CARD-CARD homophilic interaction (Li et al., Cell 91: 479-489 [1997], Zou et al., J. Bio. Chem. 274: 11549-11556 [1999]). Apaf-1 oligomerization is mediated by the NBD and is thought to induce the proximity and proteolytic activation of procaspase-9 molecules in the apoptosome complex (Srinivasula et al., Mol. Cell 1: 949-957 [1998], Hu et al., J. Bio. Chem. 273: 33489-34494 [1998]).

Previous studies showed that Nod1 promotes apoptosis when overexpressed in cells, but unlike Apaf-1, it induces NF-κB activation (Bertin et al., supra, Inohara et al., supra). NF-κB activation induced by Nod1 is mediated by the association of the CARD of Nod1 with the corresponding CARD of RICK (also called RIP2 and CARDIAK), a protein kinase that activates NF-κB (Bertin et al., supra, Inohara et al., supra, Inohara et al., J. Biol. Chem. 273: 12296-12300 [1998], McCarthy et al., J. Bio. Chem. 273, 16968-16975 [1998], Thome et al., Curr. Biol. 8: 885-888 [1998]). Analyses with wild-type (wt) and mutant forms of both Nod1 and RICK have suggested that Nod1 and RICK act in the same pathway of NF-κB activation, where RICK functions as a downstream mediator of Nod1 signaling (Bertin et al., supra, Inohara et al., [1999] supra, Inohara et al., J. Biol. Chem. 275: 27823-27831 [2000]). Nod1 self-associates through its NBD and Nod1 oligomerization promotes proximity of RICK molecules and NF-κB activation (Inohara et al., [2000], supra). Nod1 also displays striking similarity to a class of disease resistance (R) proteins found in plants (Pamiske et al., Cell 91: 821-832 [1997], Dixon et al., Proc. Natl. Acad. Sci. U. S. A. 97: 8807-8814 [2000]). Like Nod1, these intracellular R proteins contain N-terminal effector domains linked to a NBD and share with Nod1 the presence of multiple LRRs located C-terminally of the NBD (Bertin et al., supra, Dixon et al., supra). After specific recognition of pathogen products, these R proteins mediate a defense response associated with metabolic alterations and localized cell death at the site of pathogen invasion (Dixon et al., supra). The LRRs of R proteins are highly diverse and appear to be involved in the recognition of a wide array of pathogen components (Parniske et al., supra, Dixon et al., supra). The binding partner of the LRRs of Nod1 remains unknown. The structural homology of Nod1 with plant R proteins suggest that other LRR-containing Nod1-like molecules may exist in the human genome to allow activation of these molecules by different sets of intracellular stimuli.

The identification and characterization of Nod2, a LRR-containing protein with structural and functional similarity to Nod1 is disclosed herein. These studies indicate that Nod2 activates NF-κB, but unlike Nod1, this new homologue is primarily expressed in monocytes. The present invention is not limited to any particular mechanism of action. Indeed, an understanding of the mechanism of action is not necessary to practice the present invention. Nevertheless, Nod2 is a member of the Nod1/Apaf-I family that activates NF-κB through interactions with its $NH_2$-terminal CARDS, as these domains were necessary and sufficient for NF-κB activation. Nod2 associated with RICK via a homophilic CARD-CARD interaction. The NF-κB-inducing activity of Nod2 correlated with its ability to associate with RICK and was inhibited by a RICK mutant, suggesting that RICK is a direct downstream target of Nod2. Thus, the signaling pathways of both Nod1 and Nod2 appear to utilize RICK as a downstream mediator of NF-κB activation. In contrast to Nod1, two tandem CARDs are present in the $NH_2$-terminus of Nod2 and both were required for association with RICK and NF-κB activation.

Nod2 is the first molecule known to contain two CARDS. The molecular basis underlying the requirement of both CARDs of Nod2 for RICK binding remains unclear. The present invention is not limited to any particular mechanism of action. Indeed, an understanding of the mechanism of action is not necessary to practice the present invention. Nevertheless, it is contemplated that the presence of both CARDs may enhance the affinity for the CARD of RICK. Another possibility is that upon an initial interaction involving a CARD of Nod2 and the CARD of RICK, Nod2 may undergo a conformational change that allows the second CARD to associate with high affinity to RICK. The intermediate region of RICK associates with IKKγ (Inohara et al., [2000], supra), providing a direct link between Nod1/Nod2 and the IKK complex. Consistent with this model, NF-κB activation induced by Nod2 as well as that induced by Nod I required IKKγ and was inhibited by dominant negative forms of IKKγ, IKKα and IKKβ. The functional role for the LRRs of Nod1 and Nod2 remains unclear. The LRR is a repeated protein-protein interaction module that is presumably involved in the activation of Nod1 and Nod2 by upstream signals. In the case of plant NBD/LRR-containing R proteins, their LRRs appear to be important for the recognition of pathogen components and their N-terminal domains appear to mediate a signaling cascade that regulates gene expression (Parniske et al., supra, Dixon et al., supra). Because both Nod1 and Nod2 activate NF-κB, their LRRs may act to recognize a different set of intracellular stimuli that mediate Nod1 and Nod2 oligomerization and association with RICK. Nod2 is expressed in monocytes, dendritic cells, and paneth cells in the gut (Gutierrez et al., J Biol Chem 277(44):41701-5 [2002]). Because Nod2 is expressed in monocytes, Nod2 might serve as an intracellular receptor that transduces signals in the monocyte/macrophage that lead to activation of NF-κB and transcription of regulatory genes.

The Nod2 proteins of the present invention are also involved in the recognition of microbial pathogens. The innate immune system regulates the immediate response to microbial pathogens in multiple organisms including humans. The innate immune response is initiated by recognition of specific pathogen components by host immune cells. Mammalian cells have cell surface receptors and intracellular mechanisms that initiate the defense response against microbial pathogens (Aderem and Ulevitch, Nature, 406:785-787 [2000]; Philpott et al., J. Immunol., 165:903-914 [2000]). Toll like receptors (TLRs) comprise a family of cell surface receptors that are related to the Drosophila Toll protein, a molecule involved in defense against fungal infection in the fly (Aderem and Ulevitch, Supra). Ten mammalian TLRs have been identified (Aderem and Ulevitch, Supra). Two members of the family, TLR2 and TLR4, have been better characterized and shown to mediate the response to multiple bacterial cell-wall components including lipopolysaccharide (LPS), lipopeptides, peptidoglycans (PGN) and lipoteichoic acid (LTA) (Yang et al., Nature, 395:284-288 [1998]; Poltorak et al., Science, 282:2085-2088 [1998]; Aliprantis et al., Science, 285:736-739 [1999]; Chow et al., J. Biol. Chem., 274:10689-10692 [2000]; and Schwandner et al., J. Biol. Chem., 274: 17406-17409 [2000]). Mammalian TLRs have multiple leucine-rich repeats in the ectodomain and an intracellular Toll-IL1 receptor (TIR) domain that mediates a signaling cascade to the nucleus (Aderem and Ulevitch, Supra). Stimulation of TLR2 and TLR4 leads to the recruitment of the adaptor molecule MyD88 and the serine kinase IL-1R-associated kinase (IRAK), two signaling components that together with TRAF-6 mediate activation of NF-κB (Aderem and Ulevitch, Supra).

Plants have several classes of genes that regulate the defense against invading pathogens. An important class of these molecules is termed disease resistance (R) proteins, and members include both membrane-bound and cytosolic proteins. These are essential for the defense against multiple pathogens including bacteria, fungi and viruses (Dixon et al., PNAS, 97:8807-8814 [2000]). The cytosolic type of R proteins which include the Tobacco N gene product and up to 200 gene products in *Arabinopsis thaliana* are comprised of an N-terminal TIR or zinc finger effector domain, a centrally located nucleotide-binding domain (NBD) and C-terminal leucine-rich repeats (LRRs) (Dixon et al., Supra). The LRRs of cytosolic R proteins are highly diverse and appear to be involved in the recognition of a wide array of microbial components (Dixon et al., Supra). This class of disease resistant proteins mediates the hypersensitive (HS) response in plants that includes metabolic alterations and localized cell death at the site of pathogen invasion (Dixon et al., Supra). The cytosolic R proteins of plants have remarkable structural homology to Nod1/CARD4, a recently described protein related to the apoptosis regulator Apaf-1 (Zou et al., Cell, 90:405-413 [1997]; Bertin et al., J. Biol. Chem., 274:12955-12958; and Inohara et al., J. Biol. Chem., 274:14560-14568 [1999]). Like plant R proteins, Nod1 is comprised of an N-terminal effector domain, a centrally located NBD and multiple LRRs at the C-terminus (Bertin et al., Supra; Inohara et al., Supra). Nod1 induces NF-κB activation which is mediated through the association of its N-terminal caspase-recruitment domain (CARD) with that of RICK, a protein kinase that also activates NF-κB (Bertin et al., Supra; Inohara et al., Supra; Inohara et al., J. Biol. Chem., 273:12296-12300 [1998]; McCarthyetal., J. Biol. Chem., 273:16968-16975; Thome et al., Curr. Biol., 8:885-888 [1998]; Inohara et al., J. biol. Chem., 275:27823-27831 [2000]). However, the trigger molecule(s) which activates Nod1 to mediate NF-κB activation remains unknown.

The present invention also demonstrates that lipopolysaccharide (LPS) induces NF-κB activation in HEK293T cell expressing Nod1, whereas parental HEK293Tcells are insensitive to LPS. The present invention is not limited to a particular mechanism of action. Indeed, an understanding of the mechanism of action is not necessary to practice the present invention. Nevertheless, in the human system, the TLR4/MD2/CD14 complex has been demonstrated to serve as a surface receptor for LPS (Aderem and Ulevitch, Supra). In addition to the cell surface TLR4 complex, there is mounting evidence that mammalian cells have an intracellular receptor that detects LPS in the cytoplasm of bacteria infected cells (Philpott et al., Supra). For example, epithelial cells are unresponsive to extracellular LPS either purified or presented in the context of non-invasive Gram negative bacterial strains (Philpott et al., Supra). Yet, LPS introduced inside of the epithelial cells activates NF-κB (Philpott et al., Supra). However, to date, the identification of an intracellular recognition system for LPS and/or other microbial products remains elusive. Nod1 is involved in the recognition of peptidoglycan fragments. Nod1 function might be important in the intracellular response of epithelial cells against invading bacteria, as Nod1 is expressed in intestinal, lung and nasal epithelial surfaces in the late mouse embryo (Inohara et al., Supra). The presence of an intracellular detection system for bacterial LPS would be expected in epithelial surfaces such as those of the gut that are highly exposed to bacteria and bacterial products. In such organs, triggering of an inflammatory response to bacterial products through surface receptors such as TLR4 would be detrimental to the organism. HEK293T cells expressing Nod2, another member of Nod family, respond to LPS but Nod1 and Nod2 appear to have different preferences for LPS preparations from different bacteria. These observations suggest that in addition to TLRs, Nod family members may represent another innate immune system for the recognition of a wide array of pathogen products. For example, the genome of the plant *Arabidopsis thaliana* contains approximately 200 disease resistance genes encoding intracellular NBD-LRR proteins related to Nod1 and Nod2 (Dixon et al., Supra).

Three genetic variants within the coding region of NOD2, L1007fsinsC, G908R, and R702W, have been genetically associated with susceptibility to Crohn's disease in European and American populations (Hugot et al., Nature 411: 599 (2001); Ogura et al., Nature 411:603 (2001); Hampe et al., Lancet 357:1925 (2001); Ahmad et al., Gastroenterology 122:854 (2002)). NOD2 has been shown to recognize preparations of lipopolysaccharides (LPS) and peptidoglycan (PGN) through its COOH terminal LRRs (Inohara et al., J. Biol. Chem. 276:2551 [2001]), and this activity is deficient in the disease-associated variants (Ogura et al., [2001], supra). However, the precise bacterial structure recognized by NOD2 remains unknown. Experiments conducted during the course of development of the present invention (See e.g., Example 9) identified muramyl dipeptide derived from peptidoglycan as the essential structure in bacteria recognized by NOD2. Peripheral blood mononuclear cells from individuals homozygous for the major disease-associated L1007fsinsC NOD2 mutation responded to lipopolysaccharide but not to synthetic muramyl dipeptide.

The present invention is not limited to a particular mechanism. Indeed, an understanding of the mechanism of the present invention is not necessary to practice the present invention. Nonetheless, it is contemplated that the lack of response to MDP in apparently normal individuals suggest that the presence of certain bacteria in the intestine and/or additional genetic factors may be required for clinical disease. MDP is the minimal essential structure of bacterial peptidoglycan required for biological effects including activity in Freund's complete adjuvant (H. Takada, S. Kotani, *In The Theory and Practical Application of Adjuvants*, D. E. S. Stewart, Ed., (Wiley, Chichester, England, 1995), pp. 171-202). MDP has been shown to signal through TLR2 and TLR4-independent mechanisms (Yang et al., Infect. Immun. 69:2045 [2001]; Wolfert et al., J. Biol. Chem. 277:39179 [2002]), but the host recognition system for MDP has not been identified. The present invention is not limited to a particular mechanism. Indeed, an understanding of the mechanism is not neccessary to understand the present invention. Nonetheless, it is contemplated that experiments described herein support the conclusion that Nod2 mediates the recognition of MDP in mammalian cells. Macrophages contain intracellular hydrolases, which digest bacterial PGN and release PGN fragments including GlcNAc-MurNAc-dipeptide (Johnnsen et al., Am. J. Physiol. 260:R126 [1991]; Vermeulen et al., Infect. Immun. 46:476 [1984]). These muropeptides derived from intracellular and/or phagocytosed bacteria as well as PGN fragments released during bacterial growth are available for recognition by Nod2. The synthetic MDP and GlcNAc-MurNAc-dipeptides mimicking the natural muropeptides induced Nod2-dependent activation of NF-κB. Thus, it is contemplated that Nod2 is activated by muropeptides derived from bacteria in vivo. This observation provides a role for Nod2 in both inflammatory responses in Crohn's disease and vaccine and adjuvant function (e.g., by stimulating immune system function in response to adjuvants).

Crohn's disease associated Nod2 variants and PBMNC from individuals homozygous for L1007fsinsC are defective in their response to muramyl dipeptide. This result is consistent with the observation that homozygocity for L1007fsinsC is important for susceptibility to Crohn's disease. Because activation of NF-$_\kappa$B in response to bacterial components mediates protection of the host against pathogens, it is contemplated that Nod2-mediated susceptibility to disease is caused by a failure to trigger a protective NF-$_\kappa$B pathway in response to muropeptides.

Such a defective response against certain bacterial products may result secondarily in the diffuse activation of NF-$_\kappa$B found in intestinal tissue by Nod2-independent mechanisms. Accordingly, in some embodiments, the present invention provides methods of screening for compounds that restore the activity against bacterial muropeptides. The present invention further provides pharmaceuticals identified by such screening methods. It is contemplated that therapeutics that restore activity against bacterial muropeptides are beneficial to Crohn's disease patients harboring Nod2 mutations.

Definitions

To facilitate understanding of the invention, a number of terms are defined below.

As used herein, the term "Nod2" when used in reference to a protein or nucleic acid refers to a protein or nucleic acid encoding a protein that, in its wild type form, activates NF-$_\kappa$B and contains two CARDs (caspase recruitment domains). The term Nod2 encompasses both proteins that are identical to wild-type Nod2 and those that are derived from wild type Nod2 (e.g., variants of Nod2 or chimeric genes constructed with portions of Nod2 coding regions).

As used herein, the term "activates NF-κB," when used in reference to any molecule that activates NF-κB, refers to a molecule (e.g., a protein) that induces the activity of the NF-κB transcription factor through a cell signaling pathway. Assays for determining if a molecule activates NF-κB utilize, for example, NF-κB responsive reporter gene constructs. Suitable assays include, but are not limited to, those described in Examples 4 and 5.

As used herein, the term "activity of Nod2" refers to any activity of wild type Nod2. The term is intended to encompass all activities of Nod2 (e.g., including, but not limited to, activating NF-κB, binding to RICK, and enhancing apoptosis).

The term "apoptosis" means non-necrotic cell death that takes place in metazoan animal cells following activation of an intrinsic cell suicide program. Apoptosis is a normal process in the development and homeostasis of metazoan animals. Apoptosis involves characteristic morphological and biochemical changes, including cell shrinkage, zeiosis, or blebbing, of the plasma membrane, and nuclear collapse and fragmentation of the nuclear chromatin, at intranucleosomal sites, due to activation of an endogenous nuclease.

As used herein, the term "symptoms of Crohn's disease" refers to symptoms associated with Crohn's disease, including, but not limited to abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding).

The phrase "under conditions such that symptoms of Crohn's disease are reduced" refers to a qualitative or quantitative reduction in detectable symptoms (e.g., "symptoms of Crohn's disease"), including but not limited to a detectable impact on the rate of recovery from disease (e.g., rate of weight gain).

As used herein, the term "adjuvants" refers to a compound used to increase the immunological response (e.g., to a vaccine or for the generation of antibodies in non-human animals). Adjuvants include, but are not limited to, depending on the host species, Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, BCG (Bacille Calmette-Guerin) and *Corynebacterium parvum*).

As used herein, the term "anti-adjuvant" refers to a compound that inhibit adjuvant activity. In some embodiments, anti-adjuvants inhibit Nod2 signaling that has been enhanced by an adjuvant compound such as MDP or MDP analogs. In some embodiments, anti-adjuvants are used to reduce side effects of an adjuvant such as fever or inflammation.

The term "gene" refers to a nucleic acid (e.g., DNA) sequence that comprises coding sequences necessary for the production of a polypeptide or precursor (e.g., Nod2). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "Nod2 gene" refers to the full-length Nod2 nucleotide sequence (e.g., contained in SEQ ID NO: 1). However, it is also intended that the term encompass fragments of the Nod2 sequence, as well as other domains within the full-length Nod2 nucleotide sequence. Furthermore, the terms "Nod2 nucleotide sequence" or "Nod2 polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The-term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5× SSPE, 0.1% SDS at 42° C. when a probe of about 500 nucleotides in length is employed.

The following terms are used to describe the sequence relationships between two or more polynucleotides: "reference, sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., Nod2).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having-aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions(claimed in the present invention) with its various ligands and/or substrates.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands.

The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding Nod2 includes, by way of example, such nucleic acid in cells ordinarily expressing Nod2 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

As used herein, the term "purified" or "to purify" refers to the removal of contaminants from a sample. For example, Nod2 antibodies are purified by removal of contaminating non-immunoglobulin proteins; they are also purified by the removal of 15 immunoglobulin that does not bind Nod2. The removal of non-immunoglobulin proteins and/or the removal of immunoglobulins that do not bind Nod2 results in an increase in the percent of Nod2-reactive immunoglobulins in the sample. In another example, recombinant Nod2 polypeptides are expressed in bacterial host cells and the polypeptides are purified by the removal of host cell proteins; the percent of recombinant Nod2 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of m-RNA present in the band corresponding in size to the correctly spliced Nod2 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding Nod2 (e.g., SEQ ID NO:1) or fragments thereof may be employed as hybridization probes. In this case, the Nod2 encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TKs) which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity. Tyrosine kinases can also be cytoplasmic, non-receptor-type enzymes and act as a downstream component of a signal transduction pathway.

As used herein, the term "signal transduction protein" refers to proteins that are activated or otherwise effected by ligand binding to a membrane receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249-257 [1995]). Typically, GPCRs contain seven transmembrane domains. Putative GPCRs can be identified on the basis of sequence homology to known GPCRs.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydrolyses GTP, and a dimeric βγ subunit. In the basal, inactive state, the G-protein exists as a heterotrimer of the α and βγ subunits. When the G-protein is inactive, guanosine diphosphate (GDP) is associated with the a subunit of the G-protein. When a GPCR is bound and activated by a ligand, the GPCR binds to the G-protein heterotrimer and decreases the affinity of the Gα subunit for GDP. In its active state, the G subunit exchanges GDP for guanine triphosphate (GTP) and active Gα subunit disassociates from both the receptor and the dimeric βγ subunit. The disassociated, active Gα subunit transduces signals to effectors that are "downstream" in the G-protein signalling pathway within the cell. Eventually, the G-protein's endogenous GTPase activity returns active G subunit to its inactive state, in which it is associated with GDP and the dimeric βγ subunit.

Numerous members of the heterotrimeric G-protein family have been cloned, including more than 20 genes encoding various Gα subunits. The various G subunits have been categorized into four families, on the basis of amino acid sequences and functional homology. These four families are termed $G\alpha_s$, $G\alpha_i$, $G\alpha_q$, and $G\alpha_{12}$. Functionally, these four families differ with respect to the intracellular signaling pathways that they activate and the GPCR to which they couple.

For example, certain GPCRs normally couple with $G\alpha_s$ and, through $G\alpha_s$, these GPCRs stimulate adenylyl cyclase activity. Other GPCRs normally couple with $GG\alpha_q$, and through $GG\alpha_q$, these GPCRs can activate phospholipase C (PLC), such as the β isoform of phospholipase C (i.e., PLCβ, Stermweis and Smrcka, Trends in Biochem. Sci. 17:502-506 [1992]).

As used herein, the term "nucleic acid binding protein" refers to proteins that bind to nucleic acid, and in particular to proteins that cause increased (i.e., activators or transcription factors) or decreased (i.e., inhibitors) transcription from a gene.

As used herein, the term "ion channel protein" refers to proteins that control the ingress or egress of ions across cell membranes. Examples of ion channel proteins include, but are not limited to, the $Na^+$-$K^+$ ATPase pump, the $Ca^{2+}$ pump, and the $K^+$ leak channel.

As used herein, the term "protein kinase" refers to proteins that catalyze the addition of a phosphate group from a nucleoside triphosphate to an amino acid side chain in a protein. Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250-300 amino acid catalytic domain. This domain can be further divided into 11 subdomains. N-terminal subdomains I-IV fold into a two-lobed structure which binds and orients the ATP donor molecule, and subdomain V spans the two lobes. C-terminal subdomains VI-XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (See, e.g., Carbonneau, H. and Tonks, Annu. Rev. Cell Biol. 8:463-93 [1992]). Regulation of PTK activity may therefore be an important strategy in controlling some types of cancer.

As used herein, the term "protein phosphatase" refers to proteins that remove a phosphate group from a protein. Protein phosphatases are generally divided into two groups, receptor and non-receptor type proteins. Most receptor-type protein tyrosine phosphatases contain two conserved catalytic domains, each of which encompasses a segment of 240 amino acid residues. (See, e.g., Saito et al., Cell Growth and Diff. 2:59-65 [1991]). Receptor protein tyrosine phosphatases can be subclassified further based upon the amino acid sequence diversity of their extracellular domains. (See, e.g., Krueger et al., Proc. Natl. Acad. Sci. USA 89:7417-7421 [1992]).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos.,6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

DETAILED DESCRIPTION OF THE INVENTION

The present invention relates to intracellular signaling molecules, in particular the Nod2 protein and nucleic acids encoding the Nod2 protein. The present invention encompasses both native and recombinant wild-type forms of Nod2, as well as mutant and variant forms, some of which possess altered characteristics relative to the wild-type Nod2. The present invention also relates to methods of using Nod2, including altered expression in transgenic organisms and expression in prokaryotes and cell culture systems. The present invention also encompasses methods for screening for drugs that inhibit or potentiate Nod2 action. The present invention also relates to methods for screening for susceptibility to intestinal bowel disease and Crohn's disease. The present invention additionally provides methods of treating Crohn's disease (e.g., using compounds identified with the drug screening methods of the present invention).

I. Nod2 Polynucleotides

As described above, a new family of proteins that activate NF-κB have been discovered. This family was identified by screening public databases for nucleic acid sequences having homology to Nod1. Accordingly, the present invention provides nucleic acids encoding Nod2 genes, homologs, and variants (e.g., mutations and polyporphisms (e.g., SEQ ID NOs: 1 and 33). In some embodiments, the present invention provide polynucleotide sequences that are capable of hybridizing to SEQ ID NOs:1 and 33 under conditions of low to high stringency as long as the polynucleotide sequence capable of hybridizing encodes a protein that retains a biological activity of the naturally occurring Nod2. In some embodiments, the protein that retains a biological activity of naturally occurring Nod2 is 70% homologous to wild-type Nod2, preferably 80% homologous to wild-type Nod2, more preferably 90% homologous to wild-type Nod2, and most preferably 95% homologous to wild-type Nod2. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, alleles of Nod2 are provided. In preferred embodiments, alleles result from a polymorphism or mutation, (i.e., a change in the nucleic acid sequence) and generally produce altered mRNAs or polypeptides whose structure or function may or may not be altered. Any given gene may have none, one or many allelic forms. Common mutational changes which give rise to alleles are generally ascribed to deletions, additions or substitutions of nucleic acids. Each of these types of changes may occur alone, or in combination with the others, and at the rate of one or more times in a given sequence. Examples of the alleles of the present invention include those encoded by (SEQ ID NOs:1 and 33; wild-type and Crohn's disease mutant alleles, respectively).

In some embodiments of the present invention, the nucleic acids encode two CARD domains corresponding (e.g., nucleic acid sequences encoding the peptides SEQ ID NOs: 5 and 6). In other embodiments, the nucleic acids encode at least one domain selected from the group consisting of an NBD domain (e.g., SEQ ID NO:7), an LRR domain (e.g., SEQ ID NOs: 8-17), and P-loop and $Mg^{2+}$ binding domains (SEQ ID NO:18-19)

In still other embodiments of the present invention, the nucleotide sequences of the present invention may be engineered in order to alter an Nod2 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of Nod2 may be extended utilizing nucleotide sequences (e.g., SEQ ID NOS:1 and 33) in various methods known in the art to detect upstream sequences such as promoters and regulatory elements. For example, it is contemplated that restriction-site polymerase chain reaction (PCR) will find use in the present invention. This is a direct method which uses universal primers to retrieve unknown sequence adjacent to a known locus (Gobinda et al., PCR Methods Applic.; 2:318-22 [1993]). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0.(National Biosciences Inc, Plymouth Minn.), or another appropriate program, to be 22-30 nucleotides in length, to have a GC content of 50% or more, and to anneal to the target sequence at temperatures about 68-72° C. The method-uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also,: random primed libraries -are preferred, in that they will contain more sequences which contain the 5' and upstream gene regions. A randomly primed library may be particularly useful in case where an oligo d(T) library does not yield full-length. cDNA. Genomic mammalian libraries are useful for obtaining introns and extending 5' sequence.

In other embodiments of the present invention, variants of the disclosed Nod2 sequences are provided. In preferred embodiments, variants result from polymorphisms or mutations, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., Nod2 function) for such purposes as increasing binding affinity of the Nod2 for RICK. Such modified peptides are considered functional equivalents of peptides having an activity of Nod2 as defined herein. A modified peptide can be produced in which the nucleotide sequence-encoding the polypeptide has been altered, such as by substitution, deletion, or addition. In particularly preferred embodiments, these modifications do not significantly reduce the synthetic activity of the modified Nod2. In other words, construct "X" can be evaluated in order to determine whether it is a member of the genus of modified or variant Nod2's of the present invention as defined functionally, rather than structurally. In preferred embodiments, the activity of a variant Nod2 is evaluated by the methods described in Example 4. Accordingly, in some embodiments, the present invention provides nucleic acids encoding a Nod2 that activates NF-κB (e.g., activates an inflammatory response). In preferred embodiments, the activity of a Nod2 variant is evaluated by transfecting HEK293T cells with and expression construct encoding the variant Nod2. In particularly preferred embodiments, the cells contain a reporter luciferase construct containing enhancer regions that are responsive to NF-κB. In other embodiments, the Nod2 variant may be capable of binding a protein (e.g., RICK) but not activating NF-κB. These variants can be screened for by the immunoprecipitation methods described in Example 6.

Moreover, as described above, variant forms of Nod2 are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of Nod2 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur -containing (cysteine and methionine) (e.g., Stryer ed., *Biochemistry, pg*. 17-21, 2nd ed, W H Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a Nod2 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. Nod2 Polypeptides

In other embodiments, the present invention provides Nod2 polynucleotide sequences that encode Nod2 polypeptide sequences. Nod2 polypeptides (e.g., SEQ ID NOs:2-3) are described in FIGS. 13 and 14. Other embodiments of the present invention provide fragments, fusion proteins or functional equivalents of these Nod2 proteins. In still other embodiment of the present invention, nucleic acid sequences corresponding to Nod2 variants, homologs, and mutants may be used to generate recombinant DNA molecules that direct the expression of the Nod2 variants, homologs and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO:1 which encode substantially the same or a functionally equivalent amino acid sequence, may be used to clone and express Nod2. In general, such polynucleotide sequences hybridize to SEQ ID NO: 1 under conditions of high to medium stringency as described above. As will be understood by those of skill in the art, it may be advantageous to produce Nod2-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of Nod2 expression or to produce recombinant RNA transcripts having desirable properties, such as a longer half-life, than transcripts produced from naturally occurring sequence.

1. Vectors for Production of Nod2

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOS:1 and 33). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO:1) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large-numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of Nod2

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of Nod2

The present invention also provides methods for recovering and purifying Nod2 from recombinant cell cultures including, but-not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOs: 1 and 33) fused in frame to a marker sequence which allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence-may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of Nod2

In addition, the present invention provides fragments of Nod2 (i.e., truncation mutants, e.g., SEQ ID NO:3). In some embodiments of the present invention, when expression of a portion of the Nod2 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751-757 [1987]) and *Salmonella typhimurium* and its in vitro activity has been demonstrated on recombinant proteins (Miller et al., Proc. Natl. Acad. Sci. USA 84:2718-1722 [1990]). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP.

5. Fusion Proteins Containing Nod2

The present invention also provides fusion proteins incorporating all or part of Nod2. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a Nod2 protein. In some embodiments of the present invention, the VP6 capsid protein of rotavirus is used as an immunologic carrier protein for portions of the Nod2 polypeptide, either in the monomeric form or in the form of a viral particle. In other embodiments of the present invention, the nucleic acid sequences corresponding to the portion of Nod2 against which antibodies are to be raised can be incorporated into a fusion gene construct which includes coding sequences for a late vaccinia virus structural protein to produce a set of recombinant viruses expressing fusion proteins comprising a portion of Nod2 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of Nod2 and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of Nod2 is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the Nod2 proteins can also be expressed and presented by bacterial cells.

In addition to utilizing fusion proteins to enhance immunogenicity, it is widely appreciated that fusion proteins can also facilitate the expression of proteins, such as the Nod2 protein of the present invention. Accordingly, in some embodiments of the present invention, Nod2 can be generated as a glutathione-S-transferase (i.e., GST fusion protein). It is contemplated that such GST fusion proteins will enable easy purification of Nod2, such as by the use of glutathione-derivatized matrices (See e.g, Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of Nod2, can allow purification of the expressed Nod2 fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of Nod2

Still other embodiments of the present invention provide mutant or variant forms of Nod2 (i.e., muteins). It is possible to modify the structure of a peptide having an activity of Nod2 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject Nod2 proteins as defined herein. A modified peptide can be produced in which the amino acid sequence has been altered, such as by amino acid substitution, deletion, or addition.

Moreover, as described above, variant forms (e.g., mutants or polymorphic sequences) of the subject Nod2 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present Nod2 proteins, as well as truncation mutants, and is especially useful for identifying potential variant sequences (i.e., mutants or polymorphic sequences) that are functional in binding to NF-κB or proteins in the NF-κB signalling pathway and signalling an inflammatory response. The purpose of screening such combinatorial libraries is to generate, for example, novel Nod2 variants which can act as either agonists or antagonists, or alternatively, possess novel activities all together.

Therefore, in some embodiments of the present invention, Nod2 variants are engineered by the present method to provide more efficient activation of NF-κB (i.e., generating an inflammatory response). In other embodiments of the present invention, combinatorially-derived homologs are generated which have a selective potency relative to a naturally occurring Nod2. Such proteins, when expressed from recombinant DNA constructs, can be used in gene therapy protocols.

Still other embodiments of the present invention provide Nod2 variants which have intracellular half-lives dramatically different than the corresponding wild-type protein. For example, the altered protein can be rendered either more stable or less stable to proteolytic degradation or other cellular process which result in destruction of, or otherwise inactivate Nod2. Such variants, and the genes which encode them, can be utilized to alter the location of Nod2 expression by modulating the half-life of the protein. For instance, a short half-life can give rise to more transient Nod2 biological effects and, when part of an inducible expression system, can allow tighter control of Nod2 levels within the cell. As above, such proteins, and particularly their recombinant nucleic acid constructs, can be used in gene therapy protocols.

In still other embodiments of the present invention, Nod2 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of Nod2 variants or other related proteins are aligned, preferably to promote the highest homology possible. Such a population of variants can include, for example, Nod2 homologs from one or more species, or Nod2 variants from the same species but which differ due to mutation. Amino acids which appear at each position of the aligned sequences are selected to create a degenerate set of combinatorial sequences.

In a preferred embodiment of the present invention, the combinatorial Nod2 library is produced by way of a degenerate library of genes encoding a library of polypeptides which each include at least a portion of potential Nod2 protein sequences. For example, a mixture of synthetic oligonucleotides can be enzymatically ligated into gene sequences such that the degenerate set of potential Nod2 sequences are expressible as individual polypeptides, or alternatively, as a set of larger fusion proteins (e.g., for phage display) containing the set of Nod2 sequences therein.

There are many ways by which the library of potential Nod2 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Nod2 sequences. The synthesis of degenerate oligonucleotides is well known in the art (See e.g., Narang, Tetrahedron Lett., 39:3 9 [1983]; Itakura et al., Recombinant DNA, in Walton (ed.), *Proceedings of the* 3rd *Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386-390 [1980]; Roberts et al., Proc. Natl. Acad. Sci. USA 89:2429-2433 [1992]; Devlin et al., Science 249: 404-406 [1990]; Cwirla et al., Proc. Natl. Acad. Sci. USA 87: 6378-6382 [1990]; as well as U.S. Pat.

Nos. 5,223,409, 5,198,346, and 5,096,815, each of which is incorporated herein by reference).

It is contemplated that the Nod2 nucleic acids (e.g., SEQ ID NO: 1, and fragments and variants thereof) can be utilized as starting nucleic acids for directed evolution. These techniques can be utilized to develop Nod2 variants having desirable properties such as increased or decreased binding affinity for RICK.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung et al., Technique, 1:11-15 [1989]; Eckert and Kunkel, PCR Methods Appl., 1: 17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity (e.g., screened for Nod2 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324-25 [1994]; U.S. Pat. Nos. 5,837,458; 5,830,721; 5,811, 238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398-91 [1994]; Stemmer, Proc. Natl. Acad. Sci. USA, 91, 10747-51 [1994]; Crameri et al., Nat. Biotech., 14:315-19 [1996]; Zhang et al., Proc. Natl. Acad. Sci. USA, 94:4504-09 [1997]; and Crameri et al., Nat. Biotech., 15:436-38 [1997]). Variants produced by directed evolution can be screened for Nod2 activity by the methods described in Examples 4-8.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of Nod2 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of Nod2

In an alternate embodiment of the invention, the coding sequence of Nod2 is synthesized, whole or in part, using chemical methods well known in the art (See e.g., Caruthers et al., Nucl. Acids Res. Symp. Ser., 7:215-233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807-2817 [1981]). In other embodiments of the present invention, the protein itself is produced using chemical methods to synthesize either an entire Nod2 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202-204 [1995]) and automated synthesis may be achieved, for example, using ABI 431A Peptide Synthesizer (Perkin Elmer) in accordance with the instructions provided by the manufacturer. Additionally, the amino, acid:sequence of Nod2, or any part thereof, may be altered during direct synthesis and/or combined using chemical methods with other sequences to produce a variant polypeptide.

III. Detection of Nod2 Alleles

Figure 4:
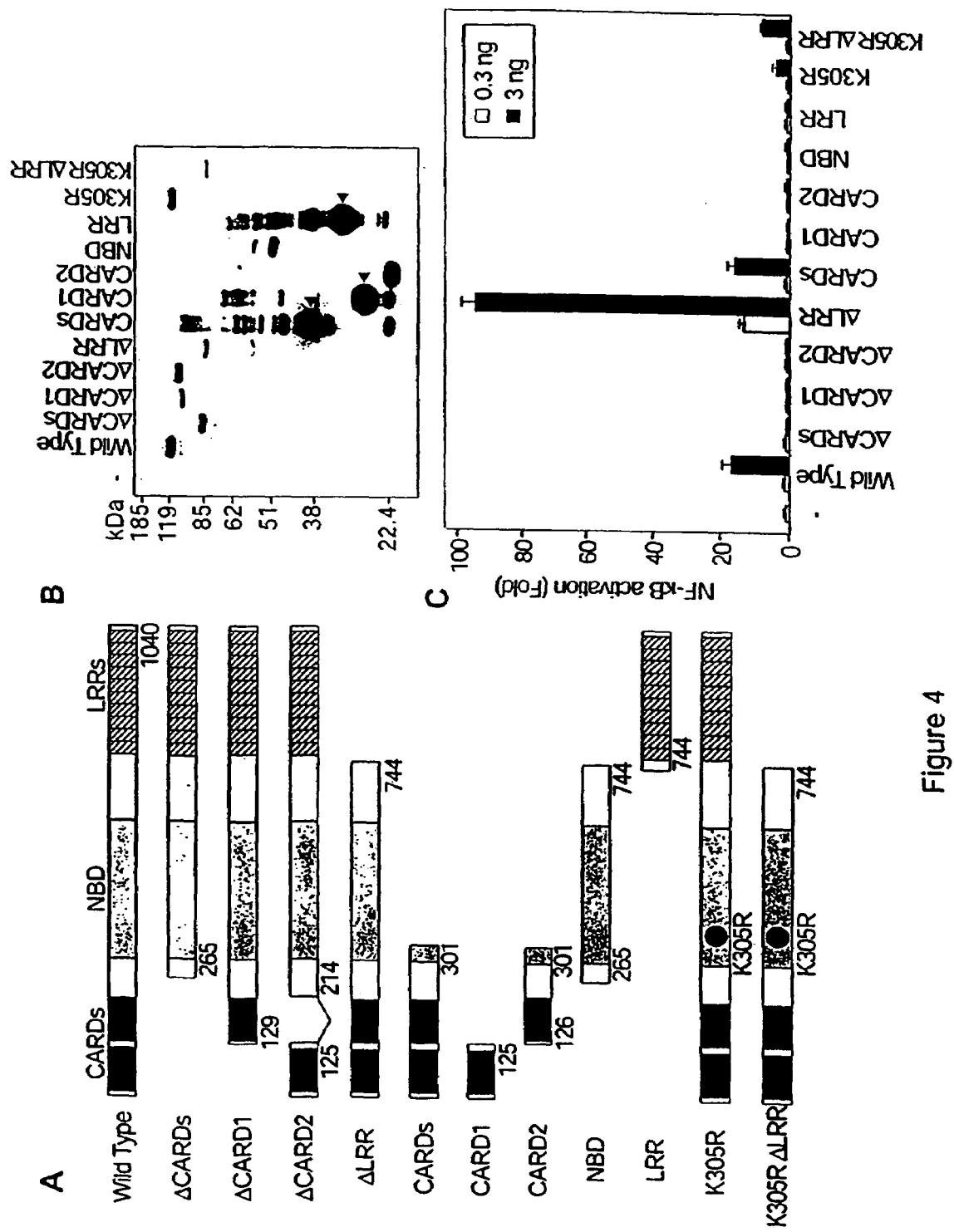
FIG. 4 shows mutational Analysis of Nod2.

In some embodiments, the present invention includes alleles of Nod2 that increase a patient's susceptibility to Crohn's disease (e.g., including, but not limited to, SEQ ID NOs: 33 and 3). Analysis of naturally occurring human Nod2 alleles revealed that patients with increased susceptibility to Crohn's disease have a mutant Nod2 allele that, for example, contains an additional cytosine residue. The additional cytosine residue causes a frameshift mutation resulting in the generation of a stop codon that causes deletion of much of the LRR domain. The resulting protein functions similarly to deletion mutant ΔLRR (See FIG. 4). This deletion mutant exhibits a high degree of NF-κB activation in the absence of other signalling stimuli. However, the present invention is not limited to the mutation described in SEQ ID NOs: 3 and 33. Any mutation that results in the undesired phenotype (e.g., a high degree of NF-κB activation in the absence of other signalling stimuli) is within the scope of the present invention. Assays for determining if a given polypeptide has such activities-are provided in Examples 4 and 5.

The present invention is not limited to a particular mechanism of action. Indeed, an understanding of the mechanism of action is not necessary to practice the present invention. Nevertheless, it is contemplated that the signaling system of which Nod2 is a component recognizes bacterial and viral pathogens and initiates a response to kill the pathogen or infected cell (i.e., cell signalling that activates a transcription factor, that in turn, activates an inflammatory response). It is contemplated that in Crohn's disease the activation of the signalling pathway occurs in the absence of pathogen stimulation because of the presence of the truncated form of Nod2. This leads to the inflammation associated with Crohn's disease.

Accordingly, the present invention provides methods for determining whether a patient has an increased susceptibility to inflammatory bowel disease or Crohn's disease by determining whether the individual has a variant Nod2 gene. In other embodiments, the present invention provides methods for providing:a prognosis-.of increased risk for Crohn's disease to an individual based on the presence or absence of one or more variant alleles of Nod2. In preferred embodiments, the variation causes a truncation of the LRR domain. In other preferred embodiments, the variation results in increased activation of NF-κB and consequent inflammatory response. In particularly preferred embodiments, the variation is single nucleotide polymorphism caused by an insertion of a cytosine residue.

A number of methods are available for analysis of variant (e.g., mutant or polymorphic) nucleic acid sequences. Assays for detections variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of Nod2 (e.g., to the region of polymorphism or mutation). Both sets of primers are used to amplify a sample of DNA. If only the mutant primers result in a PCR product, then the patient has the mutant Nod2 allele. If only the wild-type primers result in a PCR product, then the patient has the wild type allele of Nod2.

3. Fragment Length Polymorphism Assays

In some embodiments of the present invention, variant sequence are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

4. Hybridization Assays

In preferred embodiments of the present invention, variant, sequences are detected a hybridization assay. In a hybridization assay, the presence of absence of a given SNP or mutation is determined based on the ability of the DNA from the sample to hybridize to a complementary DNA molecule (e.g, a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labelled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labelled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so-on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, genomic profiles are generated using a assay that detects hybridization by enzymatic cleavage of specific structures (INVADER assay, Third Wave Technologies; See e.g., U.S. Pat. Nos. 5,846,717; 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/ mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive: and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLI-TAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are: detected using the SNP-IT primer extension assay (Orchid Biosciences, Princeton, N.J.; See e.g., U.S. Pat. Nos. 5,952,174 and 5,919,626, each of which is herein incorporated-by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labelled antibody specific for biotin).

5. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

6. Variant Analysis by Differential Antibody Binding

In other embodiments of the present invention, antibodies (See below for antibody production) are used to determine if an individual contains an allele encoding a variant Nod2 gene. In preferred embodiments, antibodies are utilized that discriminate between mutant (i.e., truncated proteins); and wild-type proteins (SEQ ID NOs:2 and 3). In some particularly preferred embodiments, the antibodies are directed to the C-terminus of Nod2.

7. Kits for Analyzing Risk of Crohn's Disease

The present invention also provides kits for determining whether an individual contains a wild-type or variant (e.g., polymorphic or mutant) allele of Nod2. In some embodiments, the kits are useful determining whether the subject is at risk of developing Crohn's disease. The diagnostic kits are produced in a variety of ways. In some embodiments, the kits contain at least one reagent for specifically detecting a mutant Nod2 allele or protein. In preferred embodiments, the kits contains reagents for detecting a SNP caused by an insertion of a cytosine residue into the wild-type gene. In preferred embodiments, the reagent is a nucleic acid that hybridizes to nucleic acids containing the SNP and that does not bind to nucleic acids that do not contain the SNP. In other preferred embodiments, the reagents are primers for amplifying the region of DNA containing the SNP. In still other embodiments, the reagents are antibodies which preferentially bind either the wild-type or truncated Nod2 proteins. In some embodiments, the kit contains instructions for determining whether the subject is at risk for developing Crohn's disease. In preferred embodiments, the instructions specify that risk for developing Crohn's disease is determined by detecting the presence or absence of a mutant Nod2 allele in the subject, wherein subjects having an allele containing a cytosine insertion mutation have an increased risk of developing Crohn's disease. In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test in some embodiments, the kits also preferably include a positive control sample.

IV. Generation of Nod2 Antibodies

Antibodies can be generated to allow for the detection of Nod2 protein. The antibodies may be prepared using various immunogens. In one embodiment, the immunogen is a human Nod2 peptide to generate antibodies that recognize human Nod2. Such antibodies include, but are not limited to polyclonal, monoclonal, chimeric, single chain, Fab fragments, and Fab expression libraries.

Various procedures known in the art may be used for the production of polyclonal antibodies directed against Nod2. For the production of antibody, various host animals can be immunized by injection with the peptide corresponding to the Nod2 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward Nod2, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing Nod2 specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for Nod2.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of Nod2 (e.g., for Western blotting), measuring levels thereof in appropriate biological samples, etc. The antibodies can be used to detect Nod2 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human Nod2 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of Nod2 detected by immunoblotting (Western blotting). Inumunoblotting techniques are generally more effective with antibodies generated against a peptide corresponding to an epitope of a protein, and hence, are particularly suited to the present invention.

Another method uses antibodies as agents: to alter signal transduction. Specific antibodies that bind to the binding domains of Nod2 or other proteins involved in intracellular signalling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NF-κB. Such antibodies can also be used diagnostically to measure abnormal expression of Nod2, or the aberrant formation of protein complexes, which may be indicative of a disease state.

V. Gene Therapy Using Nod2

The present invention also provides methods and compositions suitable for gene therapy to alter Nod2 expression, production, or function. As described above, the present invention provides human Nod2 genes and provides methods of obtaining Nod2 genes from other species. Thus, the methods described below are generally applicable across many species. In some embodiments, it is contemplated that the gene therapy is performed by providing a subject with a wild-type allele of Nod2 (i.e., an allele that does contain a cytosine insertion mutation). Subjects in need of such therapy are identified by the methods described above. As described above, Nod2 is primarily expressed in the monocytes. Accordingly, a preferred method of gene therapy is to ablate the subjects monocytes (e.g., via radiation) and replace the defective monocytes with monocytes expressing wild-type Nod2 via a bone marrow transplant. In some embodiments, the subjects defective monocytes may be harvested prior to radiation treatment, transfected with a vector (described below) encoding wild-type monocytes, amplified through in vitro cultured, and reintroduced into the subject.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917, [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of :interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931),.peptides derived from DNA binding proteins (e.g., WO96/25508), or a cationic polymer. (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963-967 [1992]; Wu and Wu, J. Biol. Chem., 263:14621-14624 [1988]; and Williams et al., Proc. Natl. Acad. Sci. USA 88:2726-2730 [1991]). Receptor-mediated DNA delivery approaches can also be used,(Curiel et. al., Hum. Gene Ther., 3:147-154 [1992]; and Wu and Wu, J. Biol. Chem., 262:4429-4432 [1987]).

VI. Transgenic Animals Expressing Exogenous Nod2 Genes and Homologs, Mutants, and Variants Thereof The present invention contemplates the generation of transgenic animals comprising an exogenous Nod2 gene or homologs, mutants, or variants thereof. In preferred embodiments, the transgenic animal displays an altered phenotype as compared to wild-type animals. In some embodiments, the altered phenotype is the overexpression of mRNA for a Nod2 gene as compared to wild-type levels of Nod2 expression. In other embodiments, the altered phenotype is the decreased expression of mRNA for an endogenous Nod2 gene as compared to wild-type levels of endogenous Nod2 expression. Methods for analyzing the presence or absence of such phenotypes include Northern blotting, mRNA protection assays, and RT-PCR. In other embodiments, the transgenic mice have a knock out mutation of the Nod2 gene. In still further embodiments, expression of a Nod2 variant gene (e.g., SEQ ID NO:33 (the c insertion mutant) or mutants containing deletions of one or more LRR repeats). In preferred embodiments, the transgenic animals display a Crohn's disease phenotype.

The transgenic animals of the present invention find use in dietary and drug screens. In some embodiments, the transgenic animals (e.g., animals displaying a Crohn's disease phenotype) are fed test or control diets and the response of the animals to the diets is evaluated. In other embodiments, test compounds (e.g., a drug that is suspected of being useful to treat Crohn's disease) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260-1264 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927-693 [1985]). Transfection is-easily and efficiently obtained by culturing the blastomeres on a monolayer of virus-producing cells (Van der Putten, supra; Stewart, et al., EMBO J., 6:383-388 [1987]). Alternatively, infection can be performed at a later stage. Virus or virus-producing cells can be injected into the blastocoele (D. Jahner et al., Nature 298:623-628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner et al, supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154-156 [1981]; Bradley et al., Nature 309:255-258 [1984]; Gossler et al., Proc. Acad. Sci. USA 83:9065-9069 [1986]; and Robertson et al., Nature 322:445-448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468-1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., mutants in which the LRRs of Nod2 are deleted). Methods for homologous recombination are described in U.S. Pat. No. 5,614,396, incorporated herein by reference.

VII. Transgenic Plants Expressing Exogenous Nod2 and Homologs, Mutants, and Variants Thereof As described above, Nod2 share homology with a class of plant disease R gene products. The present invention provides transgenic plants and methods for creating transgenic plants that have altered responses and or resistance to pathogens. In some embodiments, the transgenic plants express an exogenous Nod2 gene or homolog, mutant or variant thereof (e.g., SEQ ID NOs: 1 and 33). In preferred embodiments, the transgenic plant displays an altered phenotype as compared to wild-type plants. In some embodiments, the altered phenotype is the overexpression of mRNA for a Nod2 gene as compared to wild-type levels of Nod2 expression. In other embodiments, the altered phenotype is the decreased expression of mRNA for an endogenous Nod2 gene as compared to wild-type levels of endogenous Nod2 expression. Methods for analyzing the presence or absence of such phenotypes include Northern blotting, mRNA protection assays, and RT-PCR. In still further embodiments, increased Nod2 gene expression in the transgenic plant confers increased resistance to pathogens. In some embodiments, the observed phenotype mimics the inflammatory response induced by Nod2 in animals. Transgenic plants expressing this phenotype may be screened by challenging plants with a pathogen and selecting plants that display resistance as compared to control, nontransgenic plants.

In some embodiments of the present invention, vectors are provided for the transfection of plant hosts to create transgenic plants. In general, these vectors comprise a Nod2 nucleic acid (e.g., SEQ ID NOs:1 and 33).operably linked-to a promoter and other regulatory sequences (e.g., enhancers, polyadenylation signals, etc.) required for expression in a plant. The Nod2 nucleic acid can be oriented to produce sense or antisense transcripts, depending on the desired use. In some embodiments, the promoter is a constitutive promoter (e.g., superpromoter or SD promoter). In other embodiments, the promoter is a seed specific promoter (e.g., phaseolin promoter [See e.g., U.S. Pat. No. 5,589,616, incorporated herein by reference], napin promoter [See e.g., U.S. Pat. No. 5,608,152, incorporated herein by reference], or acyl-CoA carrier protein promoter [See e.g., 5,767,363, incorporated herein by reference]).

In some preferred embodiments, the vector is adapted for use in an *Agrobacterium* mediated transfection process (See e.g., U.S. Pat. Nos.5,981,839; 6,051,757; 5,981,840; 5,824, 877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

It may be desirable to target the nucleic acid sequence of interest to a particular locus on the plant genome. Site-directed integration of-the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

The nucleic acids of the present invention may, also be utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted Nod2 polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

Alternatively, vectors can be constructed for expression in hosts other than plants (e.g., prokaryotic cells such as *E. coli*, yeast cells, *C. elegans*, and mammalian cell culture cells). In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). Large numbers of suitable vectors that are replicable and viable in the host are known to those of skill in the art, and are commercially available. Any other plasmid or vector may be used as long as they are replicable and viable in the host.

In some preferred embodiments of the present invention, bacterial expression vectors comprise an origin of replication, a suitable promoter and optionally an enhancer, and also any necessary ribosome binding sites, polyadenylation sites, transcriptional termination sequences, and 5' flanking nontranscribed sequences. Promoters useful in the present invention include, but are not limited to, retroviral LTRs, SV40 promoter, CMV promoter, RSV promoter, *E. coli* lac or trp promoters, phage lambda $P_L$ and $P_R$ promoters, T3, SP6 and T7 promoters. In other embodiments of the present invention, recombinant expression vectors include origins of replication and selectable markers, (e.g., tetracycline or ampicillin resistance in *E. coli*, or neomycin phosphotransferase gene for selection in eukaryotic cells).

The vectors described above can be utilized to express the Nod2 of the present invention in transgenic plants. A variety of methods are known for producing transgenic plants.

In some embodiments, *Agrobacterium* mediated transfection is utilized to create transgenic plants. Since most dicotyledonous plant are natural hosts for *Agrobacterium*, almost every dicotyledonous plant may be transformed by *Agrobacterium* in vitro. Although monocotyledonous plants, and in particular, cereals and grasses, are not natural hosts to *Agrobacterium*, work to transform them using *Agrobacterium* has also been carried out (Hooykas-Van Slogteren et al., Nature 311:763-764 [1984]). Plant genera that may be transformed by *Agrobacterium* include *Arabidopsis, Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus* and *Pisum*.

For transformation with *Agrobacterium*, disarmed *Agrobacterium* cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference). The nucleic acid sequence of interest is then stably integrated into the plant genome by infection with the transformed *Agrobacterium* strain. For example, heterologous nucleic acid sequences have been introduced into plant tissues using the natural DNA transfer system of *Agrobacterium tumefaciens* and *Agrobacterium rhizogenes* bacteria (for review, see Klee et al., Ann. Rev. Plant Phys. 38:467-486 [1987]).

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be transformed by *Agrobacterium* and (b) that the transformed cells or tissues can be induced to regenerate into whole plants. The third method is transformation of seeds, apices or meristems with *Agrobacterium*. This method requires micropropagation.

One of skill in the art knows that the efficiency of transformation by *Agrobacterium* may be enhanced by using a number of methods known in the art. For example, the inclusion of a natural wound response molecule such as acetosyringone (AS) to the *Agrobacterium* culture has been shown: to enhance transformation efficiency with *Agrobacterium tumefaciens* [Shahla et al., Plant Molec. Biol. 8:291-298 [1987]). Alternatively, transformation efficiency may be enhanced by wounding the target tissue to be transformed. Wounding of plant tissue may be achieved, for example, by punching, maceration, bombardment with microprojectiles, etc. [See e.g., Bidney et al., Plant Molec. Biol. 18:301-313 [1992]).

In still further embodiments, the plant cells are transfected with vectors via particle bombardment (i.e., with a gene gun). Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Plants, plant cells and tissues transformed with a heterologous nucleic acid sequence of interest are readily detected using methods known in the art including, but not limited to, restriction mapping of the genomic DNA, PCR-analysis, DNA-DNA hybridization, DNA-RNA hybridization, DNA sequence analysis and the like.

Additionally, selection of transformed plant cells may be accomplished using a selection marker gene. It is preferred, though not necessary, that a selection marker gene be used to select transformed plant cells. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene, which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methothrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the Ti-plasmid of *Agrobacterium*, the tk-gene from SV40, cytochrome P450 from *Streptomyces griseolus*, the Adh-gene from *Maize* or *Arabidopsis*, etc. Any gene encoding an enzyme capable of converting a substance which is otherwise harmless to plant cells into a substance that is harmful to plant cells may be used.

It is contemplated that the Nod2 polynucleotides of the present invention may be utilized to either increase or decrease the level of Nod2 mRNA and/or protein in transfected cells as compared to the levels in wild-type cells. Accordingly, in some embodiments, expression in plants by-the methods described above leads to the overexpression of Nod2 in transgenic plants, plant tissues, or plant cells.

In other embodiments of the present invention, the Nod2 polynucleotides are utilized to decrease the level of Nod2 protein or mRNA in transgenic plants, plant tissues, or plant cells as compared to wild-type plants, plant tissues, or plant cells. One method of reducing Nod2 expression utilizes expression of antisense transcripts. Antisense RNA has been used to inhibit plant target genes in a tissue-specific manner (e.g., van der Krol et al., Biotechniques 6:958-976 [1988]). Antisense inhibition has been shown using the entire cDNA sequence as well as a partial cDNA sequence (e.g., Sheehy et al., Proc. Natl. Acad. Sci. USA 85:8805-8809 [1988]; Cannon et al., Plant Mol. Biol. 15:39-47 [1990]). There is also evidence that 3' non-coding sequence fragment and 5' coding sequence fragments, containing as few as 41 basepairs of a 1.87 kb cDNA, can play important roles in antisense inhibition (Ch'ng et al., Proc. Natl. Acad. Sci. USA 86:10006-10010 [1989]).

Accordingly, in some embodiments, the Nod2 nucleic acids of the present invention (e.g., SEQ ID NOs: 1 and 33, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs, which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes is described in Haseloff, et al., Nature 334:585-591 (1988).

Another method of reducing Nod2 expression utilizes the phenomenon of cosuppression or gene silencing (See e.g., U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al., Plant Cell 2:279-289 [1990]; van der Krol et al., Plant Cell 2:291-299 [1990]; Smith et al., Mol. Gen. Genetics 224:477-481 [1990]). Accordingly, in some embodiments the Nod2 nucleic acids (e.g., SEQ ID NOs:1 and 33), and fragments and variants thereof are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants, which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

In other embodiments of the present invention, small interfering double stranded RNA molecules (RNAi) are used to silence expression of Nod2 in cells in vitro or in vivo. In some embodiments, RNAi are approximately 21-25 nucleotides and target the gene of to be silenced.

VIII. Drug Screening Using Nod2

The present invention provides methods and compositions for using Nod2 as a target for screening drugs that can alter, for example, RICK signaling, and thus the physiological effects of NF-κB (e.g., inflammatory response). For example, drugs that induce or inhibit NF-κB mediated inflammatory responses can be identified by screening for compounds that target Nod2 or regulate Nod2 gene expression.

As described above, experiments conducted during the course of development of the present invention demonstrated that Nod2 mediates the host-response to bacterial muropeptides and that individuals with disease associated mutations of Nod2 exhibit defective responses to bacterial muropeptides. Accordingly, in some embodiments, the present invention provides methods of screening for compounds that restore the host response to bacterial muropeptides. For example, in some embodiments, an NF-κB reporter gene assay (See e.g., Example 9) or other NF-κB activation assay is used to screen for compounds that restore the host response to bacterial muropeptides. In some embodiments, a mutant Nod2 that does not respond to muropeptides is expressed in cells and libraries of compounds are screened for their ability to restore the NF-κB activation response. In some embodiments, the test compounds are muramyl peptides (e.g., MDP or analogs of MDP).

In other embodiments, the present invention provides methods of screening compounds (e.g., MDP analogs) for the ability to induce Nod2 mediated NF-κB activation. Such compounds find use as vaccine adjuvants. In other embodiments, the present invention provides methods of screening for "anti-adjuvant" compounds (e.g., MDP analogs) that inhibit Nod2 mediated NF-κB activation. For example, in some embodiments, compounds are contacted with a cell expressing wild type Nod2 and the activation of NF-κB is measured (e.g., using the reporter gene assay described in the below Examples). In some embodiments, the level of NF-κB is compared to the level of NF-κB activation induced by MDP. Preferred compounds for use as adjuvants are those that are more potent activators of NF-κB activation than MDP.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al, Proc. Natl. Acad. Sci. 87:6378-6382 [1990]; Felici, J. Mol. Biol. 222: 301 [1991]).

In other embodiments, drug screens are used to identify compounds that alter the ability of Nod2 to interact with RICK. The present invention is not limited to a particular mechanism of action. Indeed, an understanding of the mechanism of action is not necessary to practice the present invention. Nevertheless, it is contemplated that Nod2 binds to RICK, and this binding results in the activation of NF-κB. Accordingly, it is contemplated that binding assays are useful for screening for compounds that block Nod2 binding to RICK. In particular, it is contemplated that such screens are capable of identifying compounds that are useful for inhibiting NF-κB activity and thus for treating Crohn's disease. The binding need not employ full-length RICK and Nod2. Indeed, portions of RICK and Nod2 may be utilized in the binding assays. For example, in some embodiments, a fragment of Nod2 containing the two CARD domains is utilized in the binding assay.

In other embodiments, the present invention provides methods of screening for compounds that increase or decrease the recognition or binding of Nod2 to pathogens, pathogen components, or pathogen binding proteins, and consequently, affect downstream signaling and NF-κB activation. In some embodiments, wild-type Nod2 or a fragment thereof is utilized. In other embodiments, Nod2 containing one or more variations (e.g., mutations or polymorphisms) is utilized.

In one screening method, the two-hybrid system is used to screen for compounds (e.g., drug) capable of altering (e.g., inhibiting) Nod2 function(s) (e.g., NF-κB-mediated signal transduction) in vitro or in vivo. In one embodiment, a GAL4 binding site, linked to a reporter gene such as lacZ, is contacted in the presence and absence of a candidate compound with a GAL4 binding domain linked to a Nod2 fragment and a GAL4 transactivation domain II linked to a NF-κB fragment. Expression of the reporter gene is monitored and a decrease in the expression is an indication that the candidate compound inhibits the interaction of Nod2 with NF-κB. Alternately, the effect of candidate compounds on the interaction of Nod2 with other proteins (e.g., proteins known to interact directly or indirectly with NF-κB) can be tested in a similar manner.

In another screening method, candidate compounds are evaluated for their ability to alter Nod2 signaling by contacting Nod2, NF-κB, NF-κB-associated proteins, or fragments thereof, with the candidate compound and determining binding of the candidate compound to the peptide. The protein or protein fragments is/are immobilized using methods known in the art such as binding a GST-Nod2 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., $E.\ coli$ XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate Nod2 physiological effects (e.g., apoptosis).

In another screening method, one of the components of the Nod2/NF-κB signaling system, such as Nod2 or a fragment of Nod2, is immobilized. Polypeptides can be immobilized using methods known in the art, such as adsorption onto a plastic microtiter plate or specific binding of a GST-fusion protein to a polymeric bead containing glutathione. For example, GST-Nod2 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of Nod2 with the other peptide. A variation of this method allows for the screening of compounds that are capable of disrupting a previously-formed protein/protein complex. For example, in some embodiments a complex comprising Nod2 or a Nod2 fragment bound to another peptide is immobilized as described above and contacted with a candidate compound. The dissolution of the complex by the candidate compound correlates with the ability of the compound to disrupt or inhibit the interaction between Nod2 and the other peptide.

Another technique for drug screening provides high throughput screening for compounds having suitable binding affinity to Nod2 peptides and is described in detail in WO 84/03564, incorporated herein by reference. Briefly, large numbers of different small peptide test compounds are synthesized on a solid substrate, such as plastic pins or some other surface. The peptide test compounds are then reacted with Nod2 peptides and washed. Bound Nod2 peptides are then detected by methods well known in the art.

Another technique uses Nod2 antibodies, generated as discussed above. Such antibodies capable of specifically binding to Nod2 peptides compete with a test compound for binding to Nod2. In this manner, the antibodies can be used to detect the presence of any peptide that shares one or more antigenic determinants of the Nod2 peptide.

In some embodiments of the present invention, compounds are screened for their ability to inhibit the binding of pathogen components (e.g., including, but not limited to, bacterial cell surface proteins; fungi proteins, parasite proteins, and virus proteins) to Nod2. Any suitable screening assay may be utilized, including, but not limited to, those described herein.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with Nod2 and variants thereof for screening compounds for activity, and in particular to high throughput screening of compounds from combinatorial libraries (e.g., libraries containing greater than $10^4$ compounds). In some embodiments, the libraries are libraries of MDP analogs. The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding Nod2 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. As described above, it is contemplated that Nod2 binds to RICK, and this binding results in the activation on NF-κB. Therefore, in some embodiments, the reporter gene construct comprises the 5' regulatory region (e.g., promoters and/or enhancers) of a protein whose expression is controlled by NF-κB in operable association with a reporter gene (See Example 4 and Inohara et al., J. Biol. Chem. 275:27823 [2000] for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these-proteins, with the exception of green fluorescent protein, is detected through the use of chemiluminescent, calorimetric, or bioluminecent products of specific substrates (e.g., X-gal and luciferin). Comparisons between compounds of known and unknown activities may be conducted as described above.

IX. Therapeutics

In still further embodiments, the present invention provides therapeutics useful in the treatment of Crohn's disease. As described above, patients with mutations in Nod2 lack a response or have a diminished response to bacterial muropeptides. It is contemplated that therapeutics that restore activity against bacterial muropeptides are beneficial to Crohn's disease patients harboring NOD2 mutations. In some embodiments, therapeutics are identified using the drug screening methods described above.

In some embodiments, muropeptides (e.g., MDP or MDP analogues) are used to treat Crohn's disease. The present invention is not limited to a particular mechanism. Indeed, an understanding of the mechanism is not necessary to practice the present invention. Nonetheless, it is contemplated that MDP analogs with enhanced stimulatory activity are useful for enhancing MDP recognition in patients with detective MDP recognition. In still other embodiments, MDP analogs are used in patients with normal Nod2 function to stimulate innate immunity, which may be faulty in the disease.

In some embodiments, the Nod2 status (e.g., the presence or absence of variant Nod2 alleles) of a patient is first determined (e.g., using the methods described above). The appropriate treatment can then be administered based on the patient's Nod2 status.

In some embodiments, Crohn's disease therapeutics are delivered to the gut. In other embodiments, therapeutics are delivered to the blood. Exemplary formulation and delivery methods are described below.

In other embodiments, the present invention provides compounds (e.g., MDP) analogs that alter (e.g., increase or decrease) Nod2 signaling. Such compounds find use as vaccine adjuvants (e.g., compounds that increase Nod2 signaling) or as anti-adjuvants (e.g., compounds that decrease Nod2 signaling). In some embodiments, anti-adjuvant compounds are used to reduce toxicity (e.g., side effects such as inflammation or fever) associated with administration of an adjuvant. In some preferred embodiments, anti-adjuvants are administered following an adjuvant. It is preferred that anti-adjuvants are not administered until protective immunity against the vaccine has developed.

X. Pharmaceutical Compositions Containing Nod2 Nucleic Acid, Peptides,

Analogs and Modulators

The present invention further provides pharmaceutical compositions which may comprise all or portions of Nod2 polynucleotide sequences, Nod2 polypeptides, inhibitors or antagonists of Nod2 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by apoptosis of cells or other NF-κB. mediated effects. The invention provides methods for inhibiting Nod2 interaction with NF-κB and NF-κB-associated proteins by administering peptides or peptide fragments of Nod2. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, Nod2 nucleotide and Nod2 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, Nod2 polynucleotide sequences or Nod2 amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of Nod2 may be that amount that suppresses apoptosis. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

In some embodiments, drug delivery systems are used that deliver the pharmaceutical compound of interest (e.g., MDP analogs) directly to the gut. Several types of colonic drug delivery systems are currently available, including enemas (L. R. Sutherland et al., Med. Clin. North Amer., 74, 119 (1990)); rectal foams (Drug. Ther. Bull., 29, 66 (1991)); and delayed release oral formulations in the form of Eudragit-coated capsules which dissolve at pH 7 in the terminal ileum (K. W. Schroeder et al., New Engl. J. Med., 317, 1625 (1987)). In other embodiments enteric coating, which remain undissociated in the low pH environment of the stomach, but readily ionizes when the pH rises to about 4 or 5 are utilized, including, but not limited to, polyacids having a pHa of 3 to 5.

Compositions comprising a compound of the invention formulated in a pharmaceutical acceptable carrier may be prepared, placed in an appropriate container, and labeled for treatment of an indicated condition. For polynucleotide or amino acid sequences of Nod2, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts Nod2 levels.

A therapeutically effective dose refers to that amount of Nod2 which ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for Nod2 than for the inhibitors of Nod2. Administration to the bone marrow may necessitate delivery in a manner different from intravenous injections.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); 1 or L (liters); ml (milliliters); µl (microliters); cm (centimeters); mm (millimeters); µm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Fisher (Fisher Scientific, Pittsburgh, Pa.); Sigma (Sigma Chemical Co., St. Louis, Mo.); Promega (Promega Corp., Madison, Wis.); Perkin-Elmer (Perkin-Elmer/Applied Biosystems, Foster City, Calif.); Boehringer Mannheim (Boehringer Mannheim, Corp., Indianapolis, Ind.); Clonetech (Clonetech, Palo Alto, Calif.); Qiagen (Qiagen, Santa Clarita, Calif.); Stratagene (Stratagene Inc., La Jolla, Calif.); National Biosciences (National Biosciences Inc, Plymouth Minn.)and NEB (New England Biolabs, Beverly, Mass.), CARD (caspase-recruitment domain); EST (expressed sequence tag); HA (hemagglutinin); IκB (inhibitor of NF-κB); IKK (IκB kinase); LRRs (leucine-rich repeats); NBD (nucleotide-binding domain); NF-κB (nuclear factor κB); TNFα (tumor necrosis factor α); wt (wild-type); Ab (antibody); IL-1 (interleukin 1); IL-1R (IL-1 receptor); LPS (lipopolysaccharide); LTA (lipoteichoic acid); PGN (peptidoglycan); SBLP (synthetic bacterial lipoprotein); and TLR (Toll-like receptor).

Methodology

Reagents. LPS from various sources in this study were obtained from Sigma (St. Louis, Mo.). PGN from *Staphylocuccus aureus* was obtained from Fluka-Chemie (Buchs, Germany). Mannan from *Candida albicans* 20A was a gift of P. Lehmann (Medical College of Ohio). PaM3CysSerLyS4, a synthetic bacterial lipoprotein analogue (SBLP) was a gift of A. Zychlinsky (New York University School of Medicine).

Isolation of the Nod2 cDNA. Nucleotide sequences encoding peptides with homology to Nod1 (GeneBank accession numbers AC007728 and AQ534686) were found in the public genomic database using the TBLASTN program. The coding region of human nod2 was obtained by reverse transcriptase (RT)-PCR amplification and 5' RACE using Nod2-specific oligonucleotide primers cDNA fragments and mRNA from primary mammary tissue as a template. 5' RACE was performed using a commercial kit (Roche Molecular Biochemicals, Indianapolis, Ind.). For PCR, three sets of primers were used: 5'-ATGTGCTCG-CAGGAGGCTTTTCAGGCA-3' (SEQ ID NO:37) and 5'-CGCCTCACCCACCACCAGCACAGTGT-3' (SEQ ID NO:38); 5'-CATGGCTGGACCCCCGCAGAAGAGC-CCA-3' (SEQ ID NO:39) and 5'-CA-TGCCCGGGT-TCATCTGGCTCATCCGG-3' (SEQ ID NO:40); 5'-GC-CATGCCCGGGTTCATCTGGCTCATC-3' (SEQ ID NO:41) and 5'-TGAGTCGAGACATGGGGAAAGCT-GCTTC-3' (SEQ ID NO:42). For 5' RACE, the initial primer 5'AGCAGCTCGACCAGCTGGCTCCTCTGT-3' (SEQ ID NO:43) was used and the product was PCR amplified with the anchored primer and second Nod2-specific primer: 5'-GACAGGCCCAAGTACCCTTATTCCAGA-3' (SEQ ID NO:44). The resulting cDNA fragments were digested with restriction enzymes and ligated to generate an unique cDNA containing the entire open reading frame of Nod2. The cDNA sequence was verified by nucleotide sequencing.

Northern Blot and RT-PCR Analysis of Nod2 Expression. A 3.7 kb fragment containing the entire Nod2 coding region was radiolabeled by random priming using a commercial kit (Roche Molecular Biochemicals) and applied for analysis of human poly(A)' RNA blots from various tissues (Clontech Laboratories, Palo Alto, Calif.) according to the manufacturer's instructions. Peripheral blood leukocytes were obtained from heparinized venous blood from healthy volunteers by Ficoll-Paque (Amersham Pharmacia Biotech, Uppsala, Sweden) density gradient centrifugation. Granulocytes were separated from red blood cells by brief incubation with hypotonic lysis buffer. The mononuclear cell population was fractionated into lymphocytes and monocytes by adherence to plastic dishes. For RT-PCR analysis, 2 µg of total RNA from each cell preparations were used to generate first strand cDNA using a commercially available kit (Gibco BRL; Gaithersburg, Md.). Nod2 cDNA fragments corresponding to the Nod2 coding region were amplified by PCR using two sets of specific primers; PI: 5'-ATGT-GCTCGCAGGAGGCTTTTCAGGCA-3' (SEQ ID NO:45); P2: 5'-CGCCTCACCCACCACCAGCACAGTGT-3' (SEQ ID NO:46); P3: 5'-ATGTGCTCGCAGGAGGCTTTTCAG-GCA-3' (SEQ ID NO:47) and P4: 5'-CG-CCTCACCCAC-CACCAGCACAGTGT-3' (SEQ ID NO:48). As a control, a cDNA fragment of the human glyceraldehyde-3 -phosphate dehydrogenase was amplified using the primers 5'-GAGT-CAACGGATTTGGTCGTAT-3' (SEQ ID NO:49) and 5'-AGTCTTCTGGGTGGCAGTGAT-3' (SEQ ID NO:50).

Construction of Expression Plasmids. The Nod2 cDNA was cloned into pcDNA3-HA and pcDNA3-Fpk3-Myc (Inohara et al., [2000], supra). Deletion and site-directed mutants of Nod2 (129-1040, A125-214, 1-125, 1-301, 1-744, 265-1040, 126-301, 265744, 744-1040, K305R, 1-744K305R) were constructed by a PCR method and cloned into pcDNA3-HA and pcDNA3-Fpk3-Myc (Inohara et al., [2000], supra). The authenticity of all constructs was confirmed by sequencing. pcDNA3-Flag-RICK, pcDNA3-Flag-RICK(1-374), pcDNA3-Flag-RICK(374-540), pcDNA3-Myc-RICK(406-540), pcDNA3-Myc-RIP(558-671), pRK7-Flag-IKKα, pRK7-FlagIKKβ-K44A, RSVMad-3MSS(Iκ-Bα-S32A/S36A), pRK7-Flag-IKKβ, pRK7-Flag-IKKβ-K44A, and pcDNA3-Flag-IKKγ(134-419) have been described previously (Inohara et al., supra, 10). The expression plasmids pcDNA3-Nod1-Flag, pcDNA3-Nod1 (I-648)-Flag, pcDNA3-Flag-IKKi, pcDNA3CIPER-Flag, pCMV-ILIR, pCMV-TLR4-Flag, pcDNA3-Flag-RIP, pcDNA3-MyD88 DN(amino acids 1-109), pcDNA3-CD14, pCMV-MD2-FLAG and pcDNA3-β-gal have also been described previously (Inohara et al., [1999], Supra; Inohara et al., [1999], Supra; Inohara et al., [2000], supra; Shimada et al., Int. Immunol., 11:1357-1362 [1999]; Huang et al., PNAS, 94:12829-12832 [1997]; Medzhitov et al., Mol. Cell, 2:253-258 [1998]; Hsu et al., Immunity, 4:387-396 [1996]). To construct the expression plasmid producing C-terminally HA-tagged mature interleukin-1 P (IL1β), pcDNA3-mIL1β-HA, the mature region of mouse IL1β was amplified by PCR and inserted into pcDNA3-HA-pro which contains the signal sequence of protrypsin and the HA tag.

Transfection, Expression, Immunoprecipitation and Immunodetection of Tagged Proteins. HEK293T cells were co-transfected with pcDNA3-Nod2-HA and various expression plasmids as described (Inohara. et al., [1999] supra). To test the interaction between wt RICK and Nod2 mutant proteins, HEK293T cells were co-transfected with pcDNA3-Flag-RICK and wt or mutant Nod2 expression plasmids. Proteins co-immunoprecipitated with anti-HA antibody were detected with anti-Flag antibody. To test the interaction between wt Nod2 and RICK mutants, HEK293T cells were cotransfected with pcDNA3-HA-Nod2 and pcDNA3-Flag-RICK, pcDNA3-Flag-RICK(1-374) or pcDNA3-Flag-RICK (374-540) (Inohara et al., [1999] supra). Proteins co-immunoprecipitated with anti-HA antibody were detected with anti-Flag antibody. Proteins in total lysate were detected by anti-Flag and anti-HA monoclonal antibody, respectively.

NF-κB activation assays. NF-κB activation assays were performed as described (Inohara et al., [1999] supra, Inohara et al., [2000], supra). Briefly, Rat1 fibroblasts and its derivative 5R cell line (Yamaoka et al., Cell 93: 1231-1240 [1998]) as well as HEK293T cells were co-transfected with 12 ng of the reporter construct pBVIx-Luc, plus indicated amounts of each expression plasmid and 120 ng of pEF-BOS-β-gal in triplicate as described. 24 hr post-transfection, cell extracts were prepared and its relative luciferase activity was measured as described (Inohara et al., [1999] supra, Inohara et al., [2000], supra). Results were normalized for transfection efficiency with values obtained with pEF-BOS-β-gal.

In vitro LPS binding assay. $1\times10^8$ HEK293T cells were transfected with expression plasmids indicated in figure legends as described (Inohara et al., [2000], Supra). Twenty-four hr post-transfection, S 100 fractions were prepared from transfected cells as described-using Buffer A (Poltorak et al., [1998], Supra). For FIG. 10A, S100 lysate containing 5 mg of protein was incubated with 300 ng [$^3$H] LPS ($1\times10^5$ Bq, 347 Bq/ng, List Biological Laboratories, Campbell, Calif.) from *Escherichia coli* K12 KCD25, 6 μg anti-FLAG M2 antibody (Sigma Chemical), 10 μl Protein A-Sepharose and 10 μl Protein G-Sepharose at 4° C. for 2 hr. Proteins bound to the matrix were washed 5 times with 1 ml of Buffer A. The bound radioactivity was measured using a Liquid Scintillation Counter Beckman LS5000LD. For FIG. 3B, proteins were immunopurified first from 20 mg of S100 lysate as described above and incubated with 300 ng [$^3$H] LPS in the presence of 10 mg bovine serum albumin Fraction V (Sigma Chemical) at 4° C. for 2 hr. After 5 washes with 1 ml of Buffer A, the bound radioactivity was measured. To monitor protein expression, proteins in 50 μg of S100 lysate were detected by immunoblotting with anti-FLAG Ab.

EXAMPLE 1

Figure 2:
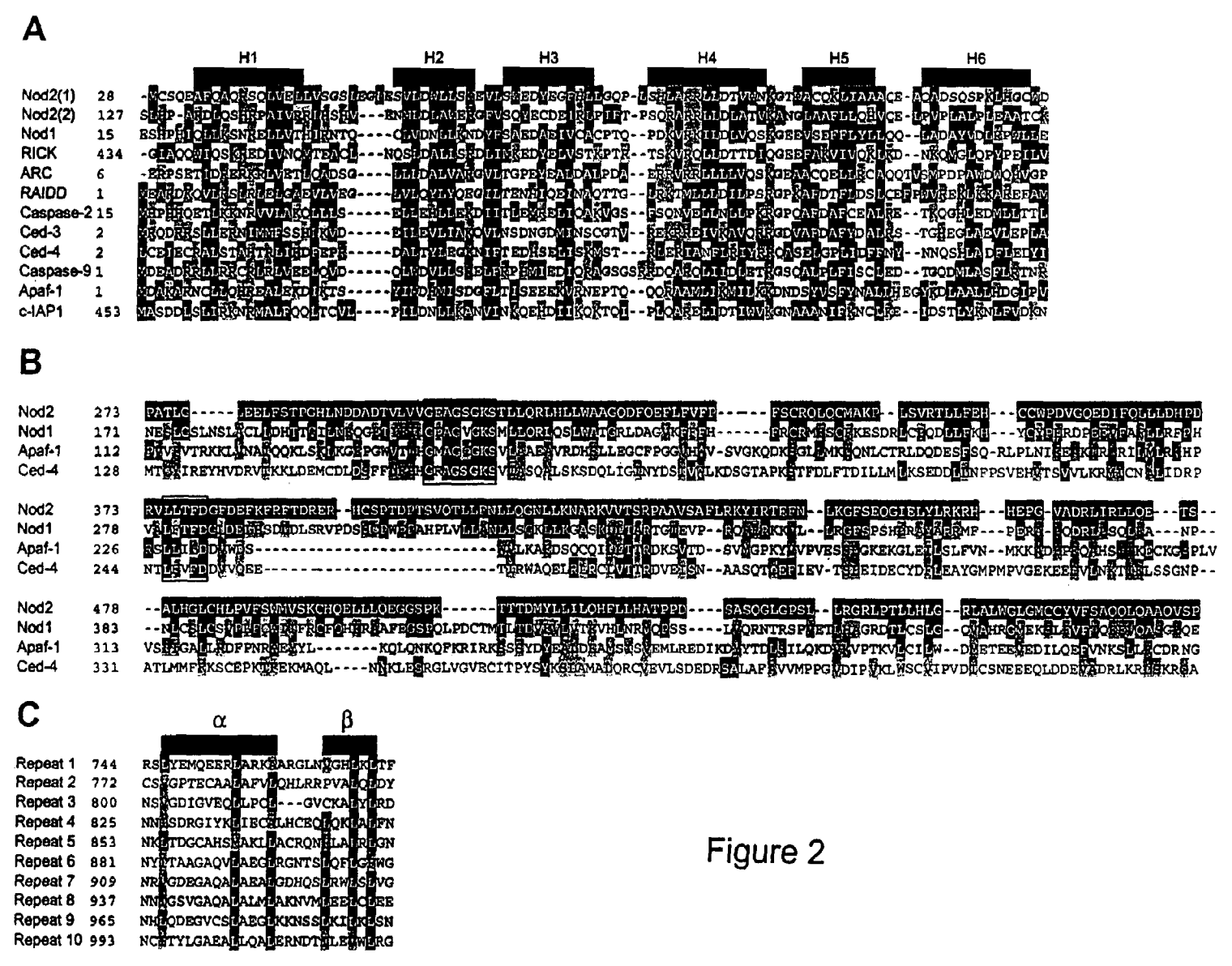

This Example describes the identification of Nod2. To identify novel Nod1/Apaf-I-like molecules, public genomic data bases were searched for genes encoding proteins with homology to Nod1 (Inohara et al., supra). A genomic sequence was identified in human chromosome 16 (GeneBank accession number AC007728) that encodes a peptide with significant homology to the NBD of Nod1. Analysis with GeneFinder of the genomic region predicted a gene encoding a novel protein with significant homology to Nod1. To determine the ends of the coding region, 5' RACE was performed using an oligonucleotide complementary to sequences encoding the N-terminus of the predicted protein and sequenced several EST cDNAs which contain partial sequences of the gene (GeneBank accession numbers AA775466, AA910520, A1090427). To amplify thee cDNA containing the entire open reading frame, we RT-PCR was performed with three sets of primers corresponding to overlapping sequences of the coding region of the gene. The predicted open reading frame encodes a protein of 1040 amino acids. A BLAST search of protein data bases indicated that the protein encoded by the new open reading frame was most homologous to Nod1 (34% amino acid identity). This protein was designated Nod2 given its high level of homology with Nod1 and thus represents a novel member of the Apaf-I/Nod1 superfamily (FIG. 1). Analysis of the nucleotide sequence revealed two potential in-frame translation initiation sites separated by 81 nucleotides. Further analysis revealed that both translation initiation sites can be utilized in cells, although the longer open reading frame is preferentially used (see below). For simplicity, the longer open reading frame is designated Nod2 and the product encoded by the shorter open reading frame is designated as Nod2b. A BLAST search and domain analyses revealed that Nod2 is composed of two NH2-terminal CARDs (residues 28-220) fused to a centrally located NBD domain (residues 273-577) containing consensus nucleotide-binding motifs followed by ten tandem LRRs (residues 744-1020) (FIGS. 1 and 2). Each of the 10 LRRs of Nod2 contained predicted α helix and β sheet sequences that is consistent with the prototypical horseshoe-shaped structure of LRRs (Kobe and Deisenhofer, Curr. Opin. Struct. Biol. 5: 409-416 [1995]) (FIG. 2C). Nod2 is the first protein known to encode two CARDs.

EXAMPLE 2

This Example describes the chromosomal localization and genomic organization of the human Nod2 gene. Two human BAC clones, RPII-327F22 and RPII-40IP9, containing the genomic sequence of human Nod2 (GenBank accession numbers AC007728 and AC007608, respectively) were identified. These BAC clones mapped to chromosome 16 at q12. Comparison of Nod2 cDNA and genomic sequences revealed that the Nod2 gene contains twelve coding exons.

EXAMPLE 3

Figure 3:
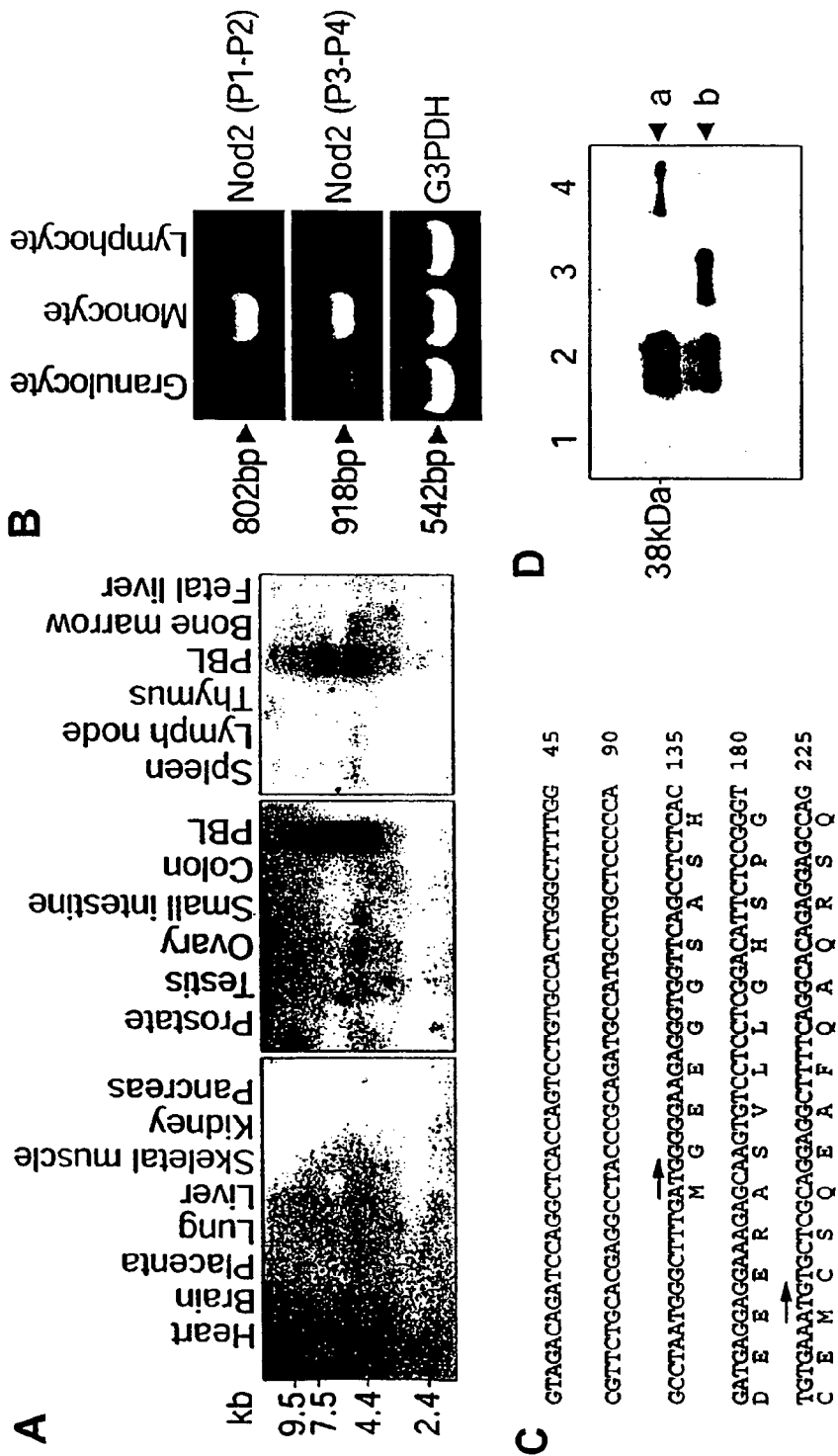
FIG. 3 shows an expression Analysis of Nod2.

This Example demonstrates that the expression of Nod2 is most abundant in monocytes. Northern blot analysis showed Nod2 to be expressed as two 7.0 and 5.5 kb transcripts in peripheral blood leukocytes with little or no detectable expression in various human tissues (FIG. 3A). This highly restricted pattern of expression is in contrast to that of Nod1 and Apaf-1 which are expressed in virtually all adult tissues although at different levels (Inohara et al., supra). To determine the cells that express Nod2, peripheral blood leukocytes were fractionated into granulocyte, lymphocyte and monocyte populations and analyzed by RT-PCR analysis with two different sets of oligonucleotide primers complementary to Nod2 coding sequences. The analysis showed that Nod2 was expressed primarily in monocytes (FIG. 3B). Because the Nod2 sequence contained two potential in-frame translation initiation sites separated by 81 nucleotides (FIG. 3C), their usage was determined by transfection of a Nod2 construct containing both translation initiation sites into HEK293T cells. Because the difference in size between both predicted Nod2 products is only 27 amino acids, we expressed a COOH-terminally truncated Nod2 lacking residues 302-1040 to facilitate the identification of the translation initiation sites. As a control, Nod2 plasmids were engineered that express each translation initiation site separately within a canonical Kozak's translation initiation motif. The analysis revealed that both translation initiation sites in the Nod2 open reading frame were used, although the most NH2-terminal translation initiation codon was more efficient as assessed by immunoblotting of cell extracts with an antibody that recognizes a COOH-terminal HA tag (FIG. 3D).

EXAMPLE 4

This example describes the activation of NF-κB by Nod2. Because of the homology between Nod1 and Nod2, tests were conducted to determine whether expression of Nod2 activates NF-κB by transfection of Nod2 plasmids into HEK293T cells. Transfection of the wt Nod2 cDNA induced potent activation of NF-κB, as measured with a reporter luciferase construct (see below). In addition, we tested the Nod2b cDNA and obtained similar results to those observed with Nod2. A panel of Nod2 mutants was generated to determine the regions of Nod2 that are required for NF-κB activation (FIG. 4A). Immunoblotting analysis revealed that these mutant constructs were expressed when transiently transfected into HEK293T cells (FIG. 4B). Expression of as little as 3 ng of wt Nod2 induced 18-fold activation of NF-κB (FIG. 4C). Expression of a Nod2 mutant form lacking the LRRs resulted in enhanced NF-κB activation, while mutants expressing the LRRs or the NBD alone were inactive (FIG. 4C). The enhanced activity of the Nod2 mutant lacking the LRRs could not be explained by increased expression of the mutant (FIG. 4A). Consistent with these results, it was shown previously that deletion of the LRRs of Nod1 and WD-40 repeats of Apaf-I results in enhanced NF-κB activation and increased ability to activate procaspase-9, respectively (Inohara et al., supra, Srinivasula et al., supra, Hu et al., supra). Deletion of the CARDs of Nod2, either singly or in combination, resulted in total loss of NF-κB activity (FIG. 4C). However, expression of both CARDs alone, but not each CARD separately, was sufficient for NF-κB activation (FIG. 4C). Thus, both CARDs of Nod2 are necessary and sufficient for NF-κB activation, suggesting that the CARDs acts as an effector domain in Nod2 signaling. The conserved lysine residue in the P-loop of Nod1 and Apaf-I is important for the activities of these proteins (Inohara et al., [1999] supra, Inohara et al., [2000], supra, Hu et al., EMBO J. 18: 3586-3595 [1999]). Similarly, replacement of the corresponding lysine for arginine in Nod2 resulted in diminished NF-κB activity that was rescued at least in part by deletion of the LRRs (FIG. 4C).

The ability of Nod2 to induce apoptosis was also investigated. Overexpression of Nod2 did not induce apoptosis by itself but enhanced apoptosis induced by caspase-9 expression. These results are similar to those reported for Nod1 and Apaf-1 (Bertin et al., supra, Inohara et al., [1999] supra).

EXAMPLE 5

Figure 5:
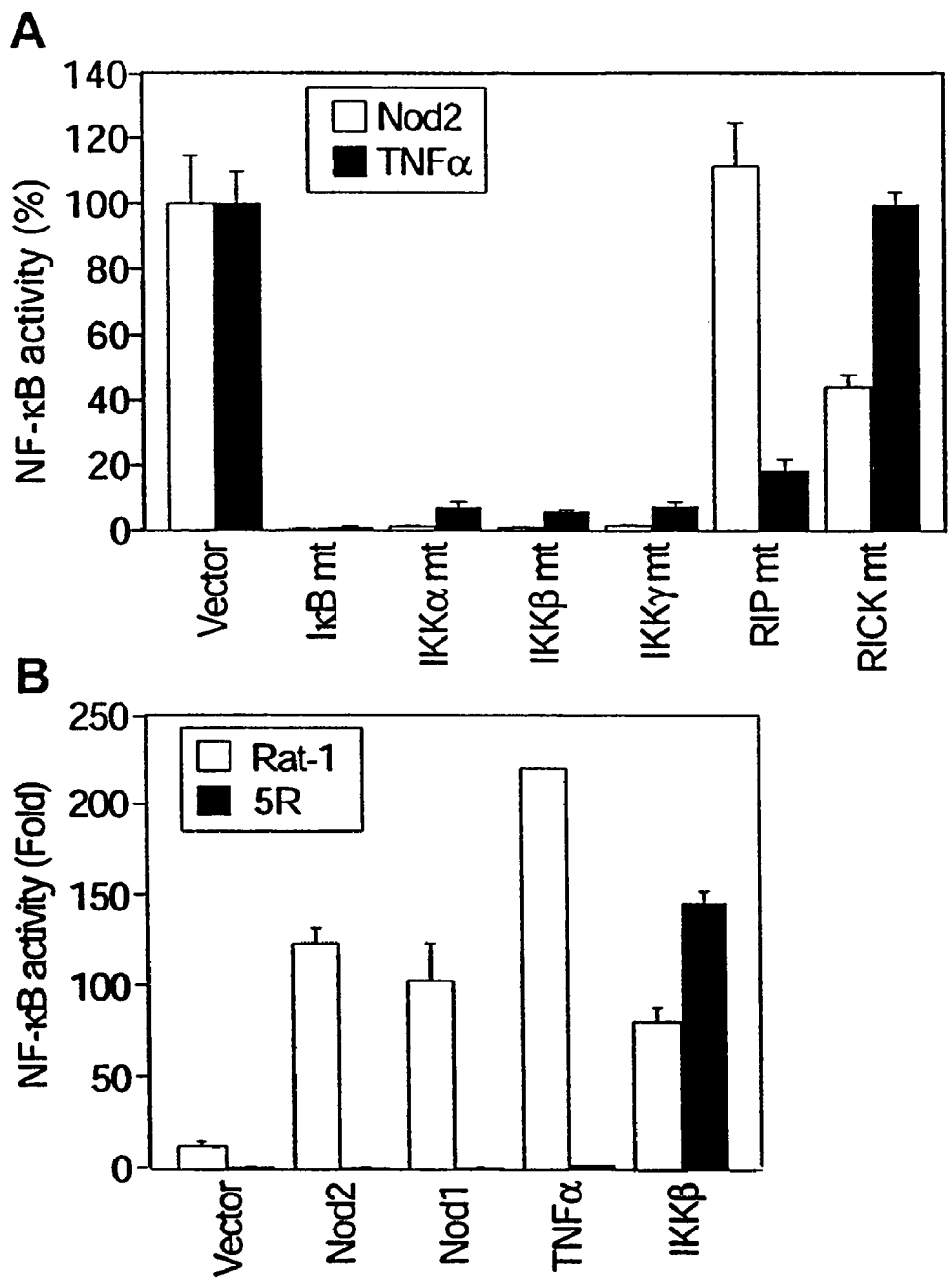
FIG. 5 shows that Nod2 Acts through the IKK complex to activate NF-KB.

This example demonstrates that NF-κB activation induced by Nod2 requires IKKγ and is inhibited by dominant negative forms of IKKs and RICK. A main pathway of NF-κB activation is mediated by IκB kinases (IKKS) resulting in IκB phosorylation and release of cytoplasmic NF-κB (Karin, J. Biol. Chem. 274: 27339-27342 [1999]). To determine whether Nod2 activates an IKK-dependent pathway, Nod2 was co-expressed with mutant forms of IKKα, IKKβ and IκB that have been shown to act as dominant inhibitors of their corresponding endogenous counterparts and/or the IKK complex (Karin, supra). In addition, a truncated mutant of IKKγ/Nemo (residues 134-419) was used that is defective in IKKα and IKKβ binding and acts as an inhibitor of NF-κB activation induced by RIP and RICK (Inohara et al., [2000], supra). The NF-κB activity induced by Nod2 as well as that induced by TNFα stimulation were greatly inhibited by mutant IKKα, IKKβ, IKKγ, and IκBα (FIG. 5A). Because RICK has been shown to serve as a downstream target of Nod1 (Bertin et al., supra, Inohara et al., [1999] supra, Inohara et al., [2000], supra), a truncated form of RICK containing its CARD (residues 406-540) that acts as a dominant inhibitor of Nod1 activity (Bertin et al., supra) was used to test whether NF-κB activation induced by Nod2 is similarly inhibited by this RICK mutant. NF-κB activation induced by Nod2 was inhibited by mutant RICK but not by a mutant form of RIP that expresses its death effector domain (FIG. 5A). The inhibition by the CARD of RICK was specific in that it did not interfere with ability of TNFα to induce NF-κB, an activity that was inhibited by the RIP mutant (FIG. 5A). To verify that Nod2 acts upstream of the IKK complex to activate NF-κB, we tested the ability of Nod2 to activate NF-κB in parental Rat1 fibroblasts and 5R cells, a Rat1 derivative cell line that is defective in IKKγ, an essential subunit of the IKKs (Yamaoka et al., supra). Nod2, as well as Nod1 and TNFoc, induced NF-κB activity in parental Rat1 cells but not in IKKγ-deficient 5R cells (FIG. 5B). As a control, expression of IKKβ, which functions downstream of IKKγ, induced NF-κB activation in both Rat1 and 5R cell lines (FIG. 5B). These results indicate that Nod2 acts through IKKγ/IKK/IKKβ to activate NF-κB.

EXAMPLE 6

This Example demonstrates that Nod2 associates with RICK via a homophilic CARD-CARD interaction. The CARD motif functions as an effector domain that mediates specific homophilic interaction with downstream CARD-containing molecules (Hofmann et al., Trends Biochem. Sci. 22: 155-156 [1997]). Because NF-κB activation induced by Nod2 was inhibited by a RICK truncated mutant, the ability of RICK to act as a direct downstream mediator of Nod2 signaling was tested. To test a physical association between Nod2 and RICK, HEK293T cells were co-transfected with plasmids expressing HA-tagged wt or mutant forms of Nod2 and Flag-tagged RICK and cellular extracts were immunoprecipitated with anti-HA antibody. Immunoblotting with anti-Flag antibody revealed that RICK associated with Nod2

Figure 6:
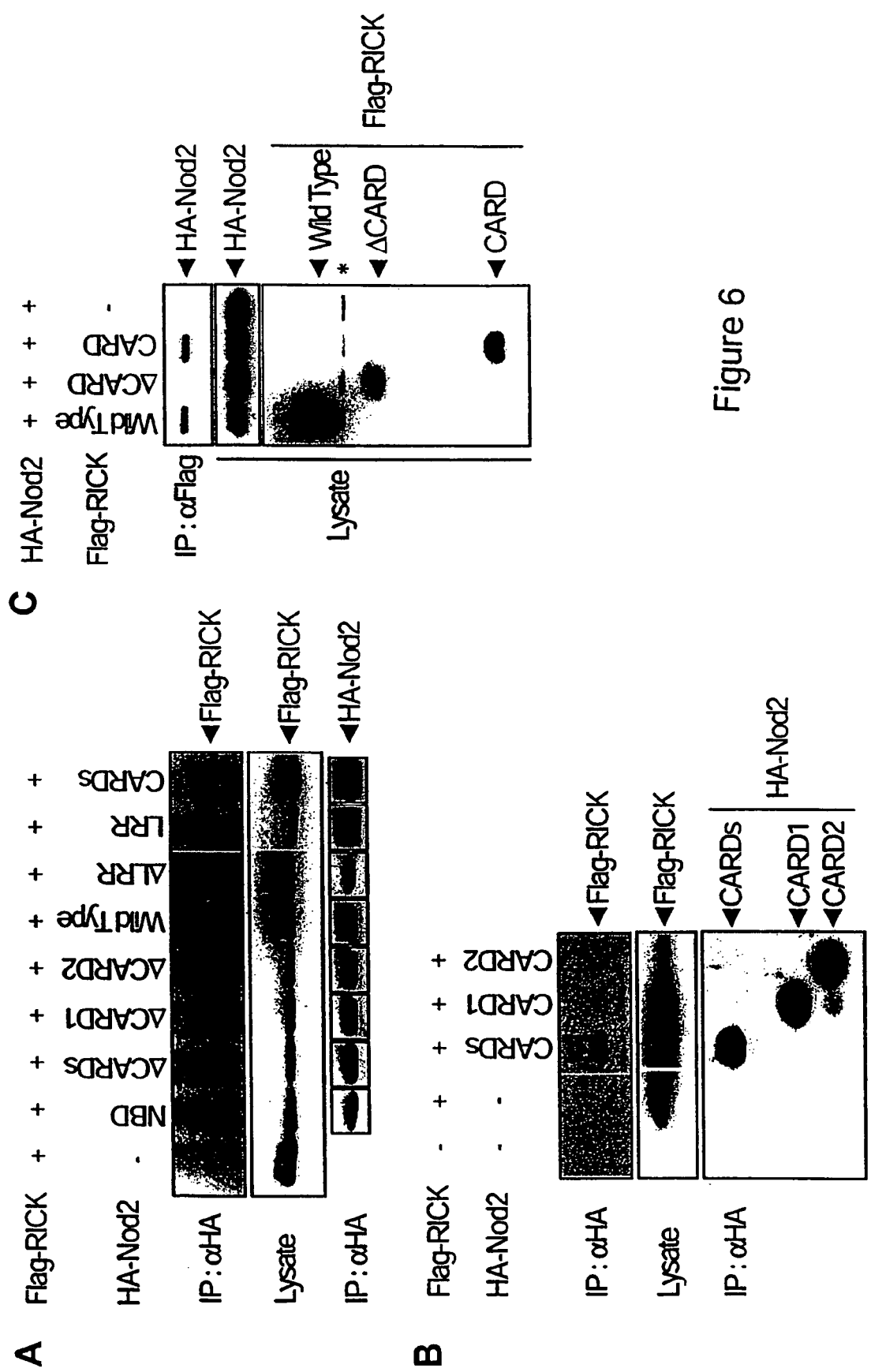
FIG. 6 shows the interaction of Nod2 with RICK.

(FIG. 6A). The association was mediated by both CARDs of Nod2, as only Nod2 proteins containing both CARDs were capable of interacting with RICK (FIG. 6A, B). The association of Nod2 with RICK was specific in that Nod2 did not associate with several CARD-containing proteins including Apaf-1, caspase-1, caspase-4, c-IAP-1, c-IAP2, procaspase-9, Bcl-10, RAIDD, and Ced-4 nor with several molecules that activate NF-κB including TRAF-1, TRAF-2, TRAF-5, TRAF-6, RIP, NIK, TRADD, IKKα, IKKβ or IKKγ. To determine the region of RICK that associates with Nod2, mutant forms of RICK expressing the CARD (residues 374-540) or lacking the CARD (residues 1-374) were co-expressed with Nod2 and the cell extracts were immunoprecipitated with anti-Flag antibody. The analysis showed that only the CARD of RICK co-immunoprecipitated with Nod2 (FIG. 6C). Thus, Nod2 and RICK associate via a homophilic CARD-CARD interaction.

EXAMPLE 7

Figure 7:
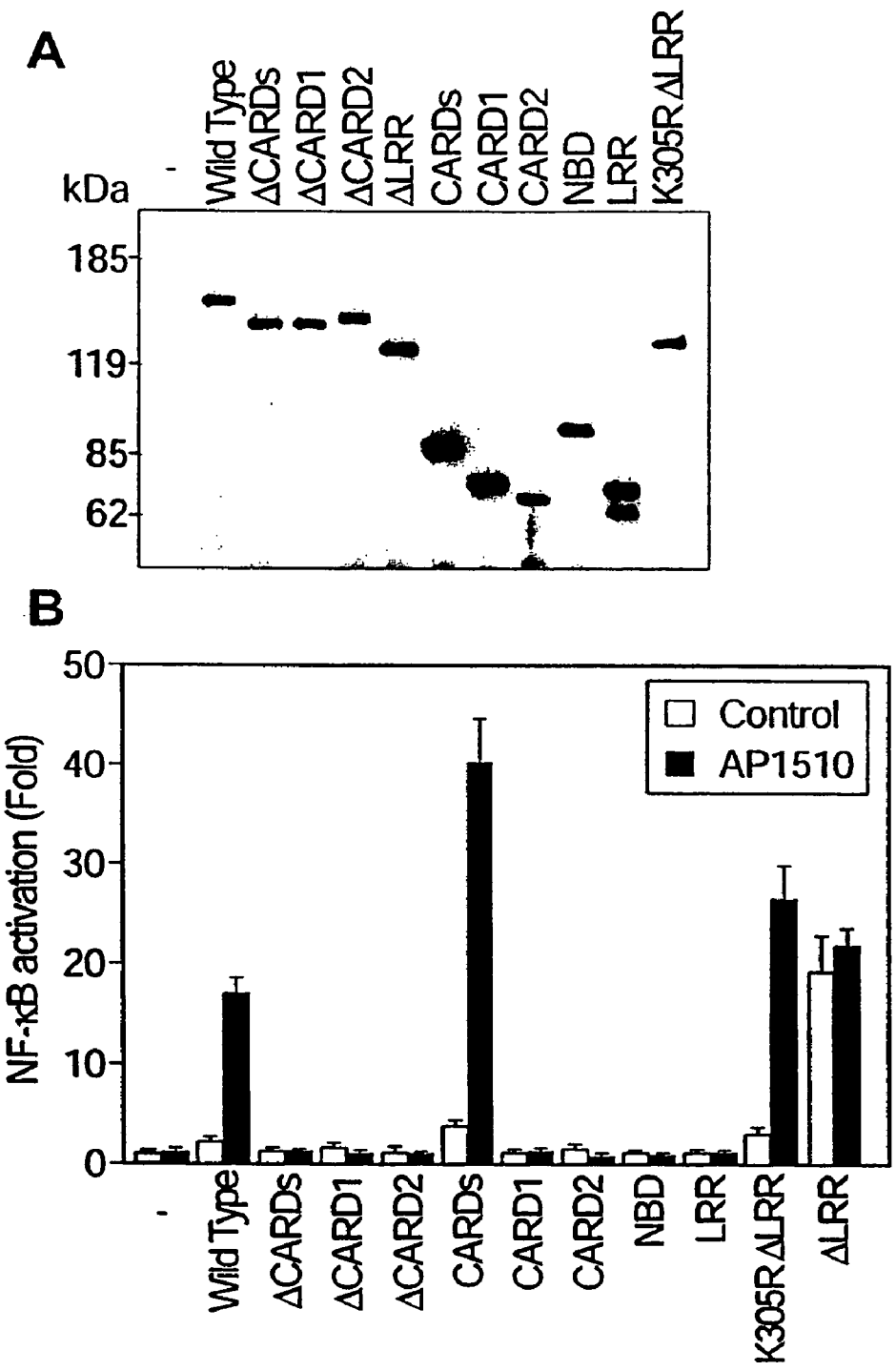
FIG. 7 shows that enforced oligomerization of Nod2 induces NF-κB activation.

This Example demonstrates that enforced oligomerization of Nod2 induces NF-KB activation. Previous studies showed that the NBD of Nod1 and Apaf-I mediates oligomerization of these molecules, an activity that is critical for NF-κB and caspase-9 activation, respectively (Srinivasula et al., supra, Hu et al., [1998] supra, Inohara et al., [2000], supra). In the case of Nod1, its oligomerization appears to promote proximity of RICK and NF-κB activation. To test a similar role for Nod2, plasmids were constructed to express chimeric proteins in which wt or Nod2 mutants were fused to three tandem repeated dimerization domains of Fpk (Fpk3), which can be oligomerized by the cell-permeable ligand AP1510 (MacCorkle et al., Proc. Nat. Acad. Sci. U. S. A. 95: 3655-3660 [1998]). Immunoblotting analysis showed that the chimeric Fpk3-Nod2 constructs were expressed when transfected in HEK293T cells (FIG. 7A). Because wt Nod2 alone induces NF-KB activation, we expressed suboptimal amounts of the chimeric Fpk3-Nod2 constructs into HEK293T cells. Under these experimental conditions, expression of Nod2-Fpk3 induced NF-KB activation in a ligand-dependent manner (FIG. 7B). Consistent with the results shown in FIG. 4C, enforced oligomerization of both CARDs but not each CARD singly induced NF-κB activation (FIG. 7B). Similarly, NF-κB activation induced by a Nod2 P-loop mutant lacking the LRRs (K305RΔLRR), which have reduced ability to induce NF-κB activation, was enhanced by enforced oligomerization (FIG. 7C). A Nod2-Fpk3 construct lacking the LRRs induced NF-κB activation in the absence and presence of AP1510 (FIG. 7B). The latter result might be explained by our observations that Nod2 lacking the LRRs has enhanced activity to self-associate and induce NF-κB (FIG. 4C).

EXAMPLE 8

Figure 8:
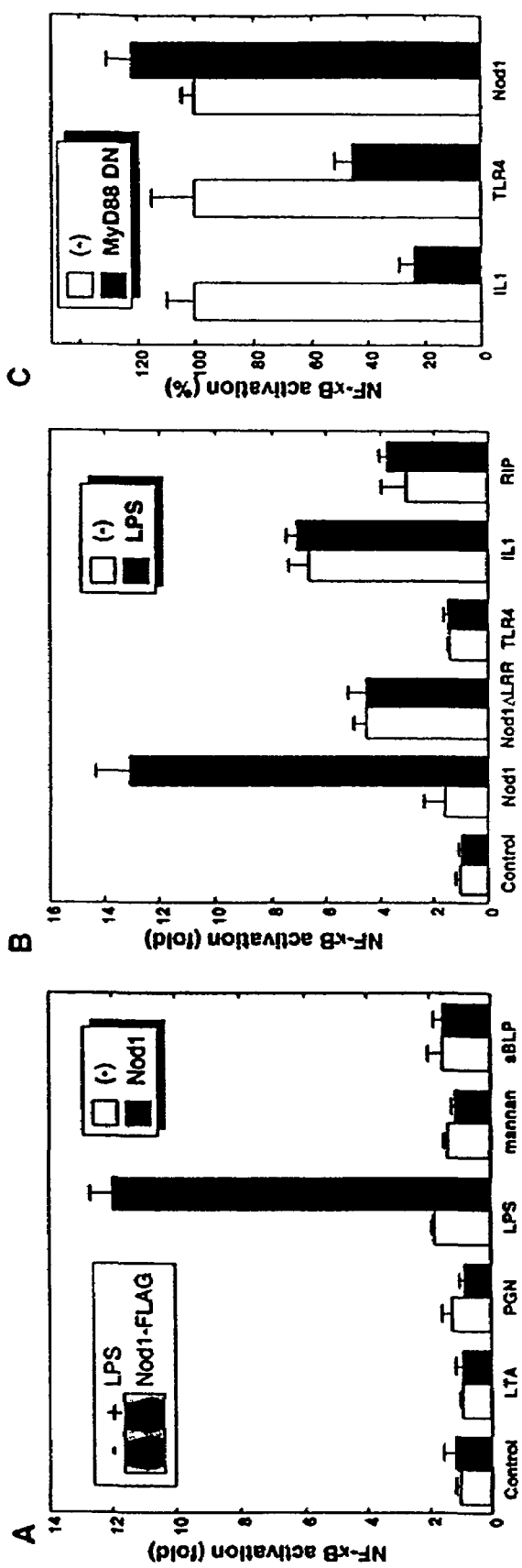
FIG. 8 shows the response of HEK293T cells expressing Nod1 to bacterial and fungal pathogen components.

This Example describes the role of Nod1 in the cellular response to microbial components. Human embryonic kidney HEK293T cells were transiently co-transfected with a Nod1 expression plasmid or control plasmid and a NF-κB reporter construct in the presence of bacterial or fungal products. No significant induction of reporter gene activity was observed when the cells transfected with control plasmid were exposed to LPS, PGN, LTA, synthetic bacterial lipopeptide (SBLP) or mannan (FIG. 8A). These results are in agreement with previous observations in HEK293 cells (Yang et al., Nature, 395:284-288 [1998]; Aliprantis et al., Supra; Chow et al., Supra; Schwandner et al., J. Biol. chem., 274:17406-17409 [2000]). Because overexpression of Nod1 induces NF-κB activation (Zou et al., Cell, 90:405-413 [1997]; Bertin et al., J. Biol. Chem., 274:12955-12858 [1999]), HEK293T cells were transfected with 0.3 ng of Nod1 and measured for NF-κB activation after incubation with various pathogen components. LPS, but not the other microbial products tested, induced significant NF-κB activation (about 12-fold) in cells expressing trace amounts of Nod1 (FIG. 8A). To demonstrate that NF-κB activation by LPS is specific for cells expressing Nod1, HEK293T cells were transfected with expression plasmids producing interleukin-1 receptor (IL1R) and its ligand interleukin-1β (IL1β) or RIP, a mediator of the TNFα signaling pathway (Huang et al.,[1997] Supra; Hsu et al., [1996], Supra). As expected, stimulation of the IL1R and expression of RIP induced NF-κB activation in the absence of LPS (FIG. 8B). Significantly, LPS did not enhance NF-κB activation induced by IL1R stimulation or RIP (FIG. 8B).

Figure 9:
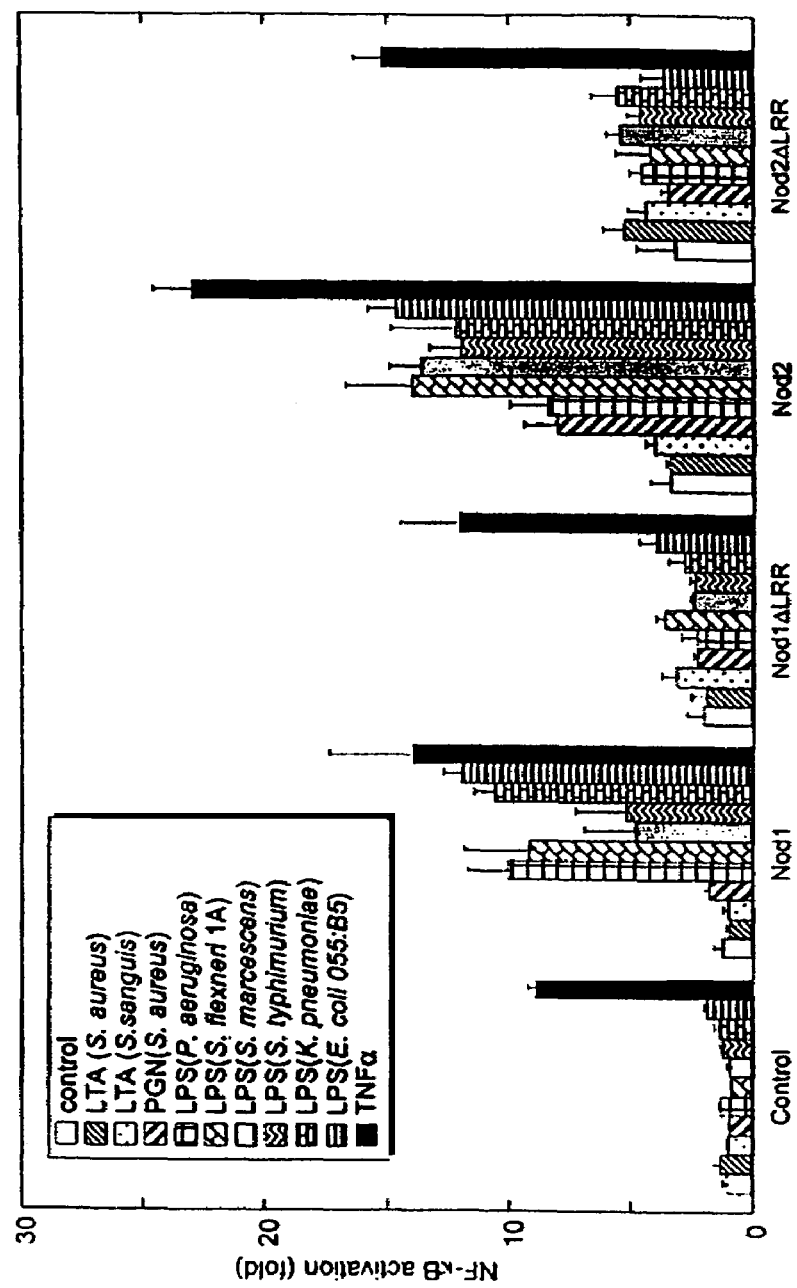
FIG. 9 shows differential responsiveness of Nod1 and Nod2 to LPS from various sources. 1×10$^5$ HEK293T cells were transfected with 0.3 ng of pcDNA3-Flag (−), pcDNA3-Nod1-Flag (Nod1) or pcDNA3-Nod1(1-648)-Flag (Nod1ΔLRR), 0.03 ng of pcDNA3-Nod2 or pcDNA3-Nod2 (1-744)-Flag (Nod2ΔLRR) in the presence of 600 ng of pcDNA3, 73 ng pEF1BOS-βgal and 7.3 ng pBXIV-luc. 8 hr post-transfection, cells were treated with 10 µg/ml each pathogen, LTA from *S. aureus* or *S. sanguis*, PGN from *S. aureus*, LPS from *Pseudomonas aeruginosa, Shigella flexneri* 1A, *Sarratia marcescens, Salmonella typhimurium, Klebsiella pneumoniae* or *E. coli* 055:B5, or left alone without treatment. For TNFα stimulation, 22 hrs after transfection, cells were incubated with 10 ng/ml of TNFα for 2 hr.

Plant disease-resistant proteins have C-terminal LRRs that are critical for pathogen-specific responses (Dixon et al., [2000], Supra). Alterations in their LRRs results in unresponsiveness to particular pathogens (Dixon et al., [2000], Supra), suggesting that the LRRs of Nod1 might be also required for the response to LPS. To test this hypothesis, HEK293T cells were transfected with plasmids expressing wild-type or truncated Nod1 mutant lacking the LRRs (Nod1ΔLRR) and treated with LPS. Expression of Nod1ΔLRR induced higher NF-κB activation than wild-type Nod1 in the absence of LPS, as previously reported (Inohara et al., [1999], Supra). Significantly, LPS did not enhance NF-κB activation induced by Nod1ΔLRR (FIG. 9). Thus, the LRRs are essential for Nod1 to respond to LPS.

Several studies have provided conclusive evidence that TLR4 is a cell surface receptor for LPS (Aderam and Ulevitch, Supra, Poltorak et al., Science, 282:2085 [1998]; Chow et al., Supra; Takeuchi et al., Immunity, 4:443 [1999]). Therefore, it is possible that expression of Nod1 confers LPS responsiveness through TLR4. To test this possibility, HEK293T cells were co-transfected with a TLR4 expression plasmid and NF-κB activity was measured in the presence and absence of LPS. Expression of TLR4 alone did not induce NF-κB activation in the presence of LPS, which is consistent with recent reports that additional cell surface molecules such as MD2 and CD14 are required for TLR4-mediated LPS responses in cells (Chow et al., Supra; Takeuchi et al., Supra). In accord with the latter, co-transfection of TLR4, CD14 and MD2 expression plasmids induced 8-fold activation of NF-κB (see figure legend of FIG. 8C). To further verify that Nod1 confers LPS responsiveness independently of TLRs, a dominant negative mutant of MyD88, a common signaling molecule of IL-1 and Toll-related receptors including TLR4, was co-expressed with Nod1 or TLR4, CD14 and MD2. as a control, and transfected cells were stimulated with LPS. Co-expression of the MyD88 mutant suppressed NF-κB activation induced by both TLR4 and IL1R stimulation, but it did not affect LPS-mediated NF-κB activation induced by Nod1 (FIG. 8C). Furthermore, expression of a dominant negative mutant of TRAF6, a signaling molecule of TLR signaling pathways, did not block NF-κB activation induced by Nod1, but inhibited TLR4-mediated NF-κB activation (Inohara et al., [1999], Supra). These results indicate that NF-κB activation in Nod1-expressing cells induced by LPS is not mediated by the TLR4 signaling pathway. Consistent with this notion are recent observations showing that the Nod1 signaling pathway leading to NF-κB activation is distinct to that of TLRs. Nod1 activates NF-κB through its association with RICK, a protein kinase that directly interacts with IKKγ/NEMO, the regulatory subunit of the IκB kinase complex (Inohara et al., [2000], Supra).

LPS from different gram-negative bacteria have diverse structures (Rietschel et al., Curr Top. Microbiol. Immunol., 216:39-81 [1997]). To determine if Nod1 confers responsiveness to LPS from several bacterial sources, Nod1-expressing cells were stimulated with LPS from six pathogenic bacteria or TNFα, as a positive control. All LPS preparations induced NF-κB activation in Nod1-expressing cells, but different sources of LPS differed in their ability to enhance Nod-1-mediated NF-κB activation (FIG. 9). As it was found with LPS from *Escherichia coli* O55:B5 (FIG. 8B), none of the LPS preparations induced significant NF-κB activation in cells expressing a Nod1 mutant lacking the LRRs (FIG. 9).

Plants have numerous disease resistant R genes and mammalian as well as insect cells have multiple TLR family members to respond to different pathogens (Dixon et al., [2000], supra). Notably, Nod2, another Nod1-like protein that is homologous to Nod1 (34% amino acid identity) is comprised of N-terminal CARDS, NBD and LRRs. The presence of multiple Nod family members suggests that Nod1 and Nod2 may have different specificities for pathogen components. To test this, HEK293T cells were co-transfected with plasmids expressing wild-type or mutant Nod2 lacking the LRRs. As it was observed with Nod1, all LPS preparations including those from invasive bacteria such as *Salmonella* and *Shigella*, stimulated NF-κB activation in cells expressing wild-type Nod2 but not mutant Nod2 (FIG. 9). Notably, LPS from *Sarratia macreseens* and *Salmonella typhimurium* was more effective in inducing NF-κB activation in cells expressing Nod2 than Nod1 (FIG. 9). Furthermore, PGN preparation from *Staphylococcus aureus* stimulated NF-KB activation in cells expressing Nod2 but not Nod1 (FIG. 9). The molecular basis for the differential response of Nod1 and Nod2 to both LPS and PGN is unclear. Further biochemical analyses and structure determination of LPS moiety recognized by Nod I and Nod2 are required to understand the differential response of Nod proteins to bacterial components.

Figure 10:
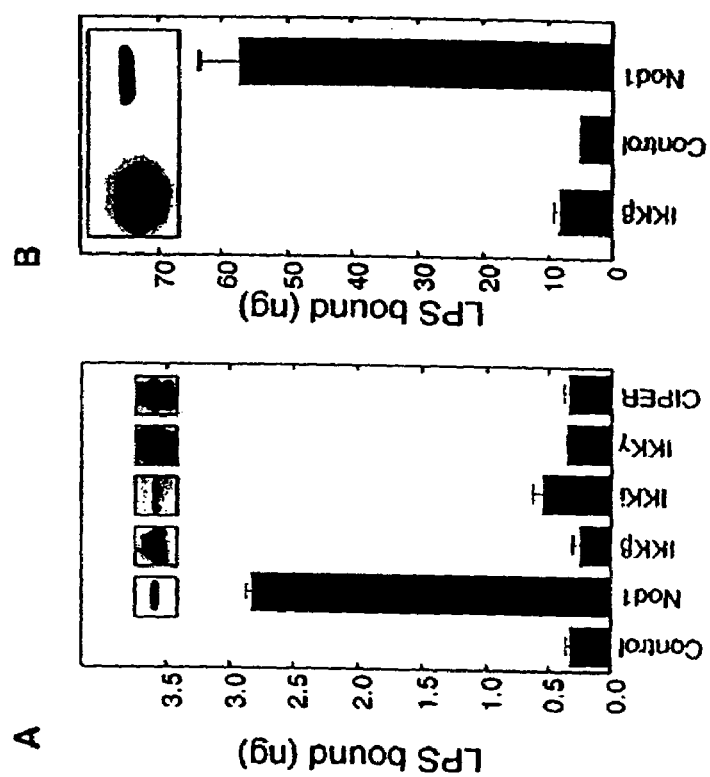
FIG. 10 shows the physical Interaction between Nod1 and LPS. 1×10$^8$ HEK293T cells were transfected with 30 µg of pcDNA3-Flag-Nod1, pRK7-FLAG-IKKβ, pcDNA3-FLAG-IKKi, pcDNA3-FLAG-IKKγ or pcDNA3-CIPER-FLAG (Takeuchi et al., Immunity, 4:443 [1999]). 24 hr post-transfection, S100 fractions were prepared from transfected cells as described below. The radioactivity of [$^3$H] LPS co-immunoprecipitated with anti-FLAG Ab was determined as described below.

Apaf-1, a Nod1-like molecule which plays a central role in apoptosis, mediates responsiveness to cytochrome c leaked from mitochondria (Dixon et al., Supra; Li et al., Cell, 91:479-489 [1997]). Apaf-I directly binds to cytochrome c (Li et al., Supra). To determine if Nod1 binds to LPS, S100 cell lysates were prepared from HEK293T cells expressing Nod1 and the ability of Nod1 to bind radiolabeled LPS was tested by a modified immunoprecipitation assay. LPS was co-immunoprecipitated with Flag-tagged Nod1, but not with other Flag-tagged control proteins (FIG. 10A). Thus, Nod1 is associated with an LPS binding activity present in the cytosolic fraction of HEK293T cells. However, it is possible that Nod1 does not directly bind to LPS and that the association requires other cytosolic factors. For example, dATP or ATP is required for the response of Apaf-I to cytochrome c (Li et al., Supra). To begin to test this, we first immunoprecipitated Nod1 or IKKβ, as a control protein, with anti-Flag antibody and the ability of the immunoprepitated proteins to bind LPS was tested in nucleotide-free buffer. Immunopurified Nod1 exhibited LPS binding activity, but control IKKβ did not (FIG. 10). These results suggest that Nod1 directly binds LPS. However, the possibility can not be excluded that Nod1 interacts with LPS through an intrinsic cytosolic factor(s) that is tightly bound to Nod1 and co-immunoprecipitates with Nod1 in the absence of LPS. In plants, the *Arabidopsis thaliana* disease resistance RPS2 gene product that is structurally related to Nod1 and Nod2 can form a protein complex in vivo with the product of the phytopathogenic bacterium *Pseudomonas syringae* avrRpt2 gene but the protein complex also contained at least one additional plant protein of approximately 75 kDa (Leister and Katagiri, Plant J., 22:345-354 [2000]).

EXAMPLE 9

This Example describes the recognition of muramyl dipeptides mediated through Nod2.

A. Methods

Recognition of Peptidoglycan by NOD2

HEK293T cells were transfected with 0.1 ng pcDNA3-NOD2 (NOD2), or 3 ng pcDNA3-TLR4-Flag plus 3 ng pcDNA3-MD2 (TLR4+MD2) or left untreated (−) in the presence of reporter pBxIV-luc and pEF-BOS-β-gal as described previously (See above Examples and Inohara et al., J. Biol. Chem. 276:2551 [2001]). Eight hours post-transfection, 1 µg/ml of LPS from *E. coli* O55:B5 prepared by the phenol extraction method (phenol), LPS further purified by gel filtration chromatography (gel filt.), LPS prepared by the phenol extraction and alkaline-detoxified (aLPS), purified lipid A from *Escherichia coli* O55:B5 LPS, or 5 µg/ml of PGN from *Staphylococcus aureus* were added with fresh medium. Twenty-four hours post-transfection κB-dependent transcription was determined as described (Inohara et al., [2001], supra). Values represent mean of normalized data ±S.D. of triplicate cultures.

Cells were stimulated with gel-filtration fractions of PGN from *B. subtilis* digested or undigested with Mutanolysin for 24 hr and fractionated by Superose 12 gel filtration chromatography with 10 mM HEPES, 100 mM NaCl, pH 7.4.

Stimulation of Nod2 by Synthetic Muropeptides

Molecules with two copies (2mer) or four copies (4mer) of GlcNAc-MurNAc with attached L-Ala-D-isoGln and their counterparts lacking dipeptide (2mer-aa, 4mer-aa) were synthesized as described (Inamura et al., Tetrahedron Lett. 42:7613 [2001]). Eight hours post-transfection, the indicated amount of each compound was added to the cells and the ability of each compound to activate NF-κB was determined as above. The ability of MDP (100 ng/ml) and sBLP (1000 ng/ml) to activate NF-κB was determined by transfection of 0.3 ng pcDNA3-Nod2 (Nod2) or control plasmid (−) into HEK293 cells or in HEK293 cells stably transfected with TLR2 (TLR2) or with control plasmid (−) and reporter pBxIV-luc and pEF-BOS-β-gal plasmids. Values represent the mean of normalized data ±S.D. of triplicate cultures.

Activation of Normal and Crohn's Disease-Associated Nod2 Proteins by MDP

HEK293T cells were transfected with 0.3 µg of pMX-puro expressing normal Nod2 or mutants carrying P268S (SEQ ID NOs:56 (nucleic acid) and 57 (amino acid), P268S/R702W (SEQ ID NOs: 57 (nucleic acid) and 58 (amino acid)), P268S/G908 (SEQ ID NOs: 60 (nucleic acid) and 61 (amino acid)), P268S/L1007fsinsC (SEQ ID NOs: 54 (nucleic acid) and 55 (amino acid)) or empty plasmid (−). Eight hours post-transfection, 100 ng/ml MDP was added to the cultured cells and at 24 hours post-transfection NF-κB activity was determined as described in FIG. 1A. Values represent the normalized mean data ±S.D. of triplicate cultures. The results shown are representative of three separate experiments.

Stimulation of PBMNC from Individuals with Crohn's Disease Alleles

Genotyping was performed using a ddNTP primer extension system. Nuclear extracts from LPS-stimulated cells were pre-incubated with antibody specific for p50 subunit of NF-κB to monitor the size of the NF-κB-DNA complex. cDNA was amplified with specific primers for human IL-1β, glyceraldehyde-3-phosphate-dehydrogenase (GAPDH) as described (5) and A1 (5'-CGGATGTGGATACCTATAAGG-3' (SEQ ID NO: 53) and 5'-GTCATCCAGCCAGATT-TAGG-3' (SEQ ID NO:54)). The levels of IL-1β and A1 transcripts normalized to that of GAPDH were expressed relative to those in untreated cells that were considered as baseline. Specificity of the desired PCR products was determined by melting curve analysis. Histograms represent the mean ±S.D. of triplicate analyses.

B. Results

Human embryonic kidney (HEK293T) cells and a NF-κB-dependent luciferase reporter were used to compare the ability of NOD2 and TLR4 to recognize LPS and PGN. Because NOD2 is an intracellular protein, NOD2 activity was assessed under culture conditions that allow the internalization of the bacterial components into the cells (Inohara et al., J. Biol. Chem. 276:2551 [2001]). Expression of NOD2 and TLR4 together with its co-factor MD2 conferred responsiveness to purified LPS prepared by phenol extraction as reported (Ogura, Nature 411:603 [2001]), whereas only NOD2 induced the response to PGN (FIG. 17A). The lipid A moiety of LPS mediates TLR4/MD2 activation (Takeuchi et al., Immunity 11:443 [1999]). Consistent with the latter, NOD2, but not TLR4, responded to lipid A-depleted detoxified LPS prepared by alkaline treatment (FIG. 17A), whereas TLR4, but not NOD2, responded to purified lipid A (FIG. 17A). TLR4, but not NOD2, was stimulated by highly purified LPS prepared by gel-filtration chromatography (FIG. 17A). These results indicate that TLR4 and NOD2 recognize different bacterial components and suggest that PGN present in LPS preparations may contain the moiety recognized by NOD2.

To further characterize the bacterial structure recognized by NOD2, purified PGN was digested with the muramidases Mutanolysin or Cellosyl, which degrade the glycan chains and result in the generation of muropeptides composed of N-acetylglucosamine (GlcNAc) and N-acetylmuramic acid (MurNAc) linked to short peptides (Glauner et al., J. Biol. Chem. 263:10088 [1988]). Digested PGN was fractionated by gel-filtration chromatography. Analysis of each fraction revealed a major peak of NOD2-stimulating activity induced by mutanolysin digestion with a relative molecular mass of less than 12 kD consistent with that expected for muropeptides (FIG. 17B). Similar results were observed when PGN was digested with cellosyl, which revealed a single peak of NOD2-stimulatory activity of less than 12 kD.

PGN-derived muropeptides derived from most bacterial species are composed of GlcNAc-MurNAc linked to short peptides, which include the conserved dipeptide L-Ala and DisoGln or D-Glu (FIG. 18A). To determine more directly if muropeptides are recognized by NOD2, a panel of synthetic molecules with the structure of GlcNAc-MurNAc linked to L-Ala-D-isoGln, as well as muramyl dipeptide MurNAc-L-Ala-D-isoGln (MDP), which lacks GlcNAc, were used (FIG. 18A). GlcNAc-MurNAc-L-Ala-D-isoGln stimulated-NF-κB in a NOD2-dependent manner whereas disaccharide GlcNAc-MurNAc in dimeric or tetrameric forms did not (FIG. 18B) indicating that amino acid residues are important for stimulation of NOD2. Furthermore, MDP induced potent stimulation of NOD2 (FIG. 18B), indicating that GlcNAc is not essential for stimulatory activity. To determine further the specificity of the recognition of MDP by NOD2, the MDP analogs MurNAc-L-Ala-L-isoGln and MurNAc-D-Ala-D-isoGln were tested. Replacement of L-Ala for D-Ala or D-isoGln for LisoGln eliminated the ability of MDP to stimulate NOD2, indicating stereoselective recognition (FIG. 18C). Thus, a core structure important for recognition of NOD2 is MurNAc attached to L-Ala and D-isoGln or D-Gln.

TLR2 has been proposed to act as a surface receptor for PGN and certain bacterial lipoproteins including synthetic bacterial lipopeptide (sBLP) (Aliprantis et al., Science 285: 736 [1999]; Lee et al., J. Immunol. 168:4012 [2002]). Therefore, the ability of TLR2 and NOD2 to respond to MDP and sBLP was tested. TLR2 mediated a cellular response to sBLP but not to MDP (FIG. 18D). Conversely, MDP but not sBLP stimulated NOD2 activity (FIG. 18D). Thus, NOD2 and TLR2 recognize different bacterial structures.

Figure 19:
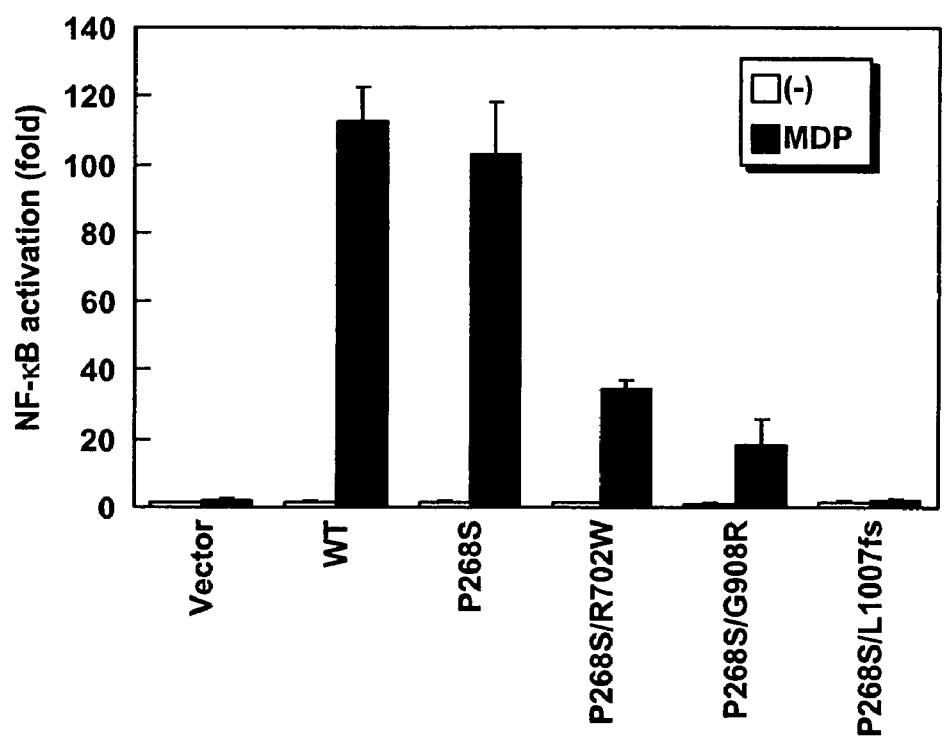
FIG. 19 shows activation of normal and Crohn's disease-associated NOD2 proteins by MDP.
Figure 20:
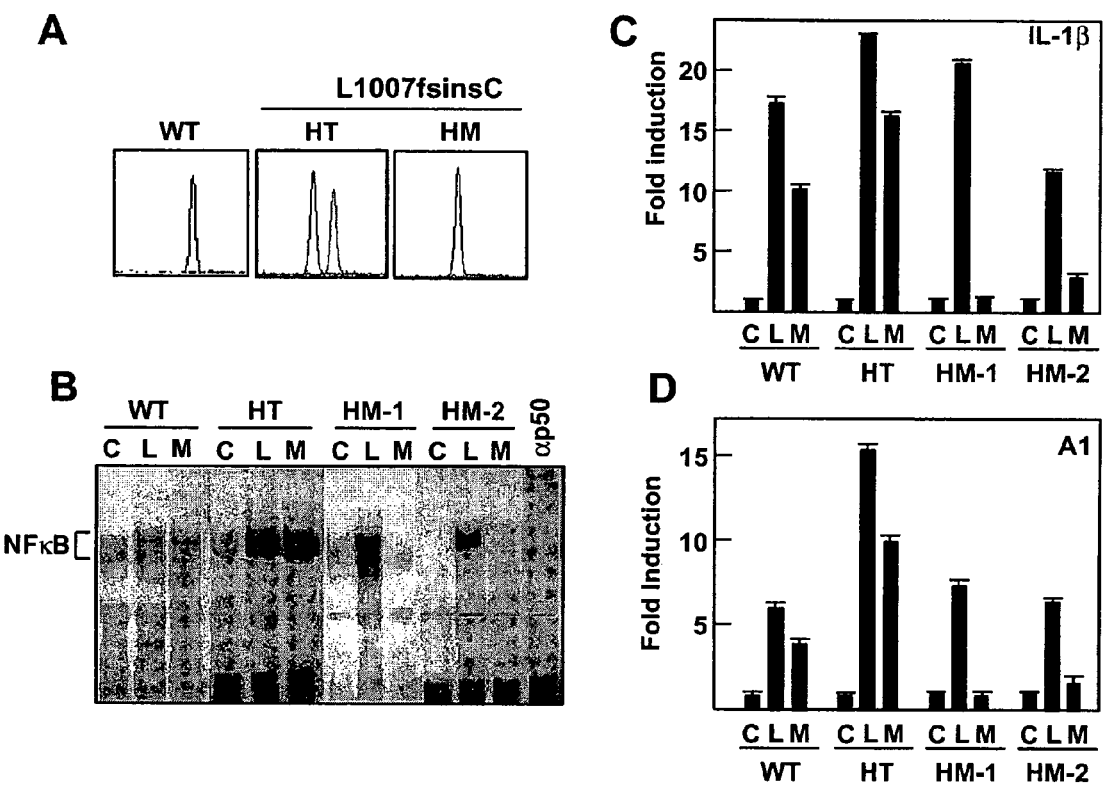
FIG. 20 shows stimulation of PBMNC from individuals carrying normal, heterozygous or homozygous L1007fs alleles with LPS and MDP.

The NOD2 variants associated with Crohn's disease, R702W, G908R and L1007fsinsC, occur on the same haplotype background, which includes the common P268S polymorphism (Hugot et al., Nature 411:599 [2001]; Ogura et al., Nature 411:603 [2001]). To compare the ability of normal and mutant NOD2 proteins to induce NF-κB activity in response to MDP, the NOD2 proteins were expressed in cells and evaluated in a functional assay. Both normal and P268S NOD2 induced similar levels of NF-κB activation in response to MDP (FIG. 19), which is consistent with the observation that P268S is not genetically associated with disease (Hugot et al., supra; Ogura et al., supra). In contrast, the P268S/R702W, P268S/G908R, and P268S/L1007fsinsC variants induced greatly reduced levels of NF-κB activation in response to MDP when compared to normal NOD2 (FIG. 19). The P268S/R702W and P268S/R702W point mutants retained some ability to respond to MDP, the truncated P268/L1007fsinsC protein did not respond at all (FIG. 19). Immunoblotting analysis revealed that the normal and NOD2 mutants are expressed at similar levels, indicating that the observed differences in MDP responses could not be explained by differential expression of the NOD2 constructs. The role of NOD2 in the recognition of MDP by primary cells from normal and Crohn's disease patients was next determined. A panel of healthy and Crohn's disease individuals were genotyped for the disease-associated NOD2 alleles and two individuals (one without clinical evidence of disease and one individual with Crohn's disease) who were homozygous for the loss-of-function L1007fsinsC mutation were identified (FIG. 20A). The identification of apparently healthy individuals homozygous for L1007fsinsC is expected in that the penetrance of the L1007fsinsC mutation is not complete (Hugot et al., supra; Ogura et al., supra; Hampe et al., Lancet 357:1925 [2001]; Ahmad et al., Gastroenterology 122:854 [2002]). Peripheral blood mononuclear cells (PBMNC) that are known to express NOD2 were isolated, incubated with MDP or LPS and NF-κB activation was assessed in nuclear extracts by an electrophoretic mobility shift assay (EMSA). Stimulation of PBMNC from individuals carrying normal or heterozygous NOD2 alleles with either LPS or MDP resulted in induction of the NF-κB-DNA complex (FIG. 20B). In contrast, PBMNC from individuals homozygous for L1007fsinsC did respond to LPS, but not to MDP (FIG. 20B). The DNA binding complex induced by MDP was shifted by incubation of the nuclear extracts with an antibody specific for the p50 subunit of NF-κB (FIG. 20B) and was inhibited by incubation with Bay11-7082, indicating that the detected protein-DNA complex contained NF-κB.

To further assess NF-κB activation, the mRNA levels of EL-1β and A1, two NF-κB target genes expressed in PBMNC (Cogswell et al., J. Immunol. 153:712 [1994]; Zong et al., Genes Dev. 13:384 [1999]), were evaluated by quantitative real-time polymerase-chain reaction (RT-PCR) analysis. Both IL-1β and A1 mRNA levels were induced by incubation with LPS and MDP in cells from individuals carrying normal or heterozygous NOD2 alleles (FIG. 20C and 20D). In contrast, LPS but not MDP increased the levels of both IL-1β and A1 mRNA in PBMNC from individuals homozygous for L1007fsinsC (FIG. 20C and 20D). Thus, PBMNC require the expression of normal NOD2 for their response to MDP but not to LPS.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

What is claimed is:

1. A method of modulating Nucleotide-binding oligomerization domain-containing protein 2 (Nod2) signaling in a subject, comprising:
    a) providing a compound, wherein said compound is a muramyl dipeptide selected from the group consisting of MurNAc-L-Ala-D-isoGln, and MuraNAc-L-Ala-D-Glu, which increases a subject's Nod2 activity in response to bacterial muropeptides; and
    b) administering said compound to a subject under conditions such that said subject's Nod2 activity is response to bacterial inuropeptides is increased.

2. The method of claim 1, wherein said subject is diagnosed with Crohn's disease and said test compound increases said subjects Nod2 activity is response to bacterial muropeptides.

3. The method of claim 1, wherein said compound is a vaccine adjuvant and said compound increases said subjects Nod2 activity is response to bacterial muropeptides.

* * * * *

SEQUENCE LISTING

<160> NUMBER OF SEQ ID NOS: 62

<210> SEQ ID NO 1
<211> LENGTH: 4485
<212> TYPE: DNA
<213> ORGANISM: Homo sapiens

<400> SEQUENCE: 1

```
gtagacagat ccaggctcac cagtcctgtg ccactgggct tttggcgttc tgcacaaggc      60
ctacccgcag atgccatgcc tgctccccca gcctaatggg ctttgatggg ggaagagggt     120
ggttcagcct ctcacgatga ggaggaaaga gcaagtgtcc tcctcggaca ttctccgggt     180
tgtgaaatgt gctcgcagga ggcttttcag gcacagagga gccagctggt cgagctgctg     240
gtctcagggt ccctggaagg cttcgagagt gtcctggact ggctgctgtc ctgggaggtc     300
ctctcctggg aggactacga gggcttccac ctcctgggcc agcctctctc ccacttggcc     360
aggcgccttc tggacaccgt ctggaataag ggtacttggg cctgtcagaa gctcatcgcg     420
gctgcccaag aagcccaggc cgacagccag tcccccaagc tgcatggctg ctgggacccc     480
cactcgctcc acccagcccg agacctgcag agtcaccggc cagccattgt caggaggctc     540
cacagccatg tggagaacat gctggacctg gcatgggagc ggggtttcgt cagccagtat     600
gaatgtgatg aaatcaggtt gccgatcttc acaccgtccc agagggcaag aaggctgctt     660
gatcttgcca cggtgaaagc gaatggattg gctgccttcc ttctacaaca tgttcaggaa     720
ttaccagtcc cattggccct gcctttggaa gctgccacat gcaagaagta tatggccaag     780
ctgaggacca cggtgtctgc tcagtctcgc ttcctcagta cctatgatgg agcagagacg     840
ctctgcctgg aggacatata cacagagaat gtcctggagg tctgggcaga tgtgggcatg     900
gctggacccc cgcagaagag cccagccacc ctgggcctgg aggagctctt cagcacccct     960
ggccacctca atgacgatgc ggacactgtg ctggtggtgg gtgaggcggg cagtggcaag    1020
agcacgctcc tgcagcggct gcacttgctg tgggctgcag ggcaagactt ccaggaattt    1080
ctctttgtct tcccattcag ctgccggcag ctgcagtgca tggccaaacc actctctgtg    1140
cggactctac tctttgagca ctgctgttgg cctgatgttg gtcaagaaga catcttccag    1200
ttactccttg accacctgag ccgtgtcctg ttaacctttg atggctttga cgagttcaag    1260
ttcaggttca cggatcgtga acgccactgc tccccgaccg accccacctc tgtccagacc    1320
ctgctcttca accttctgca gggcaacctg ctgaagaatg cccgcaaggt ggtgaccagc    1380
cgtccggccg ctgtgtcggc gttcctcagg aagtacatcc gcaccgagtt caacctcaag    1440
ggcttctctg aacagggcat cgagctgtac ctgaggaagc gccatcatga gcccgggtg    1500 gcggaccgcc tcatccgcct gctccaagag acctcagccc tgcacggttt gtgccacctg    1560
cctgtcttct catggatggt gtccaaatgc caccaggaac tgttgctgca ggaggggggg    1620
```

-continued

```
tccccaaaga ccactacaga tatgtacctg ctgattctgc agcattttct gctgcatgcc  1680
accccccag  actcagcttc ccaaggtctg ggacccagtc ttcttcgggg ccgcctcccc  1740
accctcctgc acctgggcag actggctctg tggggcctgg gcatgtgctg ctacgtgttc  1800
tcagcccagc agctccaggc agcacaggtc agccctgatg acatttctct tggcttcctg  1860
gtgcgtgcca aaggtgtcgt gccagggagt acggcgcccc tggaattcct tcacatcact  1920
ttccagtgct tctttgccgc gttctacctg gcactcagtg ctgatgtgcc accagctttg  1980
ctcagacacc tcttcaattg tggcaggcca ggcaactcac caatggccag gctcctgccc  2040
acgatgtgca tccaggcctc ggagggaaag acagcagcg tggcagcttt gctgcagaag  2100
gccgagccgc acaaccttca gatcacagca gccttcctgg cagggctgtt gtcccgggag  2160
cactggggcc tgctggctga gtccagaca tctgagaagg ccctgctccg cgccaggcc  2220
tgtgcccgct ggtgtctggc ccgcagcctc cgcaagcact ccactccat cccgccagct  2280
gcaccgggtg aggccaagag cgtgcatgcc atgcccgggt tcatctggct catccggagc  2340
ctgtacgaga tgcaggagga gcggctggct cggaaggctg cacgtggcct gaatgttggg  2400
cacctcaagt tgacatttg cagtgtgggc cccactgagt gtgctgccct ggcctttgtg  2460
ctgcagcacc tccggcggcc cgtggccctg cagctggact acaactctgt gggtgacatt  2520
ggcgtggagc agctgctgcc ttgccttggt gtctgcaagg ctctgtattt gcgcgataac  2580
aatatctcag accgaggcat ctgcaagctc attgaatgtg ctcttcactg cgagcaattg  2640
cagaagttag ctctattcaa caacaaattg actgacggct gtgcacactc catggctaag  2700
ctccttgcat gcaggcagaa cttcttggca ttgaggctgg ggataacta catcactgcc  2760
gcgggagccc aagtgctggc cgaggggctc cgaggcaaca cctccttgca gttcctggga  2820
ttctggggca acagagtggg tgacgagggg gcccaggccc tggctgaagc cttgggtgat  2880
caccagagct tgaggtggct cagcctggtg gggaacaaca ttggcagtgt gggtgcccaa  2940
gccttggcac tgatgctggc aaagaacgtc atgctagaag aactctgcct ggaggagaac  3000
catctccagg atgaaggtgt atgttctctc gcagaaggac tgaagaaaaa ttcaagtttg  3060
aaaatcctga agttgtccaa taactgcatc acctacctag gggcagaagc cctcctgcag  3120
gcccttgaaa ggaatgacac catcctggaa gtctggctcc gagggaacac tttctctcta  3180
gaggaggttg acaagctcgg ctgcagggac accagactct gctttgaag tctccgggag  3240
gatgttcgtc tcagtttgtt tgtgagcagg ctgtgagttt gggccccaga ggctgggtga  3300
catgtgttgg cagcctcttc aaaatgagcc ctgtcctgcc taaggctgaa cttgtttctt  3360
gggaacacca taggtcacct ttattctggc agaggaggga gcatcagtgc cctccaggat  3420
agacttttcc caagcctact tttgccattg acttcttccc aagattcaat cccaggatgt  3480
acaaggacag cccctcctcc atagtatggg actggcctct gctgatcctc ccaggcttcc  3540
gtgtgggtca gtgggccca tggatgtgct tgttaactga gtgccttttg gtggagaggc  3600
ccggcctctc acaaaagacc ccttaccact gctctgatga agaggagtac acagaacaca  3660
taattcagga agcagctttc cccatgtctc gactcatcca tccaggccat tccccgtctc  3720
tggttcctcc cctcctcctg gactcctgca cacgctcctt cctctgaggc tgaaattcag  3780
aatattagtg acctcagctt tgatatttca cttacagcac ccccaaccct ggcacccagg  3840
gtgggaaggg ctacacctta gcctgccctc ctttccggtg tttaagacat ttttggaagg  3900
ggacacgtga cagccgtttg ttccccaaga cattctaggt ttgcaagaaa aatatgacca  3960
```

-continued

```
cactccagct gggatcacat gtggactttt atttccagtg aaatcagtta ctcttcagtt    4020
aagcctttgg aaacagctcg actttaaaaa gctccaaatg cagctttaaa aaattaatct    4080
gggccagaat tcaaacggc ctcactaggc ttctggttga tgcctgtgaa ctgaactctg     4140
acaacagact tctgaaatag acccacaaga ggcagttcca tttcatttgt gccagaatgc    4200
tttaggatgt acagttatgg attgaaagtt tacaggaaaa aaaattaggc cgttccttca    4260
aagcaaatgt cttcctggat tattcaaaat gatgtatgtt gaagcctttg taaattgtca    4320
gatgctgtgc aaatgttatt attttaaaca ttatgatgtg tgaaaactgg ttaatattta    4380
taggtcactt tgttttactg tcttaagttt atactcttat agacaacatg gccgtgaact    4440
ttatgctgta aataatcaga ggggaataaa ctgttgagtc aaaac                    4485
```

<210> SEQ ID NO 2
<211> LENGTH: 1040
<212> TYPE: PRT
<213> ORGANISM: Homo sapiens

<400> SEQUENCE: 2

```
Met Gly Glu Glu Gly Gly Ser Ala Ser His Asp Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
        195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Pro Pro Gln Lys Ser
            260                 265                 270

Pro Ala Thr Leu Gly Leu Glu Glu Leu Phe Ser Thr Pro Gly His Leu
        275                 280                 285
```

```
Asn Asp Asp Ala Asp Thr Val Leu Val Gly Glu Ala Gly Ser Gly
    290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                    325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
            355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                    405                 410                 415

Lys Asn Ala Arg Lys Val Val Thr Ser Arg Pro Ala Ala Val Ser Ala
                420                 425                 430

Phe Leu Arg Lys Tyr Ile Arg Thr Glu Phe Asn Leu Lys Gly Phe Ser
            435                 440                 445

Glu Gln Gly Ile Glu Leu Tyr Leu Arg Lys Arg His His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                    485                 490                 495

Gln Glu Leu Leu Leu Gln Glu Gly Gly Ser Pro Lys Thr Thr Thr Asp
                500                 505                 510

Met Tyr Leu Leu Ile Leu Gln His Phe Leu Leu His Ala Thr Pro Pro
            515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
545                 550                 555                 560

Cys Cys Tyr Val Phe Ser Ala Gln Gln Leu Gln Ala Ala Gln Val Ser
                    565                 570                 575

Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
    595                 600                 605

Phe Phe Ala Ala Phe Tyr Leu Ala Leu Ser Ala Asp Val Pro Pro Ala
610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                    645                 650                 655

Ser Ser Val Ala Ala Leu Leu Gln Lys Ala Glu Pro His Asn Leu Gln
                660                 665                 670

Ile Thr Ala Ala Phe Leu Ala Gly Leu Leu Ser Arg Glu His Trp Gly
            675                 680                 685

Leu Leu Ala Glu Cys Gln Thr Ser Glu Lys Ala Leu Leu Arg Arg Gln
    690                 695                 700
```

```
Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
            725                 730                 735

Pro Gly Phe Ile Trp Leu Ile Arg Ser Leu Tyr Glu Met Gln Glu Glu
        740                 745                 750

Arg Leu Ala Arg Lys Ala Ala Arg Gly Leu Asn Val Gly His Leu Lys
    755                 760                 765

Leu Thr Phe Cys Ser Val Gly Pro Thr Glu Cys Ala Ala Leu Ala Phe
770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
            820                 825                 830

Cys Lys Leu Ile Glu Cys Ala Leu His Cys Glu Gln Leu Gln Lys Leu
        835                 840                 845

Ala Leu Phe Asn Asn Lys Leu Thr Asp Gly Cys Ala His Ser Met Ala
    850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
        915                 920                 925

Leu Arg Trp Leu Ser Leu Val Gly Asn Asn Ile Gly Ser Val Gly Ala
    930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
            980                 985                 990

Asn Cys Ile Thr Tyr Leu Gly Ala Glu Ala Leu Leu Gln Ala Leu Glu
        995                 1000                1005

Arg Asn Asp Thr Ile Leu Glu Val Trp Leu Arg Gly Asn Thr Phe
    1010                1015                1020

Ser Leu Glu Glu Val Asp Lys Leu Gly Cys Arg Asp Thr Arg Leu
    1025                1030                1035

Leu Leu
    1040

<210> SEQ ID NO 3
<211> LENGTH: 1013
<212> TYPE: PRT
<213> ORGANISM: Homo sapiens

<400> SEQUENCE: 3

Met Cys Ser Gln Glu Ala Phe Gln Ala Gln Arg Ser Gln Leu Val Glu
1               5                   10                  15

Leu Leu Val Ser Gly Ser Leu Glu Gly Phe Glu Ser Val Leu Asp Trp
            20                  25                  30
```

```
Leu Leu Ser Trp Glu Val Leu Ser Trp Glu Asp Tyr Glu Gly Phe His
         35                  40                  45

Leu Leu Gly Gln Pro Leu Ser His Leu Ala Arg Arg Leu Leu Asp Thr
     50                  55                  60

Val Trp Asn Lys Gly Thr Trp Ala Cys Gln Lys Leu Ile Ala Ala Ala
65                   70                  75                  80

Gln Glu Ala Gln Ala Asp Ser Gln Ser Pro Lys Leu His Gly Cys Trp
                 85                  90                  95

Asp Pro His Ser Leu His Pro Ala Arg Asp Leu Gln Ser His Arg Pro
             100                 105                 110

Ala Ile Val Arg Arg Leu His Ser His Val Glu Asn Met Leu Asp Leu
         115                 120                 125

Ala Trp Glu Arg Gly Phe Val Ser Gln Tyr Glu Cys Asp Glu Ile Arg
     130                 135                 140

Leu Pro Ile Phe Thr Pro Ser Gln Arg Ala Arg Arg Leu Leu Asp Leu
145                 150                 155                 160

Ala Thr Val Lys Ala Asn Gly Leu Ala Ala Phe Leu Leu Gln His Val
                 165                 170                 175

Gln Glu Leu Pro Val Pro Leu Ala Leu Pro Leu Glu Ala Ala Thr Cys
             180                 185                 190

Lys Lys Tyr Met Ala Lys Leu Arg Thr Thr Val Ser Ala Gln Ser Arg
         195                 200                 205

Phe Leu Ser Thr Tyr Asp Gly Ala Glu Thr Leu Cys Leu Glu Asp Ile
     210                 215                 220

Tyr Thr Glu Asn Val Leu Glu Val Trp Ala Asp Val Gly Met Ala Gly
225                 230                 235                 240

Pro Pro Gln Lys Ser Pro Ala Thr Leu Gly Leu Glu Glu Leu Phe Ser
                 245                 250                 255

Thr Pro Gly His Leu Asn Asp Asp Ala Asp Thr Val Leu Val Val Gly
             260                 265                 270

Glu Ala Gly Ser Gly Lys Ser Thr Leu Leu Gln Arg Leu His Leu Leu
         275                 280                 285

Trp Ala Ala Gly Gln Asp Phe Gln Glu Phe Leu Phe Val Phe Pro Phe
     290                 295                 300

Ser Cys Arg Gln Leu Gln Cys Met Ala Lys Pro Leu Ser Val Arg Thr
305                 310                 315                 320

Leu Leu Phe Glu His Cys Cys Trp Pro Asp Val Gly Gln Glu Asp Ile
                 325                 330                 335

Phe Gln Leu Leu Leu Asp His Pro Asp Arg Val Leu Leu Thr Phe Asp
             340                 345                 350

Gly Phe Asp Glu Phe Lys Phe Arg Phe Thr Asp Arg Glu Arg His Cys
         355                 360                 365

Ser Pro Thr Asp Pro Thr Ser Val Gln Thr Leu Leu Phe Asn Leu Leu
     370                 375                 380

Gln Gly Asn Leu Leu Lys Asn Ala Arg Lys Val Val Thr Ser Arg Pro
385                 390                 395                 400

Ala Ala Val Ser Ala Phe Leu Arg Lys Tyr Ile Arg Thr Glu Phe Asn
                 405                 410                 415

Leu Lys Gly Phe Ser Glu Gln Gly Ile Glu Leu Tyr Leu Arg Lys Arg
             420                 425                 430

His His Glu Pro Gly Val Ala Asp Arg Leu Ile Arg Leu Leu Gln Glu
         435                 440                 445
```

```
Thr Ser Ala Leu His Gly Leu Cys His Leu Pro Val Phe Ser Trp Met
    450                 455                 460

Val Ser Lys Cys His Gln Glu Leu Leu Gln Glu Gly Gly Ser Pro
465                 470                 475                 480

Lys Thr Thr Thr Asp Met Tyr Leu Leu Ile Leu Gln His Phe Leu Leu
                485                 490                 495

His Ala Thr Pro Pro Asp Ser Ala Ser Gln Gly Leu Gly Pro Ser Leu
                500                 505                 510

Leu Arg Gly Arg Leu Pro Thr Leu Leu His Leu Gly Arg Leu Ala Leu
            515                 520                 525

Trp Gly Leu Gly Met Cys Cys Tyr Val Phe Ser Ala Gln Gln Leu Gln
    530                 535                 540

Ala Ala Gln Val Ser Pro Asp Ile Ser Leu Gly Phe Leu Val Arg
545                 550                 555                 560

Ala Lys Gly Val Val Pro Gly Ser Thr Ala Pro Leu Glu Phe Leu His
                565                 570                 575

Ile Thr Phe Gln Cys Phe Phe Ala Ala Phe Tyr Leu Ala Leu Ser Ala
                580                 585                 590

Asp Val Pro Pro Ala Leu Leu Arg His Leu Phe Asn Cys Gly Arg Pro
            595                 600                 605

Gly Asn Ser Pro Met Ala Arg Leu Leu Pro Thr Met Cys Ile Gln Ala
    610                 615                 620

Ser Glu Gly Lys Asp Ser Ser Val Ala Ala Leu Leu Gln Lys Ala Glu
625                 630                 635                 640

Pro His Asn Leu Gln Ile Thr Ala Ala Phe Leu Ala Gly Leu Leu Ser
                645                 650                 655

Arg Glu His Trp Gly Leu Leu Ala Glu Cys Gln Thr Ser Glu Lys Ala
                660                 665                 670

Leu Leu Arg Arg Gln Ala Cys Ala Arg Trp Cys Leu Ala Arg Ser Leu
            675                 680                 685

Arg Lys His Phe His Ser Ile Pro Pro Ala Ala Pro Gly Glu Ala Lys
    690                 695                 700

Ser Val His Ala Met Pro Gly Phe Ile Trp Leu Ile Arg Ser Leu Tyr
705                 710                 715                 720

Glu Met Gln Glu Glu Arg Leu Ala Arg Lys Ala Ala Arg Gly Leu Asn
                725                 730                 735

Val Gly His Leu Lys Leu Thr Phe Cys Ser Val Gly Pro Thr Glu Cys
                740                 745                 750

Ala Ala Leu Ala Phe Val Leu Gln His Leu Arg Arg Pro Val Ala Leu
            755                 760                 765

Gln Leu Asp Tyr Asn Ser Val Gly Asp Ile Gly Val Glu Gln Leu Leu
    770                 775                 780

Pro Cys Leu Gly Val Cys Lys Ala Leu Tyr Leu Arg Asp Asn Asn Ile
785                 790                 795                 800

Ser Asp Arg Gly Ile Cys Lys Leu Ile Glu Cys Ala Leu His Cys Glu
                805                 810                 815

Gln Leu Gln Lys Leu Ala Leu Phe Asn Asn Lys Leu Thr Asp Gly Cys
                820                 825                 830

Ala His Ser Met Ala Lys Leu Leu Ala Cys Arg Gln Asn Phe Leu Ala
            835                 840                 845

Leu Arg Leu Gly Asn Asn Tyr Ile Thr Ala Ala Gly Ala Gln Val Leu
    850                 855                 860

Ala Glu Gly Leu Arg Gly Asn Thr Ser Leu Gln Phe Leu Gly Phe Trp
```

```
                865                 870                 875                 880

Gly Asn Arg Val Gly Asp Glu Gly Ala Gln Ala Leu Ala Glu Ala Leu
                        885                 890                 895

Gly Asp His Gln Ser Leu Arg Trp Leu Ser Leu Val Gly Asn Asn Ile
                    900                 905                 910

Gly Ser Val Gly Ala Gln Ala Leu Ala Leu Met Leu Ala Lys Asn Val
                    915                 920                 925

Met Leu Glu Glu Leu Cys Leu Glu Asn His Leu Gln Asp Glu Gly
                930                 935                 940

Val Cys Ser Leu Ala Glu Gly Leu Lys Lys Asn Ser Ser Leu Lys Ile
        945                 950                 955                 960

Leu Lys Leu Ser Asn Asn Cys Ile Thr Tyr Leu Gly Ala Glu Ala Leu
                        965                 970                 975

Leu Gln Ala Leu Glu Arg Asn Asp Thr Ile Leu Glu Val Trp Leu Arg
                        980                 985                 990

Gly Asn Thr Phe Ser Leu Glu Glu  Val Asp Lys Leu Gly  Cys Arg Asp
                        995                 1000                1005

Thr Arg  Leu Leu Leu
            1010

<210> SEQ ID NO 4
<211> LENGTH: 1040
<212> TYPE: PRT
<213> ORGANISM: Homo sapiens

<400> SEQUENCE: 4

Met Gly Glu Glu Gly Gly Ser Ala Ser His Asp Glu Glu Arg Ala
1               5                   10                  15

Ser Val Leu Leu Gly His Ser Pro Gly Cys Glu Met Cys Ser Gln Glu
                20                  25                  30

Ala Phe Gln Ala Gln Arg Ser Gln Leu Val Glu Leu Leu Val Ser Gly
            35                  40                  45

Ser Leu Glu Gly Phe Glu Ser Val Leu Asp Trp Leu Leu Ser Trp Glu
        50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                    85                  90                  95

Thr Trp Ala Cys Gln Lys Leu Ile Ala Ala Ala Gln Glu Ala Gln Ala
                100                 105                 110

Asp Ser Gln Ser Pro Lys Leu His Gly Cys Trp Asp Pro His Ser Leu
            115                 120                 125

His Pro Ala Arg Asp Leu Gln Ser His Arg Pro Ala Ile Val Arg Arg
        130                 135                 140

Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                    165                 170                 175

Pro Ser Gln Arg Ala Arg Arg Leu Leu Asp Leu Ala Thr Val Lys Ala
                180                 185                 190

Asn Gly Leu Ala Ala Phe Leu Leu Gln His Val Gln Glu Leu Pro Val
            195                 200                 205

Pro Leu Ala Leu Pro Leu Glu Ala Ala Thr Cys Lys Lys Tyr Met Ala
        210                 215                 220
```

```
Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
            245                 250                 255

Leu Glu Val Trp Ala Asp Val Gly Met Ala Gly Pro Pro Gln Lys Ser
        260                 265                 270

Pro Ala Thr Leu Gly Leu Glu Glu Leu Phe Ser Thr Pro Gly His Leu
    275                 280                 285

Asn Asp Asp Ala Asp Thr Val Leu Val Val Gly Glu Ala Gly Ser Gly
290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
            325                 330                 335

Gln Cys Met Ala Lys Pro Leu Ser Val Arg Thr Leu Leu Phe Glu His
        340                 345                 350

Cys Cys Trp Pro Asp Val Gly Gln Glu Asp Ile Phe Gln Leu Leu Leu
    355                 360                 365

Asp His Pro Asp Arg Val Leu Leu Thr Phe Asp Gly Phe Asp Glu Phe
370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
            405                 410                 415

Lys Asn Ala Arg Lys Val Val Thr Ser Arg Pro Ala Ala Val Ser Ala
        420                 425                 430

Phe Leu Arg Lys Tyr Ile Arg Thr Glu Phe Asn Leu Lys Gly Phe Ser
    435                 440                 445

Glu Gln Gly Ile Glu Leu Tyr Leu Arg Lys His His Glu Pro Gly
450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
            485                 490                 495

Gln Glu Leu Leu Leu Gln Glu Gly Gly Ser Pro Lys Thr Thr Thr Asp
        500                 505                 510

Met Tyr Leu Leu Ile Leu Gln His Phe Leu Leu His Ala Thr Pro Pro
    515                 520                 525

Asp Ser Ala Ser Gln Gly Leu Gly Pro Ser Leu Leu Arg Gly Arg Leu
530                 535                 540

Pro Thr Leu Leu His Leu Gly Arg Leu Ala Leu Trp Gly Leu Gly Met
545                 550                 555                 560

Cys Cys Tyr Val Phe Ser Ala Gln Gln Leu Gln Ala Ala Gln Val Ser
            565                 570                 575

Pro Asp Asp Ile Ser Leu Gly Phe Leu Val Arg Ala Lys Gly Val Val
        580                 585                 590

Pro Gly Ser Thr Ala Pro Leu Glu Phe Leu His Ile Thr Phe Gln Cys
    595                 600                 605

Phe Phe Ala Ala Phe Tyr Leu Ala Leu Ser Ala Asp Val Pro Pro Ala
610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
```

-continued

```
                645                 650                 655
Ser Ser Val Ala Ala Leu Leu Gln Lys Ala Glu Pro His Asn Leu Gln
            660                 665                 670
Ile Thr Ala Ala Phe Leu Ala Gly Leu Leu Ser Arg Glu His Trp Gly
            675                 680                 685
Leu Leu Ala Glu Cys Gln Thr Ser Glu Lys Ala Leu Leu Arg His Gln
            690                 695                 700
Ala Cys Ala Arg Trp Cys Leu Ala Arg Ser Leu Arg Lys His Phe His
705                 710                 715                 720
Ser Ile Pro Pro Ala Ala Pro Gly Glu Ala Lys Ser Val His Ala Met
            725                 730                 735
Pro Gly Phe Ile Trp Leu Ile Arg Ser Leu Tyr Glu Met Gln Glu Glu
            740                 745                 750
Arg Leu Ala Arg Lys Ala Ala Arg Gly Leu Asn Val Gly His Leu Lys
            755                 760                 765
Leu Thr Phe Cys Ser Val Gly Pro Thr Glu Cys Ala Ala Leu Ala Phe
            770                 775                 780
Val Leu Gln His Leu Arg Arg Pro Val Ala Leu Gln Leu Asp Tyr Asn
785                 790                 795                 800
Ser Val Gly Asp Ile Gly Val Glu Gln Leu Leu Pro Cys Leu Gly Val
            805                 810                 815
Cys Lys Ala Leu Tyr Leu Arg Asp Asn Asn Ile Ser Asp Arg Gly Ile
            820                 825                 830
Cys Lys Leu Ile Glu Cys Ala Leu His Cys Glu Gln Leu Gln Lys Leu
            835                 840                 845
Ala Leu Phe Asn Asn Lys Leu Thr Asp Gly Cys Ala His Ser Met Ala
850                 855                 860
Lys Leu Leu Ala Cys Arg Gln Asn Phe Leu Ala Leu Arg Leu Gly Asn
865                 870                 875                 880
Asn Tyr Ile Thr Ala Ala Gly Ala Gln Val Leu Ala Glu Gly Leu Arg
            885                 890                 895
Gly Asn Thr Ser Leu Gln Phe Leu Gly Phe Trp Gly Asn Arg Val Gly
            900                 905                 910
Asp Glu Gly Ala Gln Ala Leu Ala Glu Ala Leu Gly Asp His Gln Ser
            915                 920                 925
Leu Arg Trp Leu Ser Leu Val Gly Asn Asn Ile Gly Ser Val Gly Ala
            930                 935                 940
Gln Ala Leu Ala Leu Met Leu Ala Lys Asn Val Met Leu Glu Glu Leu
945                 950                 955                 960
Cys Leu Glu Glu Asn His Leu Gln Asp Glu Gly Val Cys Ser Leu Ala
                    965                 970                 975
Glu Gly Leu Lys Lys Asn Ser Ser Leu Lys Ile Leu Lys Leu Ser Asn
            980                 985                 990
Asn Cys Ile Thr Tyr Leu Gly Ala  Glu Ala Leu Leu Gln Ala Leu Glu
            995                 1000                 1005
Arg Asn Asp Thr Ile Leu Glu  Val Trp Leu Arg Gly  Asn Thr Phe
1010                 1015                 1020
Ser Leu Glu Glu Val Asp Lys  Leu Gly Cys Arg Asp   Thr Arg Leu
1025                 1030                 1035
Leu Leu
1040
```

<210> SEQ ID NO 5

```
<211> LENGTH: 97
<212> TYPE: PRT
<213> ORGANISM: Homo sapiens

<400> SEQUENCE: 5

Met Cys Ser Gln Glu Ala Phe Gln Ala Gln Arg Ser Gln Leu Val Glu
1               5                   10                  15

Leu Leu Val Ser Gly Ser Leu Glu Gly Phe Glu Ser Val Leu Asp Trp
            20                  25                  30

Leu Leu Ser Trp Glu Val Leu Ser Trp Glu Asp Tyr Glu Gly Phe His
        35                  40                  45

Leu Leu Gly Gln Pro Leu Ser His Leu Ala Arg Arg Leu Leu Asp Thr
    50                  55                  60

Val Trp Asn Lys Gly Thr Trp Ala Cys Gln Lys Leu Ile Ala Ala Ala
65                  70                  75                  80

Gln Glu Ala Gln Ala Asp Ser Gln Ser Pro Lys Leu His Gly Cys Trp
                85                  90                  95

Asp

<210> SEQ ID NO 6
<211> LENGTH: 94
<212> TYPE: PRT
<213> ORGANISM: Homo sapiens

<400> SEQUENCE: 6

Ser Leu His Pro Ala Arg Asp Leu Gln Ser His Arg Pro Ala Ile Val
1               5                   10                  15

Arg Arg Leu His Ser His Val Glu Asn Met Leu Asp Leu Ala Trp Glu
            20                  25                  30

Arg Gly Phe Val Ser Gln Tyr Glu Cys Asp Glu Ile Arg Leu Pro Ile
        35                  40                  45

Phe Thr Pro Ser Gln Arg Ala Arg Arg Leu Leu Asp Leu Ala Thr Val
    50                  55                  60

Lys Ala Asn Gly Leu Ala Ala Phe Leu Leu Gln His Val Gln Glu Leu
65                  70                  75                  80

Pro Val Pro Leu Ala Leu Pro Leu Glu Ala Ala Thr Cys Lys
                85                  90

<210> SEQ ID NO 7
<211> LENGTH: 305
<212> TYPE: PRT
<213> ORGANISM: Homo sapiens

<400> SEQUENCE: 7

Pro Ala Thr Leu Gly Leu Glu Glu Leu Phe Ser Thr Pro Gly His Leu
1               5                   10                  15

Asn Asp Asp Ala Asp Thr Val Leu Val Val Gly Glu Ala Gly Ser Gly
            20                  25                  30

Lys Ser Thr Leu Leu Gln Arg Leu His Leu Leu Trp Ala Ala Gly Gln
        35                  40                  45

Asp Phe Gln Glu Phe Leu Phe Val Phe Pro Phe Ser Cys Arg Gln Leu
    50                  55                  60

Gln Cys Met Ala Lys Pro Leu Ser Val Arg Thr Leu Leu Phe Glu His
65                  70                  75                  80

Cys Cys Trp Pro Asp Val Gly Gln Glu Asp Ile Phe Gln Leu Leu Leu
                85                  90                  95

Asp His Pro Asp Arg Val Leu Leu Thr Phe Asp Gly Phe Asp Glu Phe
```

```
            100                 105                 110
Lys Phe Arg Phe Thr Asp Arg Glu Arg His Cys Ser Pro Thr Asp Pro
            115                 120                 125
Thr Ser Val Gln Thr Leu Leu Phe Asn Leu Leu Gln Gly Asn Leu Leu
        130                 135                 140
Lys Asn Ala Arg Lys Val Val Thr Ser Arg Pro Ala Ala Val Ser Ala
145                 150                 155                 160
Phe Leu Arg Lys Tyr Ile Arg Thr Glu Phe Asn Leu Lys Gly Phe Ser
                165                 170                 175
Glu Gln Gly Ile Glu Leu Tyr Leu Arg Lys Arg His His Glu Pro Gly
            180                 185                 190
Val Ala Asp Arg Leu Ile Arg Leu Leu Gln Glu Thr Ser Ala Leu His
            195                 200                 205
Gly Leu Cys His Leu Pro Val Phe Ser Trp Met Val Ser Lys Cys His
        210                 215                 220
Gln Glu Leu Leu Leu Gln Glu Gly Gly Ser Pro Lys Thr Thr Thr Asp
225                 230                 235                 240
Met Tyr Leu Leu Ile Leu Gln His Phe Leu Leu His Ala Thr Pro Pro
                245                 250                 255
Asp Ser Ala Ser Gln Gly Leu Gly Pro Ser Leu Leu Arg Gly Arg Leu
            260                 265                 270
Pro Thr Leu Leu His Leu Gly Arg Leu Ala Leu Trp Gly Leu Gly Met
            275                 280                 285
Cys Cys Tyr Val Phe Ser Ala Gln Gln Leu Gln Ala Ala Gln Val Ser
        290                 295                 300
Pro
305

<210> SEQ ID NO 8
<211> LENGTH: 28
<212> TYPE: PRT
<213> ORGANISM: Homo sapiens

<400> SEQUENCE: 8

Arg Ser Leu Tyr Glu Met Gln Glu Glu Arg Leu Ala Arg Lys Ala Ala
1               5                   10                  15
Arg Gly Leu Asn Val Gly His Leu Lys Leu Thr Phe
            20                  25

<210> SEQ ID NO 9
<211> LENGTH: 28
<212> TYPE: PRT
<213> ORGANISM: Homo sapiens

<400> SEQUENCE: 9

Cys Ser Val Gly Pro Thr Glu Cys Ala Ala Leu Ala Phe Val Leu Gln
1               5                   10                  15
His Leu Arg Arg Pro Val Ala Leu Gln Leu Asp Tyr
            20                  25

<210> SEQ ID NO 10
<211> LENGTH: 25
<212> TYPE: PRT
<213> ORGANISM: Homo sapiens

<400> SEQUENCE: 10

Asn Ser Val Gly Asp Ile Gly Val Glu Gln Leu Leu Pro Cys Leu Gly
1               5                   10                  15
```

```
Val Cys Lys Ala Leu Tyr Leu Arg Asp
            20                  25
```

<210> SEQ ID NO 11
<211> LENGTH: 28
<212> TYPE: PRT
<213> ORGANISM: Homo sapiens

<400> SEQUENCE: 11

```
Asn Asn Ile Ser Asp Arg Gly Ile Cys Lys Leu Ile Glu Cys Ala Leu
1               5                   10                  15

His Cys Glu Gln Leu Gln Lys Leu Ala Leu Phe Asn
            20                  25
```

<210> SEQ ID NO 12
<211> LENGTH: 28
<212> TYPE: PRT
<213> ORGANISM: Homo sapiens

<400> SEQUENCE: 12

```
Asn Lys Leu Thr Asp Gly Cys Ala His Ser Met Ala Lys Leu Leu Ala
1               5                   10                  15

Cys Arg Gln Asn Phe Leu Ala Leu Arg Leu Gly Asn
            20                  25
```

<210> SEQ ID NO 13
<211> LENGTH: 28
<212> TYPE: PRT
<213> ORGANISM: Homo sapiens

<400> SEQUENCE: 13

```
Asn Tyr Ile Thr Ala Ala Gly Ala Gln Val Leu Ala Glu Gly Leu Arg
1               5                   10                  15

Gly Asn Thr Ser Leu Gln Phe Leu Gly Phe Trp Gly
            20                  25
```

<210> SEQ ID NO 14
<211> LENGTH: 28
<212> TYPE: PRT
<213> ORGANISM: Homo sapiens

<400> SEQUENCE: 14

```
Asn Arg Val Gly Asp Glu Gly Ala Gln Ala Leu Ala Glu Ala Leu Gly
1               5                   10                  15

Asp His Gln Ser Leu Arg Trp Leu Ser Leu Val Gly
            20                  25
```

<210> SEQ ID NO 15
<211> LENGTH: 28
<212> TYPE: PRT
<213> ORGANISM: Homo sapiens

<400> SEQUENCE: 15

```
Asn Asn Ile Gly Ser Val Gly Ala Gln Ala Leu Ala Leu Met Leu Ala
1               5                   10                  15

Lys Asn Val Met Leu Glu Glu Leu Cys Leu Glu Glu
            20                  25
```

<210> SEQ ID NO 16
<211> LENGTH: 28
<212> TYPE: PRT
<213> ORGANISM: Homo sapiens

```
<400> SEQUENCE: 16

Asn His Leu Gln Asp Glu Gly Val Cys Ser Leu Ala Glu Gly Leu Lys
1               5                   10                  15

Lys Asn Ser Ser Leu Lys Ile Leu Lys Leu Ser Asn
            20                  25

<210> SEQ ID NO 17
<211> LENGTH: 28
<212> TYPE: PRT
<213> ORGANISM: Homo sapiens

<400> SEQUENCE: 17

Asn Cys Ile Thr Tyr Leu Gly Ala Glu Ala Leu Leu Gln Ala Leu Glu
1               5                   10                  15

Arg Asn Asp Thr Ile Leu Glu Val Trp Leu Arg Gly
            20                  25

<210> SEQ ID NO 18
<211> LENGTH: 7
<212> TYPE: PRT
<213> ORGANISM: Homo sapiens

<400> SEQUENCE: 18

Glu Ala Gly Ser Gly Lys Ser
1               5

<210> SEQ ID NO 19
<211> LENGTH: 5
<212> TYPE: PRT
<213> ORGANISM: Homo sapiens

<400> SEQUENCE: 19

Leu Leu Thr Phe Asp
1               5

<210> SEQ ID NO 20
<211> LENGTH: 92
<212> TYPE: PRT
<213> ORGANISM: Homo sapiens

<400> SEQUENCE: 20

Glu Ser His Pro His Ile Gln Leu Leu Lys Ser Asn Arg Glu Leu Leu
1               5                   10                  15

Val Thr His Ile Arg Asn Thr Gln Cys Leu Val Asp Asn Leu Leu Lys
            20                  25                  30

Asn Asp Tyr Phe Ser Ala Glu Asp Ala Glu Ile Val Cys Ala Cys Pro
        35                  40                  45

Thr Gln Pro Asp Lys Val Arg Lys Ile Leu Asp Leu Val Gln Ser Lys
    50                  55                  60

Gly Glu Glu Val Ser Glu Phe Phe Leu Tyr Leu Gln Gln Leu Ala
65                  70                  75                  80

Asp Ala Tyr Val Asp Leu Arg Pro Trp Leu Leu Glu
                85                  90

<210> SEQ ID NO 21
<211> LENGTH: 92
<212> TYPE: PRT
<213> ORGANISM: Homo sapiens

<400> SEQUENCE: 21
```

```
Gly Ile Ala Gln Gln Trp Ile Gln Ser Lys Arg Glu Asp Ile Val Asn
1               5                   10                  15

Gln Met Thr Glu Ala Cys Leu Asn Gln Ser Leu Asp Ala Leu Leu Ser
            20                  25                  30

Arg Asp Leu Ile Met Lys Glu Asp Tyr Glu Leu Val Ser Thr Lys Pro
            35                  40                  45

Thr Arg Thr Ser Lys Val Arg Gln Leu Leu Asp Thr Thr Asp Ile Gln
        50                  55                  60

Gly Glu Glu Phe Ala Lys Val Ile Val Gln Lys Leu Lys Asp Asn Lys
65                  70                  75                  80

Gln Met Gly Leu Gln Pro Tyr Pro Glu Ile Leu Val
            85                  90
```

<210> SEQ ID NO 22
<211> LENGTH: 93
<212> TYPE: PRT
<213> ORGANISM: Homo sapiens

<400> SEQUENCE: 22

```
Glu Arg Pro Ser Glu Thr Ile Asp Arg Glu Arg Lys Arg Leu Val Glu
1               5                   10                  15

Thr Leu Gln Ala Asp Ser Gly Leu Leu Leu Asp Ala Leu Val Ala Arg
            20                  25                  30

Gly Val Leu Thr Gly Pro Glu Tyr Glu Ala Leu Asp Ala Leu Pro Asp
            35                  40                  45

Ala Glu Arg Arg Val Arg Arg Leu Leu Leu Leu Val Gln Ser Lys Gly
        50                  55                  60

Glu Ala Ala Cys Gln Glu Leu Leu Arg Cys Ala Gln Gln Thr Val Ser
65                  70                  75                  80

Met Pro Asp Pro Ala Trp Asp Trp Gln His Val Gly Pro
            85                  90
```

<210> SEQ ID NO 23
<211> LENGTH: 94
<212> TYPE: PRT
<213> ORGANISM: Homo sapiens

<400> SEQUENCE: 23

```
Met Glu Ala Arg Asp Lys Gln Val Leu Arg Ser Leu Arg Leu Glu Leu
1               5                   10                  15

Gly Ala Glu Val Leu Val Glu Gly Leu Val Leu Gln Tyr Leu Tyr Gln
            20                  25                  30

Glu Gly Ile Leu Thr Glu Asn His Ile Gln Glu Ile Asn Ala Gln Thr
            35                  40                  45

Thr Gly Leu Arg Lys Thr Met Leu Leu Leu Asp Ile Leu Pro Ser Arg
        50                  55                  60

Gly Pro Lys Ala Phe Asp Thr Phe Leu Asp Ser Leu Gln Glu Phe Pro
65                  70                  75                  80

Trp Val Arg Glu Lys Leu Lys Lys Ala Arg Glu Glu Ala Met
            85                  90
```

<210> SEQ ID NO 24
<211> LENGTH: 91
<212> TYPE: PRT
<213> ORGANISM: Homo sapiens

<400> SEQUENCE: 24

Met His Pro His His Gln Glu Thr Leu Lys Lys Asn Arg Val Val Leu

```
                  1               5                  10                 15

Ala Lys Gln Leu Leu Ser Glu Leu Glu His Leu Leu Glu Lys
              20                  25                 30

Asp Ile Ile Thr Leu Glu Met Arg Glu Leu Ile Gln Ala Lys Val Gly
              35                  40                 45

Ser Phe Ser Gln Asn Val Glu Leu Leu Asn Leu Leu Pro Lys Arg Gly
 50                  55                 60

Pro Gln Ala Phe Asp Ala Phe Cys Glu Ala Leu Arg Glu Thr Lys Gln
 65                  70                 75                    80

Gly His Leu Glu Asp Met Leu Leu Thr Thr Leu
              85                  90

<210> SEQ ID NO 25
<211> LENGTH: 91
<212> TYPE: PRT
<213> ORGANISM: Homo sapiens

<400> SEQUENCE: 25

Met Arg Gln Asp Arg Arg Ser Leu Leu Glu Arg Asn Ile Met Met Phe
 1                5                  10                 15

Ser Ser His Leu Lys Val Asp Glu Ile Leu Glu Val Leu Ile Ala Lys
              20                  25                 30

Gln Val Leu Asn Ser Asp Asn Gly Asp Met Ile Asn Ser Cys Gly Thr
              35                  40                 45

Val Arg Glu Lys Arg Arg Glu Ile Val Lys Ala Val Gln Arg Arg Gly
 50                  55                 60

Asp Val Ala Phe Asp Ala Phe Tyr Asp Ala Leu Arg Ser Thr Gly His
 65                  70                 75                    80

Glu Gly Leu Ala Glu Val Leu Glu Pro Leu Ala
              85                  90

<210> SEQ ID NO 26
<211> LENGTH: 90
<212> TYPE: PRT
<213> ORGANISM: Homo sapiens

<400> SEQUENCE: 26

Leu Cys Glu Ile Glu Cys Arg Ala Leu Ser Thr Ala His Thr Arg Leu
 1                5                  10                 15

Ile His Asp Phe Glu Pro Arg Asp Ala Leu Thr Tyr Leu Glu Gly Lys
              20                  25                 30

Asn Ile Phe Thr Glu Asp His Ser Glu Leu Ile Ser Lys Met Ser Thr
              35                  40                 45

Arg Leu Glu Arg Ile Ala Asn Phe Leu Arg Ile Tyr Arg Arg Gln Ala
              50                  55                 60

Ser Glu Leu Gly Pro Leu Ile Asp Phe Phe Asn Tyr Asn Asn Gln Ser
 65                  70                 75                    80

His Leu Ala Asp Phe Leu Glu Asp Tyr Ile
              85                  90

<210> SEQ ID NO 27
<211> LENGTH: 93
<212> TYPE: PRT
<213> ORGANISM: Homo sapiens

<400> SEQUENCE: 27

Met Asp Glu Ala Asp Arg Arg Leu Leu Arg Arg Cys Arg Leu Arg Leu
 1                5                  10                 15
```

```
Val Glu Glu Leu Gln Val Asp Gln Leu Trp Asp Val Leu Leu Ser Arg
             20                  25                  30

Glu Leu Phe Arg Pro His Met Ile Glu Asp Ile Gln Arg Ala Gly Ser
             35                  40                  45

Gly Ser Arg Arg Asp Gln Ala Arg Gln Leu Ile Ile Asp Leu Glu Thr
     50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg
                 85                  90

<210> SEQ ID NO 28
<211> LENGTH: 93
<212> TYPE: PRT
<213> ORGANISM: Homo sapiens

<400> SEQUENCE: 28

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
             20                  25                  30

Gly Phe Leu Thr Ile Ser Glu Glu Lys Val Arg Asn Glu Pro Thr
             35                  40                  45

Gln Gln Gln Arg Ala Ala Met Leu Ile Lys Met Ile Leu Lys Lys Asp
     50                  55                  60

Asn Asp Ser Tyr Val Ser Phe Tyr Asn Ala Leu His Glu Gly Tyr
65                  70                  75                  80

Lys Asp Leu Ala Ala Leu Leu His Asp Gly Ile Pro Val
                 85                  90

<210> SEQ ID NO 29
<211> LENGTH: 92
<212> TYPE: PRT
<213> ORGANISM: Homo sapiens

<400> SEQUENCE: 29

Met Ala Ser Asp Asp Leu Ser Leu Ile Arg Lys Asn Arg Met Ala Leu
1               5                   10                  15

Phe Gln Gln Leu Thr Cys Val Leu Pro Ile Leu Asp Asn Leu Leu Lys
             20                  25                  30

Ala Asn Val Ile Asn Lys Gln Glu His Asp Ile Ile Lys Gln Lys Thr
             35                  40                  45

Gln Ile Pro Leu Gln Ala Arg Glu Leu Ile Asp Thr Ile Trp Val Lys
     50                  55                  60

Gly Asn Ala Ala Asn Ile Phe Lys Asn Cys Leu Lys Glu Ile Asp
65                  70                  75                  80

Ser Thr Leu Tyr Lys Asn Leu Phe Val Asp Lys Asn
                 85                  90

<210> SEQ ID NO 30
<211> LENGTH: 320
<212> TYPE: PRT
<213> ORGANISM: Homo sapiens

<400> SEQUENCE: 30

Asn Glu Ser Leu Gly Ser Leu Asn Ser Leu Ala Cys Leu Leu Asp His
1               5                   10                  15
```

Thr Thr Gly Ile Leu Asn Glu Gln Gly Glu Thr Ile Phe Ile Leu Gly
            20                  25                  30

Asp Ala Gly Val Gly Lys Ser Met Leu Leu Gln Arg Leu Gln Ser Leu
            35                  40                  45

Trp Ala Thr Gly Arg Leu Asp Ala Gly Val Lys Phe Phe Phe His Phe
50                      55                  60

Arg Cys Arg Met Phe Ser Cys Phe Lys Glu Ser Asp Arg Leu Cys Leu
65                  70                  75                  80

Gln Asp Leu Leu Phe Lys His Tyr Cys Tyr Pro Glu Arg Asp Pro Glu
                85                  90                  95

Glu Val Phe Ala Phe Leu Leu Arg Phe Pro His Val Ala Leu Phe Thr
            100                 105                 110

Phe Asp Gly Leu Asp Glu Leu His Ser Asp Leu Asp Leu Ser Arg Val
            115                 120                 125

Pro Asp Ser Ser Cys Pro Trp Glu Pro Ala His Pro Leu Val Leu Leu
130                     135                 140

Ala Asn Leu Leu Ser Gly Lys Leu Leu Lys Gly Ala Ser Lys Leu Leu
145                 150                 155                 160

Thr Ala Arg Thr Gly Ile Glu Val Pro Arg Gln Phe Leu Arg Lys Lys
                165                 170                 175

Val Leu Leu Arg Gly Phe Ser Pro Ser His Leu Arg Ala Tyr Ala Arg
            180                 185                 190

Arg Met Phe Pro Glu Arg Ala Leu Gln Asp Arg Leu Leu Ser Gln Leu
            195                 200                 205

Glu Ala Asn Pro Asn Leu Cys Ser Leu Cys Ser Val Pro Leu Phe Cys
210                 215                 220

Trp Ile Ile Phe Arg Cys Phe Gln His Phe Arg Ala Ala Phe Glu Gly
225                 230                 235                 240

Ser Pro Gln Leu Pro Asp Cys Thr Met Thr Leu Thr Asp Val Phe Val
                245                 250                 255

Leu Val Thr Glu Val His Leu Asn Arg Met Gln Pro Ser Ser Leu Val
            260                 265                 270

Gln Arg Asn Thr Arg Ser Pro Val Glu Thr Leu His Ala Gly Arg Asp
            275                 280                 285

Thr Leu Cys Ser Leu Gly Gln Val Ala His Arg Gly Met Glu Lys Ser
290                 295                 300

Leu Phe Val Phe Thr Gln Glu Val Gln Ala Ser Gly Leu Gln Glu
305                 310                 315                 320

<210> SEQ ID NO 31
<211> LENGTH: 308
<212> TYPE: PRT
<213> ORGANISM: Homo sapiens

<400> SEQUENCE: 31

Pro Val Val Phe Val Thr Arg Lys Lys Leu Val Asn Ala Ile Gln Gln
1               5                   10                  15

Lys Leu Ser Lys Leu Lys Gly Glu Pro Gly Trp Val Thr Ile His Gly
            20                  25                  30

Met Ala Gly Cys Gly Lys Ser Val Leu Ala Ala Glu Ala Val Arg Asp
            35                  40                  45

His Ser Leu Leu Glu Gly Cys Phe Pro Gly Gly Val His Trp Val Ser
        50                  55                  60

Val Gly Lys Gln Asp Lys Ser Gly Leu Leu Met Lys Leu Gln Asn Leu
65                  70                  75                  80

```
Cys Thr Arg Leu Asp Gln Asp Glu Ser Phe Ser Gln Arg Leu Pro Leu
                85                  90                  95

Asn Ile Glu Glu Ala Lys Asp Arg Leu Arg Ile Leu Met Leu Arg Lys
            100                 105                 110

His Pro Arg Ser Leu Leu Ile Leu Asp Asp Val Trp Asp Ser Trp Val
        115                 120                 125

Leu Lys Ala Phe Asp Ser Gln Cys Gln Ile Leu Leu Thr Thr Arg Asp
    130                 135                 140

Lys Ser Val Thr Asp Ser Val Met Gly Pro Lys Tyr Val Pro Val
145                 150                 155                 160

Glu Ser Ser Leu Gly Lys Glu Lys Gly Leu Glu Ile Leu Ser Leu Phe
                165                 170                 175

Val Asn Met Lys Lys Ala Asp Leu Pro Glu Gln Ala His Ser Ile Ile
            180                 185                 190

Lys Glu Cys Lys Gly Ser Pro Leu Val Val Ser Leu Ile Gly Ala Leu
        195                 200                 205

Leu Arg Asp Phe Pro Asn Arg Trp Glu Tyr Tyr Leu Lys Gln Leu Gln
    210                 215                 220

Asn Lys Gln Phe Lys Arg Ile Arg Lys Ser Ser Ser Tyr Asp Tyr Glu
225                 230                 235                 240

Ala Leu Asp Glu Ala Met Ser Ile Ser Val Glu Met Leu Arg Glu Asp
                245                 250                 255

Ile Lys Asp Tyr Tyr Thr Asp Leu Ser Ile Leu Gln Lys Asp Val Lys
            260                 265                 270

Val Pro Thr Lys Val Leu Cys Ile Leu Trp Asp Met Glu Thr Glu Glu
        275                 280                 285

Val Glu Asp Ile Leu Gln Glu Phe Val Asn Lys Ser Leu Leu Phe Cys
    290                 295                 300

Asp Arg Asn Gly
305

<210> SEQ ID NO 32
<211> LENGTH: 315
<212> TYPE: PRT
<213> ORGANISM: Homo sapiens

<400> SEQUENCE: 32

Met Thr Cys Tyr Ile Arg Glu Tyr His Val Asp Arg Val Ile Lys Lys
1               5                   10                  15

Leu Asp Glu Met Cys Asp Leu Asp Ser Phe Phe Leu Phe Leu His Gly
                20                  25                  30

Arg Ala Gly Ser Gly Lys Ser Val Ile Ala Ser Gln Ala Leu Ser Lys
            35                  40                  45

Ser Asp Gln Leu Ile Gly Ile Asn Tyr Asp Ser Ile Val Trp Leu Lys
    50                  55                  60

Asp Ser Gly Thr Ala Pro Lys Ser Thr Phe Asp Leu Phe Thr Asp Ile
65                  70                  75                  80

Leu Leu Met Leu Lys Ser Glu Asp Asp Leu Leu Asn Phe Pro Ser Val
                85                  90                  95

Glu His Val Thr Ser Val Val Leu Lys Arg Met Ile Cys Asn Ala Leu
            100                 105                 110

Ile Asp Arg Pro Asn Thr Leu Phe Val Phe Asp Asp Val Val Gln Glu
        115                 120                 125

Glu Thr Ile Arg Trp Ala Gln Glu Leu Arg Leu Arg Cys Leu Val Thr
```

```
                130                 135                 140
Thr Arg Asp Val Glu Ile Ser Asn Ala Ala Ser Gln Thr Cys Glu Phe
145                 150                 155                 160

Ile Glu Val Thr Ser Leu Glu Ile Asp Glu Cys Tyr Asp Phe Leu Glu
                165                 170                 175

Ala Tyr Gly Met Pro Met Pro Val Gly Glu Lys Glu Glu Asp Val Leu
                180                 185                 190

Asn Lys Thr Ile Glu Leu Ser Ser Gly Asn Pro Ala Thr Leu Met Met
                195                 200                 205

Phe Phe Lys Ser Cys Glu Pro Lys Thr Phe Glu Lys Met Ala Gln Leu
210                 215                 220

Asn Asn Lys Leu Glu Ser Arg Gly Leu Val Gly Val Glu Cys Ile Thr
225                 230                 235                 240

Pro Tyr Ser Tyr Lys Ser Leu Ala Met Ala Leu Gln Arg Cys Val Glu
                245                 250                 255

Val Leu Ser Asp Glu Asp Arg Ser Ala Leu Ala Phe Ala Val Val Met
                260                 265                 270

Pro Pro Gly Val Asp Ile Pro Val Lys Leu Trp Ser Cys Val Ile Pro
                275                 280                 285

Val Asp Ile Cys Ser Asn Glu Glu Glu Gln Leu Asp Asp Glu Val Ala
                290                 295                 300

Asp Arg Leu Lys Arg Leu Ser Lys Arg Gly Ala
305                 310                 315

<210> SEQ ID NO 33
<211> LENGTH: 4486
<212> TYPE: DNA
<213> ORGANISM: Homo sapiens

<400> SEQUENCE: 33
gtagacagat ccaggctcac cagtcctgtg ccactgggct tttggcgttc tgcacaaggc    60
ctacccgcag atgccatgcc tgctccccca gcctaatggg ctttgatggg ggaagagggt   120
ggttcagcct ctcacgatga ggaggaaaga gcaagtgtcc tcctcggaca ttctccgggt   180
tgtgaaatgt gctcgcagga ggcttttcag gcacagagga gccagctggt cgagctgctg   240
gtctcagggt ccctggaagg cttcgagagt gtcctggact ggctgctgtc ctgggaggtc   300
ctctcctggg aggactacga gggcttccac ctcctgggcc agcctctctc ccacttggcc   360
aggcgccttc tggacaccgt ctggaataag ggtacttggg cctgtcagaa gctcatcgcg   420
gctgcccaag aagcccaggc cgacagccag tcccccaagc tgcatggctg ctgggacccc   480
cactcgctcc acccagcccg agacctgcag agtcaccggc cagccattgt caggaggctc   540
cacagccatg tggagaacat gctggacctg catgggagc ggggtttcgt cagccagtat   600
gaatgtgatg aaatcaggtt gccgatcttc acaccgtccc agagggcaag aaggctgctt   660
gatcttgcca cggtgaaagc gaatggattg ctgccttcc ttctacaaca tgttcaggaa   720
ttaccagtcc cattggccct gcctttggaa gctgccacat gcaagaagta tatggccaag   780
ctgaggacca cggtgtctgc tcagtctcgc ttcctcagta cctatgatgg agcagagacg   840
ctctgcctgg aggacatata cagagaat gtcctggagg tctgggcaga tgtgggcatg   900
gctggacccc cgcagaagag cccagccacc ctgggcctgg aggagctctt cagcacccct   960
ggccacctca atgacgatgc ggacactgtg ctggtggtgg gtgaggcggg cagtggcaag  1020
agcacgctcc tgcagcggct gcacttgctg tgggctgcag ggcaagactt ccaggaattt  1080
```

```
ctctttgtct tcccattcag ctgccggcag ctgcagtgca tggccaaacc actctctgtg    1140
cggactctac tctttgagca ctgctgttgg cctgatgttg gtcaagaaga catcttccag    1200
ttactccttg accaccctga ccgtgtcctg ttaacctttg atggctttga cgagttcaag    1260
ttcaggttca cggatcgtga acgccactgc tccccgaccg accccacctc tgtccagacc    1320
ctgctcttca accttctgca gggcaacctg ctgaagaatg cccgcaaggt ggtgaccagc    1380
cgtccggccg ctgtgtcggc gttcctcagg aagtacatcc gcaccgagtt caacctcaag    1440
ggcttctctg aacagggcat cgagctgtac ctgaggaagc gccatcatga gcccggggtg    1500
gcggaccgcc tcatccgcct gctccaagag acctcagccc tgcacggttt gtgccacctg    1560
cctgtcttct catggatggt gtccaaatgc caccaggaac tgttgctgca gggggggggg    1620
tccccaaaga ccactacaga tatgtacctg ctgattctgc agcatttctc gctgcatgcc    1680
acccccccag actcagcttc caaggtctgg gacccagtc ttcttcgggg ccgcctcccc    1740
accctcctgc acctgggcag actggctctg tggggcctgg gcatgtgctg ctacgtgttc    1800
tcagcccagc agctccaggc agcacaggtc agccctgatg acatttctct tggcttcctg    1860
gtgcgtgcca aggtgtcgt gccagggagt acggcgcccc tggaattcct tcacatcact    1920
ttccagtgct tctttgccgc gttctacctg gcactcagtg ctgatgtgcc accagctttg    1980
ctcagacacc tcttcaattg tggcaggcca ggcaactcac caatggccag gctcctgccc    2040
acgatgtgca tccaggcctc ggagggaaag acagcagcg tggcagcttt gctgcagaag    2100
gccgagccgc acaaccttca gatcacagca gccttcctgg cagggctgtt gtcccgggag    2160
cactggggcc tgctggctga gtgccagaca tctgagaagg ccctgctccg cgccaggcc    2220 tgtgcccgct ggtgtctggc ccgcagcctc cgcaagcact ccactccat cccgccagct    2280 gcaccgggtg aggccaagag cgtgcatgcc atgcccgggt tcatctggct catccggagc    2340
ctgtacgaga tgcaggagga gcggctggct cggaaggctg cacgtggcct gaatgttggg    2400
cacctcaagt tgacatttg cagtgtgggc cccactgagt gtgctgccct ggcctttgtg    2460
ctgcagcacc tccggcggcc cgtggccctg cagctggact acaactctgt gggtgacatt    2520
ggcgtggagc agctgctgcc ttgccttggt gtctgcaagg ctctgtattt gcgcgataac    2580
aatatctcag accgaggcat ctgcaagctc attgaatgtg ctcttcactg cgagcaattg    2640
cagaagttag ctctattcaa caacaaattg actgacggct gtgcacactc catggctaag    2700
ctccttgcat gcaggcagaa cttcttggca ttgaggctgg gaataacta catcactgcc    2760 gcgggagccc aagtgctggc cgagggggctc cgaggcaaca cctccttgca gttcctggga    2820
ttctggggca acagagtggg tgacgagggg gcccaggccc tggctgaagc cttgggtgat    2880
caccagagct tgaggtggct cagcctggtg gggaacaaca ttggcagtgt gggtgcccaa    2940
gccttggcac tgatgctggc aaagaacgtc atgctagaag aactctgcct ggaggagaac    3000
catctccagg atgaaggtgt atgttctctc gcagaaggac tgaagaaaaa ttcaagtttg    3060
aaaatcctga gttgtccaa taactgcatc acctacctag gggcagaagc cctcctgcag    3120
gccccttgaa aggaatgaca ccatcctgga agtctggctc cgagggaaca ctttctctct    3180
agaggaggtt gacaagctcg gctgcaggga caccagactc ttgctttgaa gtctccggga    3240
ggatgttcgt ctcagtttgt ttgtgagcag gctgtgagtt tgggcccag aggctgggtg    3300 acatgtgttg gcagcctctt caaaatgagc cctgtcctgc ctaaggctga acttgttttc    3360
tgggaacacc ataggtcacc tttattctgg cagaggaggg agcatcagtg ccctccagga    3420
tagacttttc ccaagcctac ttttgccatt gacttcttcc caagattcaa tcccaggatg    3480
```

-continued

| | |
|---|---|
| tacaaggaca gcccctcctc catagtatgg gactggcctc tgctgatcct cccaggcttc | 3540 |
| cgtgtgggtc agtggggccc atggatgtgc ttgttaactg agtgccttt ggtggagagg | 3600 |
| cccggcctct cacaaaagac cccttaccac tgctctgatg aagaggagta cacagaacac | 3660 |
| ataattcagg aagcagcttt ccccatgtct cgactcatcc atccaggcca ttccccgtct | 3720 |
| ctggttcctc ccctcctcct ggactcctgc acacgctcct tcctctgagg ctgaaattca | 3780 |
| gaatattagt gacctcagct ttgatatttc acttacagca cccccaaccc tggcacccag | 3840 |
| ggtgggaagg gctacacctt agcctgccct cctttccggt gtttaagaca ttttttggaag | 3900 |
| gggacacgtg acagccgttt gttccccaag acattctagg tttgcaagaa aaatatgacc | 3960 |
| acactccagc tgggatcaca tgtggacttt tatttccagt gaaatcagtt actcttcagt | 4020 |
| taagcctttg gaaacagctc gactttaaaa agctccaaat gcagctttaa aaaattaatc | 4080 |
| tgggccagaa tttcaaacgg cctcactagg cttctggttg atgcctgtga actgaactct | 4140 |
| gacaacagac ttctgaaata gacccacaag aggcagttcc atttcatttg tgccagaatg | 4200 |
| ctttaggatg tacagttatg gattgaaagt ttacaggaaa aaaaattagg ccgttccttc | 4260 |
| aaagcaaatg tcttcctgga ttattcaaaa tgatgtatgt tgaagccttt gtaaattgtc | 4320 |
| agatgctgtg caaatgttat tatttttaaac attatgatgt gtgaaaactg gttaatattt | 4380 |
| ataggtcact ttgttttact gtcttaagtt tatactctta tagacaacat ggccgtgaac | 4440 |
| tttatgctgt aaataatcag aggggaataa actgttgagt caaaac | 4486 |

<210> SEQ ID NO 34
<211> LENGTH: 1007
<212> TYPE: PRT
<213> ORGANISM: Homo sapiens

<400> SEQUENCE: 34

Met Gly Glu Glu Gly Gly Ser Ala Ser His Asp Glu Glu Arg Ala
1               5                   10                  15

Ser Val Leu Leu Gly His Ser Pro Gly Cys Glu Met Cys Ser Gln Glu
                20                  25                  30

Ala Phe Gln Ala Gln Arg Ser Gln Leu Val Glu Leu Leu Val Ser Gly
            35                  40                  45

Ser Leu Glu Gly Phe Glu Ser Val Leu Asp Trp Leu Leu Ser Trp Glu
        50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

```
Asn Gly Leu Ala Ala Phe Leu Leu Gln His Val Gln Glu Leu Pro Val
    195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Pro Pro Gln Lys Ser
            260                 265                 270

Pro Ala Thr Leu Gly Leu Glu Leu Phe Ser Thr Pro Gly His Leu
        275                 280                 285

Asn Asp Asp Ala Asp Thr Val Leu Val Val Gly Glu Ala Gly Ser Gly
    290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
        355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
        435                 440                 445

Glu Gln Gly Ile Glu Leu Tyr Leu Arg Lys Arg His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
        515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
545                 550                 555                 560

Cys Cys Tyr Val Phe Ser Ala Gln Gln Leu Gln Ala Ala Gln Val Ser
                565                 570                 575

Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
        595                 600                 605

Phe Phe Ala Ala Phe Tyr Leu Ala Leu Ser Ala Asp Val Pro Pro Ala
```

```
                610                 615                 620
Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                645                 650                 655

Ser Ser Val Ala Ala Leu Leu Gln Lys Ala Glu Pro His Asn Leu Gln
                660                 665                 670

Ile Thr Ala Ala Phe Leu Ala Gly Leu Leu Ser Arg Glu His Trp Gly
                675                 680                 685

Leu Leu Ala Glu Cys Gln Thr Ser Glu Lys Ala Leu Leu Arg Arg Gln
690                 695                 700

Ala Cys Ala Arg Trp Cys Leu Ala Arg Ser Leu Arg Lys His Phe His
705                 710                 715                 720

Ser Ile Pro Pro Ala Pro Gly Glu Ala Lys Ser Val His Ala Met
                725                 730                 735

Pro Gly Phe Ile Trp Leu Ile Arg Ser Leu Tyr Glu Met Gln Glu Glu
                740                 745                 750

Arg Leu Ala Arg Lys Ala Ala Arg Gly Leu Asn Val Gly His Leu Lys
                755                 760                 765

Leu Thr Phe Cys Ser Val Gly Pro Thr Glu Cys Ala Ala Leu Ala Phe
                770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
                820                 825                 830

Cys Lys Leu Ile Glu Cys Ala Leu His Cys Glu Gln Leu Gln Lys Leu
                835                 840                 845

Ala Leu Phe Asn Asn Lys Leu Thr Asp Gly Cys Ala His Ser Met Ala
850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
                900                 905                 910

Asp Glu Gly Ala Gln Ala Leu Ala Glu Ala Leu Gly Asp His Gln Ser
                915                 920                 925

Leu Arg Trp Leu Ser Leu Val Gly Asn Asn Ile Gly Ser Val Gly Ala
                930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
                980                 985                 990

Asn Cys Ile Thr Tyr Leu Gly Ala  Glu Ala Leu Leu Gln  Ala Pro
                995                 1000                1005

<210> SEQ ID NO 35
<211> LENGTH: 360
<212> TYPE: DNA
<213> ORGANISM: Homo sapiens
```

<400> SEQUENCE: 35

```
cagacatgag caggatgtgt ctaagggaca ggtgggcttc agtagactgg ctaactcctg      60
cagtctcttt aactggacag tttcaagagg aaaaccaaga atccttgaag ctcaccattg     120
tatcttcttt tccaggttgt ccaataactg catcacctac ctaggggcag aagcccctcct   180
gcaggccctt gaaaggaatg acaccatcct ggaagtctgg taaggcccct gggcaggcct    240
gttttagctc tccgaacctc agttttcta tctgtaaaat ggggtgacgg gagagaggaa     300
tggcagaatt ttgaggatcc cttctgattc tgacattcag tgagaatgat tctgcatgtg    360
```

<210> SEQ ID NO 36
<211> LENGTH: 361
<212> TYPE: DNA
<213> ORGANISM: Homo sapiens

<400> SEQUENCE: 36

```
cagacatgag caggatgtgt ctaagggaca ggtgggcttc agtagactgg ctaactcctg      60
cagtctcttt aactggacag tttcaagagg aaaaccaaga atccttgaag ctcaccattg     120
tatcttcttt tccaggttgt ccaataactg catcacctac ctaggggcag aagcccctcct   180
gcaggcccct tgaaaggaat gacaccatcc tggaagtctg gtaaggcccc tgggcaggcc    240
tgttttagct ctccgaacct cagttttct atctgtaaaa tggggtgacg ggagagagga     300
atggcagaat tttgaggatc ccttctgatt ctgacattca gtgagaatga ttctgcatgt    360
g                                                                    361
```

<210> SEQ ID NO 37
<211> LENGTH: 27
<212> TYPE: DNA
<213> ORGANISM: Artificial Sequence
<220> FEATURE:
<223> OTHER INFORMATION: Synthetic

<400> SEQUENCE: 37

```
atgtgctcgc aggaggcttt tcaggca                                         27
```

<210> SEQ ID NO 38
<211> LENGTH: 26
<212> TYPE: DNA
<213> ORGANISM: Artificial Sequence
<220> FEATURE:
<223> OTHER INFORMATION: Synthetic

<400> SEQUENCE: 38

```
cgcctcaccc accaccagca cagtgt                                          26
```

<210> SEQ ID NO 39
<211> LENGTH: 28
<212> TYPE: DNA
<213> ORGANISM: Artificial Sequence
<220> FEATURE:
<223> OTHER INFORMATION: Synthetic

<400> SEQUENCE: 39

```
catggctgga cccccgcaga agagccca                                        28
```

<210> SEQ ID NO 40
<211> LENGTH: 28
<212> TYPE: DNA
<213> ORGANISM: Artificial Sequence
<220> FEATURE:

```
<223> OTHER INFORMATION: Synthetic

<400> SEQUENCE: 40
catgcccggg ttcatctggc tcatccgg                                      28

<210> SEQ ID NO 41
<211> LENGTH: 27
<212> TYPE: DNA
<213> ORGANISM: Artificial Sequence
<220> FEATURE:
<223> OTHER INFORMATION: Synthetic

<400> SEQUENCE: 41
gccatgcccg ggttcatctg gctcatc                                       27

<210> SEQ ID NO 42
<211> LENGTH: 28
<212> TYPE: DNA
<213> ORGANISM: Artificial Sequence
<220> FEATURE:
<223> OTHER INFORMATION: Synthetic

<400> SEQUENCE: 42
tgagtcgaga catggggaaa gctgcttc                                      28

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
agcagctcga ccagctggct cctctgt                                       27

<210> SEQ ID NO 44
<211> LENGTH: 27
<212> TYPE: DNA
<213> ORGANISM: Artificial Sequence
<220> FEATURE:
<223> OTHER INFORMATION: Synthetic

<400> SEQUENCE: 44
gacaggccca agtaccctta ttccaga                                       27

<210> SEQ ID NO 45
<211> LENGTH: 27
<212> TYPE: DNA
<213> ORGANISM: Artificial Sequence
<220> FEATURE:
<223> OTHER INFORMATION: Synthetic

<400> SEQUENCE: 45
atgtgctcgc aggaggcttt tcaggca                                       27

<210> SEQ ID NO 46
<211> LENGTH: 26
<212> TYPE: DNA
<213> ORGANISM: Artificial Sequence
<220> FEATURE:
<223> OTHER INFORMATION: Synthetic

<400> SEQUENCE: 46
cgcctcaccc accaccagca cagtgt                                        26
```

```
<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atgtgctcgc aggaggcttt tcaggca                                        27

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48
cgcctcaccc accaccagca cagtgt                                         26

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
gagtcaacgg atttggtcgt at                                             22

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
agtcttctgg gtggcagtga t                                              21

<210> SEQ ID NO 51
<211> LENGTH: 27
<212> TYPE: PRT
<213> ORGANISM: Homo sapiens

<400> SEQUENCE: 51

Leu Ser Asn Asn Cys Ile Thr Tyr Leu Gly Ala Glu Ala Leu Leu Gln
1               5                   10                  15

Ala Leu Glu Arg Asn Asp Thr Ile Leu Glu Val
            20                  25

<210> SEQ ID NO 52
<211> LENGTH: 18
<212> TYPE: PRT
<213> ORGANISM: Homo sapiens

<400> SEQUENCE: 52

Leu Ser Asn Asn Cys Ile Thr Tyr Leu Gly Ala Glu Ala Leu Leu Gln
1               5                   10                  15

Ala Pro

<210> SEQ ID NO 53
<211> LENGTH: 21
<212> TYPE: DNA
<213> ORGANISM: Artificial
```

```
<220> FEATURE:
<223> OTHER INFORMATION: synthetic

<400> SEQUENCE: 53
cggatgtgga tacctataag g                                              21

<210> SEQ ID NO 54
<211> LENGTH: 3124
<212> TYPE: DNA
<213> ORGANISM: Homo sapiens

<400> SEQUENCE: 54
atgggggaag agggtggttc agcctctcac gatgaggagg aaagagcaag tgtcctcctc      60
ggacattctc cggggttgtga aatgtgctcg caggaggctt ttcaggcaca gaggagccag    120
ctggtcgagc tgctggtctc agggtccctg gaaggcttcg agagtgtcct ggactggctg    180
ctgtcctggg aggtcctctc ctgggaggac tacgagggct ccacctcct gggccagcct     240 ctctcccact tggccaggcg ccttctggac accgtctgga ataagggtac ttgggcctgt    300
cagaagctca tcgcggctgc ccaagaagcc caggccgaca gccagtcccc caagctgcat    360
ggctgctggg accccactc gctccaccca gcccgagacc tgcagagtca ccggccagcc    420
attgtcagga ggctccacag ccatgtggag aacatgctgg acctggcatg ggagcggggt    480
ttcgtcagcc agtatgaatg tgatgaaatc aggttgccga tcttcacacc gtcccagagg    540
gcaagaaggc tgcttgatct tgccacggtg aaagcgaatg gattggctgc cttccttcta    600
caacatgttc aggaattacc agtcccattg gccctgcctt tggaagctgc acatgcaag    660 aagtatatgg ccaagctgag gaccacggtg tctgctcagt ctcgcttcct cagtacctat    720 gatgagcag agacgctctg cctggaggac atatacacag agaatgtcct ggaggtctgg    780
gcagatgtgg gcatggctgg atccccgcag aagagcccag ccaccctggg cctggaggag    840
ctcttcagca cccctggcca cctcaatgac gatgcggaca ctgtgctggt ggtgggtgag    900
gcgggcagtg gcaagagcac gctcctgcag cggctgcact gctgtgggc tgcagggcaa    960 gacttccagg aatttctctt tgtcttccca ttcagctgcc ggcagctgca gtgcatggcc   1020
aaaccactct ctgtgcggac tctactcttt gagcactgct gttggcctga tgttggtcaa   1080
gaagacatct tccagttact ccttgaccac cctgaccgtg tcctgttaac ctttgatggc   1140
tttgacgagt tcaagttcag gttcacggat cgtgaacgcc actgctcccc gaccgacccc   1200
acctctgtcc agaccctgct cttcaaccct ctgcagggca acctgctgaa gaatgcccgc   1260
aaggtggtga ccagccgtcc ggccgctgtg tcggcgttcc tcaggaagta catccgcacc   1320
gagttcaacc tcaagggctt ctctgaacag ggcatcgagc tgtacctgag gaagcgccat   1380
catgagcccg ggtggcgga ccgcctcatc cgcctgctcc aagagacctc agccctgcac   1440
ggtttgtgcc acctgcctgt cttctcatgg atggtgtcca atgccacca ggaactgttg   1500 ctgcaggagg gggggtcccc aaagaccact acagatatgt acctgctgat tctgcagcat   1560
tttctgctgc atgccacccc cagactca gcttcccaag gtctgggacc cagtcttctt     1620
cggggccgcc tccccaccct cctgcacctg gcagactgg ctctgtgggg cctgggcatg    1680
tgctgctacg tgttctcagc ccagcagctc caggcagcac aggtcagccc tgatgacatt   1740
tctcttggct tcctggtgcg tgccaaaggt gtcgtgccag ggagtacggc gcccctggaa   1800
ttccttcaca tcactttcca gtgcttcttt gccgcgttct acctggcact cagtgctgat   1860
gtgccaccag ctttgctcag acacctcttc aattgtggca ggccaggcaa ctcaccaatg   1920
```

-continued

```
gccaggctcc tgcccacgat gtgcatccag gcctcggagg gaaaggacag cagcgtggca      1980
gctttgctgc agaaggccga gccgcacaac cttcagatca cagcagcctt cctggcaggg      2040
ctgttgtccc gggagcactg gggcctgctg gctgagtgcc agacatctga gaaggccctg      2100
ctccggcgcc aggcctgtgc cgctggtgt ctggcccgca gcctccgcaa gcacttccac       2160
tccatcccgc cagctgcacc gggtgaggcc aagagcgtgc atgccatgcc cgggttcatc      2220
tggctcatcc ggagcctgta cgagatgcag gaggagcggc tggctcggaa ggctgcacgt      2280
ggcctgaatg ttgggcacct caagttgaca ttttgcagtg tgggcccac tgagtgtgct       2340
gccctggcct ttgtgctgca gcacctccgg cggcccgtgg ccctgcagct ggactacaac      2400
tctgtgggtg acattggcgt ggagcagctg ctgccttgcc ttggtgtctg caaggctctg      2460
tatttgcgcg ataacaatat ctcagaccga ggcatctgca agctcattga atgtgctctt      2520
cactgcgagc aattgcagaa gttagctcta ttcaacaaca aattgactga cggctgtgca      2580
cactccatgg ctaagctcct tgcatgcagg cagaacttct tggcattgag ctggggaat       2640
aactacatca ctgccgcggg agcccaagtg ctggccgagg ggctccgagg caacacctcc      2700
ttgcagttcc tgggattctg gggcaacaga gtgggtgacg agggggccca ggccctggct      2760
gaagccttgg gtgatcacca gagcttgagg tggctcagcc tggtggggaa caacattggc      2820
agtgtgggtg cccaagcctt ggcactgatg ctggcaaaga acgtcatgct agaagaactc      2880
tgcctggagg agaaccatct ccaggatgaa ggtgtatgtt ctctcgcaga aggactgaag      2940
aaaaattcaa gtttgaaaat cctgaagttg tccaataact gcatcaccta cctaggggca      3000
gaagccctcc tgcaggcccc ttgaaaggaa tgacaccatc ctggaagtct ggctccgagg      3060
gaacactttc tctctagagg aggttgacaa gctcggctgc agggacacca gactcttgct      3120
ttga                                                                  3124
```

<210> SEQ ID NO 55
<211> LENGTH: 1007
<212> TYPE: PRT
<213> ORGANISM: Homo sapiens

<400> SEQUENCE: 55

```
Met Gly Glu Glu Gly Gly Ser Ala Ser His Asp Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160
```

-continued

```
Phe Val Ser Gln Tyr Glu Cys Asp Glu Ile Arg Leu Pro Ile Phe Thr
                165                 170                 175

Pro Ser Gln Arg Ala Arg Leu Leu Asp Leu Ala Thr Val Lys Ala
        180                 185                 190

Asn Gly Leu Ala Ala Phe Leu Leu Gln His Val Gln Glu Leu Pro Val
            195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Ser Pro Gln Lys Ser
            260                 265                 270

Pro Ala Thr Leu Gly Leu Glu Glu Leu Phe Ser Thr Pro Gly His Leu
        275                 280                 285

Asn Asp Asp Ala Asp Thr Val Leu Val Val Gly Glu Ala Gly Ser Gly
    290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
        355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
        435                 440                 445

Glu Gln Gly Ile Glu Leu Tyr Leu Arg Lys Arg His His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
        515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
545                 550                 555                 560

Cys Cys Tyr Val Phe Ser Ala Gln Gln Leu Gln Ala Ala Gln Val Ser
                565                 570                 575
```

```
Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
            595                 600                 605

Phe Phe Ala Ala Phe Tyr Leu Ala Leu Ser Ala Asp Val Pro Pro Ala
610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
            645                 650                 655

Ser Ser Val Ala Ala Leu Leu Gln Lys Ala Glu Pro His Asn Leu Gln
            660                 665                 670

Ile Thr Ala Ala Phe Leu Ala Gly Leu Leu Ser Arg Glu His Trp Gly
            675                 680                 685

Leu Leu Ala Glu Cys Gln Thr Ser Glu Lys Ala Leu Leu Arg Arg Gln
690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
            725                 730                 735

Pro Gly Phe Ile Trp Leu Ile Arg Ser Leu Tyr Glu Met Gln Glu Glu
            740                 745                 750

Arg Leu Ala Arg Lys Ala Ala Arg Gly Leu Asn Val Gly His Leu Lys
            755                 760                 765

Leu Thr Phe Cys Ser Val Gly Pro Thr Glu Cys Ala Ala Leu Ala Phe
            770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
                820                 825                 830

Cys Lys Leu Ile Glu Cys Ala Leu His Cys Glu Gln Leu Gln Lys Leu
            835                 840                 845

Ala Leu Phe Asn Asn Lys Leu Thr Asp Gly Cys Ala His Ser Met Ala
            850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
            915                 920                 925

Leu Arg Trp Leu Ser Leu Val Gly Asn Asn Ile Gly Ser Val Gly Ala
            930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
            980                 985                 990

Asn Cys Ile Thr Tyr Leu Gly Ala  Glu Ala Leu Leu Gln  Ala Pro
```

<210> SEQ ID NO 56
<211> LENGTH: 3123
<212> TYPE: DNA
<213> ORGANISM: Homo sapiens

<400> SEQUENCE: 56

| | | | | | |
|---|---|---|---|---|---|
| atgggggaag | agggtggttc | agcctctcac | gatgaggagg | aaagagcaag | tgtcctcctc | 60 |
| ggacattctc | cgggttgtga | aatgtgctcg | caggaggctt | ttcaggcaca | gaggagccag | 120 |
| ctggtcgagc | tgctggtctc | agggtccctg | aaggcttcg | agagtgtcct | ggactggctg | 180 |
| ctgtcctggg | aggtcctctc | ctgggaggac | tacgagggct | ccacctcct | gggccagcct | 240 |
| ctctcccact | tggccaggcg | ccttctggac | accgtctgga | ataagggtac | ttgggcctgt | 300 |
| cagaagctca | tcgcggctgc | ccaagaagcc | caggccgaca | gccagtcccc | caagctgcat | 360 |
| ggctgctggg | accccactc | gctccaccca | gcccgagacc | tgcagagtca | ccggccagcc | 420 |
| attgtcagga | ggctccacag | ccatgtggag | aacatgctgg | acctggcatg | ggagcggggt | 480 |
| ttcgtcagcc | agtatgaatg | tgatgaaatc | aggttgccga | tcttcacacc | gtcccagagg | 540 |
| gcaagaaggc | tgcttgatct | tgccacggtg | aaagcgaatg | gattggctgc | cttccttcta | 600 |
| caacatgttc | aggaattacc | agtcccattg | ccctgccttt | ggaagctgc | acatgcaag | 660 |
| aagtatatgg | ccaagctgag | gaccacggtg | tctgctcagt | ctcgcttcct | cagtacctat | 720 |
| gatggagcag | agacgctctg | cctggaggac | atatacacag | agaatgtcct | ggaggtctgg | 780 |
| gcagatgtgg | gcatggctgg | atccccgcag | aagagcccag | ccaccctggg | cctggaggag | 840 |
| ctcttcagca | cccctggcca | cctcaatgac | gatgcggaca | ctgtgctggt | ggtgggtgag | 900 |
| gcgggcagtg | gcaagagcac | gctcctgcag | cggctgcact | gctgtgggc | tgcagggcaa | 960 |
| gacttccagg | aatttctctt | tgtcttccca | ttcagctgcc | ggcagctgca | gtgcatggcc | 1020 |
| aaaccactct | ctgtgcggac | tctactcttt | gagcactgct | gttggcctga | tgttggtcaa | 1080 |
| gaagacatct | tccagttact | ccttgaccac | cctgaccgtg | tcctgttaac | ctttgatggc | 1140 |
| tttgacgagt | tcaagttcag | gttcacggat | cgtgaacgcc | actgctcccc | gaccgacccc | 1200 |
| acctctgtcc | agaccctgct | cttcaacctt | ctgcagggca | acctgctgaa | gaatgcccgc | 1260 |
| aaggtggtga | ccagccgtcc | ggccgctgtg | tcggcgttcc | tcaggaagta | catccgcacc | 1320 |
| gagttcaacc | tcaagggctt | ctctgaacag | ggcatcgagc | tgtacctgag | gaagcgccat | 1380 |
| catgagcccg | ggtggcgga | ccgcctcatc | cgcctgctcc | aagagacctc | agccctgcac | 1440 |
| ggtttgtgcc | acctgcctgt | cttctcatgg | atggtgtcca | aatgccacca | ggaactgttg | 1500 |
| ctgcaggagg | gggggtcccc | aaagaccact | acagatatgt | acctgctgat | ctgcagcat | 1560 |
| tttctgctgc | atgccacccc | cccagactca | gcttcccaag | gtctgggacc | cagtcttctt | 1620 |
| cggggccgcc | tccccaccct | cctgcacctg | ggcagactgg | ctctgtgggg | cctgggcatg | 1680 |
| tgctgctacg | tgttctcagc | ccagcagctc | caggcagcac | aggtcagccc | tgatgacatt | 1740 |
| tctcttggct | tcctggtgcg | tgccaaaggt | gtcgtgccag | ggagtacggc | gcccctggaa | 1800 |
| ttccttcaca | tcactttcca | gtgcttcttt | gccgcgttct | acctggcact | cagtgctgat | 1860 |
| gtgccaccag | ctttgctcag | acacctcttc | aattgtggca | ggcaggcaa | ctcaccaatg | 1920 |
| gccaggctcc | tgcccacgat | gtgcatccag | gcctcggagg | gaaaggacag | cagcgtggca | 1980 |
| gctttgctgc | agaaggccga | gccgcacaac | cttcagatca | cagcagcctt | cctggcaggg | 2040 |
| ctgttgtccc | gggagcactg | gggcctgctg | gctgagtgcc | agacatctga | gaaggccctg | 2100 |

-continued

```
ctccggcgcc aggcctgtgc ccgctggtgt ctggcccgca gcctccgcaa gcacttccac    2160
tccatcccgc cagctgcacc gggtgaggcc aagagcgtgc atgccatgcc cgggttcatc    2220
tggctcatcc ggagcctgta cgagatgcag gaggagcggc tggctcggaa ggctgcacgt    2280
ggcctgaatg ttgggcacct caagttgaca ttttgcagtg tgggcccac tgagtgtgct     2340 gccctggcct ttgtgctgca gcacctccgg cggcccgtgg ccctgcagct ggactacaac    2400
tctgtgggtg acattggcgt ggagcagctg ctgccttgcc ttggtgtctg caaggctctg    2460
tatttgcgcg ataacaatat ctcagaccga ggcatctgca agctcattga atgtgctctt    2520
cactgcgagc aattgcagaa gttagctcta ttcaacaaca aattgactga cggctgtgca    2580
cactccatgg ctaagctcct tgcatgcagg cagaacttct tggcattgag ctggggaat    2640 aactacatca ctgccgcggg agcccaagtg ctggccgagg ggctccgagg caacacctcc    2700
ttgcagttcc tgggattctg gggcaacaga gtgggtgacg agggggccca ggccctggct    2760
gaagccttgg gtgatcacca gagcttgagg tggctcagcc tggtggggaa caacattggc    2820
agtgtgggtg cccaagcctt ggcactgatg ctggcaaaga acgtcatgct agaagaactc    2880
tgcctggagg agaaccatct ccaggatgaa ggtgtatgtt ctctcgcaga aggactgaag    2940
aaaaattcaa gtttgaaaat cctgaagttg tccaataact gcatcaccta cctaggggca    3000
gaagccctcc tgcaggccct tgaaaggaat gacaccatcc tggaagtctg gctccgaggg    3060
aacactttct ctctagagga ggttgacaag ctcggctgca gggacaccag actcttgctt    3120
tga                                                                 3123
```

<210> SEQ ID NO 57
<211> LENGTH: 1040
<212> TYPE: PRT
<213> ORGANISM: Homo sapiens

<400> SEQUENCE: 57

```
Met Gly Glu Glu Gly Gly Ser Ala Ser His Asp Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ile Val Arg Arg
    130                 135                 140

Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
```

-continued

```
                180                 185                 190
Asn Gly Leu Ala Ala Phe Leu Leu Gln His Val Gln Glu Leu Pro Val
            195                 200                 205
Pro Leu Ala Leu Pro Leu Glu Ala Ala Thr Cys Lys Lys Tyr Met Ala
210                 215                 220
Lys Leu Arg Thr Thr Val Ser Ala Gln Ser Arg Phe Leu Ser Thr Tyr
225                 230                 235                 240
Asp Gly Ala Glu Thr Leu Cys Leu Glu Asp Ile Tyr Thr Glu Asn Val
                245                 250                 255
Leu Glu Val Trp Ala Asp Val Gly Met Ala Gly Ser Pro Gln Lys Ser
            260                 265                 270
Pro Ala Thr Leu Gly Leu Glu Glu Leu Phe Ser Thr Pro Gly His Leu
        275                 280                 285
Asn Asp Asp Ala Asp Thr Val Leu Val Gly Glu Ala Gly Ser Gly
290                 295                 300
Lys Ser Thr Leu Leu Gln Arg Leu His Leu Leu Trp Ala Ala Gly Gln
305                 310                 315                 320
Asp Phe Gln Glu Phe Leu Phe Val Phe Pro Phe Ser Cys Arg Gln Leu
                325                 330                 335
Gln Cys Met Ala Lys Pro Leu Ser Val Arg Thr Leu Leu Phe Glu His
            340                 345                 350
Cys Cys Trp Pro Asp Val Gly Gln Glu Asp Ile Phe Gln Leu Leu Leu
        355                 360                 365
Asp His Pro Asp Arg Val Leu Leu Thr Phe Asp Gly Phe Asp Glu Phe
    370                 375                 380
Lys Phe Arg Phe Thr Asp Arg Glu Arg His Cys Ser Pro Thr Asp Pro
385                 390                 395                 400
Thr Ser Val Gln Thr Leu Leu Phe Asn Leu Leu Gln Gly Asn Leu Leu
                405                 410                 415
Lys Asn Ala Arg Lys Val Val Thr Ser Arg Pro Ala Ala Val Ser Ala
            420                 425                 430
Phe Leu Arg Lys Tyr Ile Arg Thr Glu Phe Asn Leu Lys Gly Phe Ser
        435                 440                 445
Glu Gln Gly Ile Glu Leu Tyr Leu Arg Lys Arg His Glu Pro Gly
    450                 455                 460
Val Ala Asp Arg Leu Ile Arg Leu Leu Gln Glu Thr Ser Ala Leu His
465                 470                 475                 480
Gly Leu Cys His Leu Pro Val Phe Ser Trp Met Val Ser Lys Cys His
                485                 490                 495
Gln Glu Leu Leu Leu Gln Glu Gly Gly Ser Pro Lys Thr Thr Thr Asp
            500                 505                 510
Met Tyr Leu Leu Ile Leu Gln His Phe Leu Leu His Ala Thr Pro Pro
        515                 520                 525
Asp Ser Ala Ser Gln Gly Leu Gly Pro Ser Leu Leu Arg Gly Arg Leu
    530                 535                 540
Pro Thr Leu Leu His Leu Gly Arg Leu Ala Leu Trp Gly Leu Gly Met
545                 550                 555                 560
Cys Cys Tyr Val Phe Ser Ala Gln Gln Leu Gln Ala Ala Gln Val Ser
                565                 570                 575
Pro Asp Asp Ile Ser Leu Gly Phe Leu Val Arg Ala Lys Gly Val Val
            580                 585                 590
Pro Gly Ser Thr Ala Pro Leu Glu Phe Leu His Ile Thr Phe Gln Cys
        595                 600                 605
```

```
Phe Phe Ala Ala Phe Tyr Leu Ala Leu Ser Ala Asp Val Pro Pro Ala
    610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                645                 650                 655

Ser Ser Val Ala Ala Leu Leu Gln Lys Ala Glu Pro His Asn Leu Gln
            660                 665                 670

Ile Thr Ala Ala Phe Leu Ala Gly Leu Leu Ser Arg Glu His Trp Gly
        675                 680                 685

Leu Leu Ala Glu Cys Gln Thr Ser Glu Lys Ala Leu Leu Arg Arg Gln
690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
                725                 730                 735

Pro Gly Phe Ile Trp Leu Ile Arg Ser Leu Tyr Glu Met Gln Glu Glu
            740                 745                 750

Arg Leu Ala Arg Lys Ala Ala Arg Gly Leu Asn Val Gly His Leu Lys
        755                 760                 765

Leu Thr Phe Cys Ser Val Gly Pro Thr Glu Cys Ala Ala Leu Ala Phe
770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
            820                 825                 830

Cys Lys Leu Ile Glu Cys Ala Leu His Cys Glu Gln Leu Gln Lys Leu
        835                 840                 845

Ala Leu Phe Asn Asn Lys Leu Thr Asp Gly Cys Ala His Ser Met Ala
850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
        915                 920                 925

Leu Arg Trp Leu Ser Leu Val Gly Asn Asn Ile Gly Ser Val Gly Ala
930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
            980                 985                 990

Asn Cys Ile Thr Tyr Leu Gly Ala Glu Ala Leu Leu Gln Ala Leu Glu
        995                 1000                1005

Arg Asn Asp Thr Ile Leu Glu Val Trp Leu Arg Gly Asn Thr Phe
    1010                1015                1020
```

```
Ser Leu Glu Glu Val Asp Lys  Leu Gly Cys Arg Asp  Thr Arg Leu
    1025            1030              1035

Leu Leu
    1040

<210> SEQ ID NO 58
<211> LENGTH: 3123
<212> TYPE: DNA
<213> ORGANISM: Homo sapiens

<400> SEQUENCE: 58
atgggggaag agggtggttc agcctctcac gatgaggagg aaagagcaag tgtcctcctc      60
ggacattctc cggggttgtga aatgtgctcg caggaggctt ttcaggcaca gaggagccag    120
ctggtcgagc tgctggtctc agggtccctg gaaggcttcg agagtgtcct ggactggctg    180
ctgtcctggg aggtcctctc ctgggaggac tacgagggct ccacctcct gggccagcct     240 ctctcccact tggccaggcg ccttctggac accgtctgga ataagggtac ttgggcctgt    300
cagaagctca tcgcggctgc ccaagaagcc caggccgaca gccagtcccc caagctgcat    360
ggctgctggg acccccactc gctccaccca gcccgagacc tgcagagtca ccggccagcc    420
attgtcagga ggctccacag ccatgtggag aacatgctgg acctggcatg ggagcggggt    480
ttcgtcagcc agtatgaatg tgatgaaatc aggttgccga tcttcacacc gtcccagagg    540
gcaagaaggc tgcttgatct tgccacggtg aaagcgaatg gattggctgc cttccttcta    600
caacatgttc aggaattacc agtcccattg gccctgcctt tggaagctgc acatgcaag     660 aagtatatgg ccaagctgag gaccacggtg tctgctcagt ctcgcttcct cagtacctat    720
gatggagcag agacgctctg cctggaggac atatacacag agaatgtcct ggaggtctgg    780
gcagatgtgg gcatggctgg atccccgcag aagagcccag ccaccctggg cctggaggag    840
ctcttcagca cccctggcca cctcaatgac gatgcggaca ctgtgctggt ggtgggtgag    900
gcgggcagtg gcaagagcac gctcctgcag cggctgcact gctgtgggc tgcagggcaa    960 gacttccagg aatttctctt tgtcttccca ttcagctgcc ggcagctgca gtgcatggcc   1020
aaaccactct ctgtgcggac tctactcttt gagcactgct gttggcctga tgttggtcaa   1080
gaagacatct tccagttact ccttgaccac cctgaccgtg tcctgttaac ctttgatggc   1140
tttgacgagt tcaagttcag gttcacggat cgtgaacgcc actgctcccc gaccgaccc    1200 acctctgtcc agaccctgct cttcaaccct ctgcagggca acctgctgaa gaatgcccgc   1260
aaggtggtga ccagccgtcc ggccgctgtg tcggcgttcc tcaggaagta catccgcacc   1320
gagttcaacc tcaagggctt ctctgaacag gcatcgagc tgtacctgag gaagcgccat    1380
catgagcccg gggtggcgga ccgcctcatc cgcctgctcc aagagacctc agccctgcac   1440
ggtttgtgcc acctgcctgt cttctcatgg atggtgtcca atgccacca ggaactgttg   1500 ctgcaggagg gggggtcccc aaagaccact acagatatgt acctgctgat tctgcagcat   1560
tttctgctgc atgccacccc ccagactca gcttcccaag gtctgggacc cagtcttctt    1620
cggggccgcc tccccaccct cctgcacctg ggcagactgg ctctgtgggg cctgggcatg   1680
tgctgctacg tgttctcagc ccagcagctc caggcagcac aggtcagccc tgatgacatt   1740
tctcttggct tcctggtgcg tgccaaaggt gtcgtgccag ggagtacggc gcccctggaa   1800
ttccttcaca tcactttcca gtgcttcttt gccgcgttct acctggcact cagtgctgat   1860
gtgccaccag ctttgctcag acacctcttc aattgtggca ggccaggcaa ctcaccaatg   1920
gccaggctcc tgcccacgat gtgcatccag gcctcggagg gaaaggacag cagcgtggca   1980
```

```
gctttgctgc agaaggccga gccgcacaac cttcagatca cagcagcctt cctggcaggg    2040
ctgttgtccc gggagcactg gggcctgctg gctgagtgcc agacatctga gaaggccctg    2100
ctctggcgcc aggcctgtgc ccgctggtgt ctggcccgca gcctccgcaa gcacttccac    2160
tccatcccgc cagctgcacc gggtgaggcc aagagcgtgc atgccatgcc cgggttcatc    2220
tggctcatcc ggagcctgta cgagatgcag gaggagcggc tggctcggaa ggctgcacgt    2280
ggcctgaatg ttgggcacct caagttgaca ttttgcagtg tgggcccccac tgagtgtgct    2340 gccctggcct ttgtgctgca gcacctccgg cggcccgtgg ccctgcagct ggactacaac    2400
tctgtgggtg acattggcgt ggagcagctg ctgccttgcc ttggtgtctg caaggctctg    2460
tatttgcgcg ataacaatat ctcagaccga ggcatctgca agctcattga atgtgctctt    2520
cactgcgagc aattgcagaa gttagctcta ttcaacaaca aattgactga cggctgtgca    2580
cactccatgg ctaagctcct tgcatgcagg cagaacttct tggcattgag gctggggaat    2640
aactacatca ctgccgcggg agcccaagtg ctggccgagg ggctccgagg caacacctcc    2700
ttgcagttcc tgggattctg gggcaacaga gtgggtgacg agggggccca ggccctggct    2760
gaagccttgg gtgatcacca gagcttgagg tggctcagcc tggtggggaa caacattggc    2820
agtgtgggtg cccaagcctt ggcactgatg ctggcaaaga acgtcatgct agaagaactc    2880
tgcctggagg agaaccatct ccaggatgaa ggtgtatgtt ctctcgcaga aggactgaag    2940
aaaaattcaa gtttgaaaat cctgaagttg tccaataact gcatcaccta cctaggggca    3000
gaagccctcc tgcaggccct tgaaaggaat gacaccatcc tggaagtctg gctccgaggg    3060
aacactttct ctctagagga ggttgacaag ctcggctgca gggacaccag actcttgctt    3120
tga                                                                  3123
```

<210> SEQ ID NO 59
<211> LENGTH: 1040
<212> TYPE: PRT
<213> ORGANISM: Homo sapiens

<400> SEQUENCE: 59

```
Met Gly Glu Glu Gly Ser Ala Ser His Asp Glu Glu Glu Arg Ala
1               5                   10                  15

Ser Val Leu Leu Gly His Ser Pro Gly Cys Glu Met Cys Ser Gln Glu
                20                  25                  30

Ala Phe Gln Ala Gln Arg Ser Gln Leu Val Glu Leu Leu Val Ser Gly
            35                  40                  45

Ser Leu Glu Gly Phe Glu Ser Val Leu Asp Trp Leu Leu Ser Trp Glu
        50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160
```

-continued

```
Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
        195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Ser Pro Gln Lys Ser
            260                 265                 270

Pro Ala Thr Leu Gly Leu Glu Glu Leu Phe Ser Thr Pro Gly His Leu
        275                 280                 285

Asn Asp Asp Ala Asp Thr Val Leu Val Val Gly Glu Ala Gly Ser Gly
    290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
        355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
        435                 440                 445

Glu Gln Gly Ile Glu Leu Tyr Leu Arg Lys His His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
        515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
545                 550                 555                 560

Cys Cys Tyr Val Phe Ser Ala Gln Gln Leu Gln Ala Ala Gln Val Ser
                565                 570                 575

Pro Asp Asp Ile Ser Leu Gly Phe Leu Val Arg Ala Lys Gly Val Val
```

-continued

```
            580                 585                 590
Pro Gly Ser Thr Ala Pro Leu Glu Phe Leu His Ile Thr Phe Gln Cys
            595                 600                 605

Phe Phe Ala Ala Phe Tyr Leu Ala Leu Ser Ala Asp Val Pro Pro Ala
    610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                645                 650                 655

Ser Ser Val Ala Ala Leu Leu Gln Lys Ala Glu Pro His Asn Leu Gln
            660                 665                 670

Ile Thr Ala Ala Phe Leu Ala Gly Leu Leu Ser Arg Glu His Trp Gly
        675                 680                 685

Leu Leu Ala Glu Cys Gln Thr Ser Glu Lys Ala Leu Leu Trp Arg Gln
    690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
                725                 730                 735

Pro Gly Phe Ile Trp Leu Ile Arg Ser Leu Tyr Glu Met Gln Glu Glu
            740                 745                 750

Arg Leu Ala Arg Lys Ala Ala Arg Gly Leu Asn Val Gly His Leu Lys
        755                 760                 765

Leu Thr Phe Cys Ser Val Gly Pro Thr Glu Cys Ala Ala Leu Ala Phe
    770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
            820                 825                 830

Cys Lys Leu Ile Glu Cys Ala Leu His Cys Glu Gln Leu Gln Lys Leu
        835                 840                 845

Ala Leu Phe Asn Asn Lys Leu Thr Asp Gly Cys Ala His Ser Met Ala
    850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
        915                 920                 925

Leu Arg Trp Leu Ser Leu Val Gly Asn Asn Ile Gly Ser Val Gly Ala
    930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
            980                 985                 990

Asn Cys Ile Thr Tyr Leu Gly Ala  Glu Ala Leu Leu Gln  Ala Leu Glu
        995                 1000                1005
```

```
Arg Asn Asp Thr Ile Leu Glu Val Trp Leu Arg Gly Asn Thr Phe
    1010             1015                 1020

Ser Leu Glu Glu Val Asp Lys Leu Gly Cys Arg Asp Thr Arg Leu
    1025             1030                 1035

Leu Leu
    1040

<210> SEQ ID NO 60
<211> LENGTH: 3123
<212> TYPE: DNA
<213> ORGANISM: Homo sapiens

<400> SEQUENCE: 60
```

| | | | | | |
|---|---|---|---|---|---|
| atgggggaag | agggtggttc | agcctctcac | gatgaggagg | aaagagcaag | tgtcctcctc | 60 |
| ggacattctc | cgggttgtga | aatgtgctcg | caggaggctt | ttcaggcaca | gaggagccag | 120 |
| ctggtcgagc | tgctggtctc | agggtccctg | gaaggcttcg | agagtgtcct | ggactggctg | 180 |
| ctgtcctggg | aggtcctctc | ctgggaggac | tacgagggct | tccacctcct | gggccagcct | 240 |
| ctctcccact | tggccaggcg | ccttctggac | accgtctgga | taagggtac | ttgggcctgt | 300 |
| cagaagctca | tcgcggctgc | ccaagaagcc | caggccgaca | gccagtcccc | caagctgcat | 360 |
| ggctgctggg | accccactc | gctccaccca | gcccgagacc | tgcagagtca | ccggccagcc | 420 |
| attgtcagga | ggctccacag | ccatgtggag | aacatgctgg | acctggcatg | ggagcggggt | 480 |
| ttcgtcagcc | agtatgaatg | tgatgaaatc | aggttgccga | tcttcacacc | gtcccagagg | 540 |
| gcaagaaggc | tgcttgatct | tgccacggtg | aaagcgaatg | gattggctgc | cttccttcta | 600 |
| caacatgttc | aggaattacc | agtcccattg | gccctgcctt | tggaagctgc | acatgcaag | 660 |
| aagtatatgg | ccaagctgag | gaccacggtg | tctgctcagt | ctcgcttcct | cagtacctat | 720 |
| gatggagcag | agacgctctg | cctggaggac | atatacacag | agaatgtcct | ggaggtctgg | 780 |
| gcagatgtgg | gcatggctgg | atccccgcag | aagagcccag | ccaccctggg | cctggaggag | 840 |
| ctcttcagca | cccctggcca | cctcaatgac | gatgcggaca | ctgtgctggt | ggtgggtgag | 900 |
| gcgggcagtg | gcaagagcac | gctcctgcag | cggctgcact | tgctgtgggc | tgcagggcaa | 960 |
| gacttccagg | aatttctctt | tgtcttccca | ttcagctgcc | ggcagctgca | gtgcatggcc | 1020 |
| aaaccactct | ctgtgcggac | tctactcttt | gagcactgct | gttggcctga | tgttggtcaa | 1080 |
| gaagacatct | tccagttact | ccttgaccac | cctgaccgtg | tcctgttaac | ctttgatggc | 1140 |
| tttgacagt | tcaagttcag | gttcacggat | cgtgaacgcc | actgctcccc | gaccgacccc | 1200 |
| acctctgtcc | agaccctgct | cttcaacctt | ctgcagggca | acctgctgaa | gaatgcccgc | 1260 |
| aaggtggtga | ccagccgtcc | ggccgctgtg | tcggcgttcc | tcaggaagta | catccgcacc | 1320 |
| gagttcaacc | tcaagggctt | ctctgaacag | ggcatcgagc | tgtacctgag | gaagcgccat | 1380 |
| catgagcccg | ggtggcgga | ccgcctcatc | cgcctgctcc | aagagacctc | agccctgcac | 1440 |
| ggtttgtgcc | acctgcctgt | cttctcatgg | atggtgtcca | atgccacca | ggaactgttg | 1500 |
| ctgcaggagg | gggggtcccc | aaagaccact | acagatatgt | acctgctgat | ctgcagcat | 1560 |
| tttctgctgc | atgccacccc | cccagactca | gcttcccaag | gtctgggacc | cagtcttctt | 1620 |
| cggggccgcc | tccccaccct | cctgcacctg | ggcagactgg | ctctgtgggg | cctgggcatg | 1680 |
| tgctgctacg | tgttctcagc | ccagcagctc | caggcagcac | aggtcagccc | tgatgacatt | 1740 |
| tctcttggct | tcctggtgcg | tgccaaaggt | gtcgtgccag | ggagtacggc | gcccctggaa | 1800 |
| ttccttcaca | tcactttcca | gtgcttcttt | gccgcgttct | acctggcact | cagtgctgat | 1860 |

-continued

```
gtgccaccag ctttgctcag cacctcttc aattgtggca ggccaggcaa ctcaccaatg    1920
gccaggctcc tgcccacgat gtgcatccag gcctcggagg gaaaggacag cagcgtggca    1980
gctttgctgc agaaggccga gccgcacaac cttcagatca cagcagcctt cctggcaggg    2040
ctgttgtccc gggagcactg gggcctgctg ctgagtgcc agacatctga gaaggccctg    2100
ctccggcgcc aggcctgtgc ccgctggtgt ctggcccgca gcctccgcaa gcacttccac    2160
tccatcccgc cagctgcacc gggtgaggcc aagagcgtgc atgccatgcc cgggttcatc    2220
tggctcatcc ggagcctgta cgagatgcag gaggagcggc tggctcggaa ggctgcacgt    2280
ggcctgaatg ttgggcacct caagttgaca ttttgcagtg tgggcccac tgagtgtgct    2340 gccctggcct ttgtgctgca gcacctccgg cggcccgtgg ccctgcagct ggactacaac    2400
tctgtgggtg acattggcgt ggagcagctg ctgccttgcc ttggtgtctg caaggctctg    2460
tatttgcgcg ataacaatat ctcagaccga ggcatctgca agctcattga atgtgctctt    2520
cactgcgagc aattgcagaa gttagctcta ttcaacaaca aattgactga cggctgtgca    2580
cactccatgg ctaagctcct tgcatgcagg cagaacttct tggcattgag ctggggaat    2640 aactacatca ctgccgcggg agcccaagtg ctggccgagg ggctccgagg caacacctcc    2700
ttgcagttcc tgggattctg cgcaacaga gtgggtgacg agggggccca ggccctggct    2760
gaagccttgg gtgatcacca gagcttgagg tggctcagcc tggtggggaa caacattggc    2820
agtgtgggtg cccaagcctt ggcactgatg ctggcaaaga acgtcatgct agaagaactc    2880
tgcctggagg agaaccatct ccaggatgaa ggtgtatgtt ctctcgcaga aggactgaag    2940
aaaaattcaa gtttgaaaat cctgaagttg tccataact gcatcaccta cctagggca    3000 gaagccctcc tgcaggccct tgaaaggaat gacaccatcc tggaagtctg gctccgaggg    3060
aacactttct ctctagagga ggttgacaag ctcggctgca gggacaccag actcttgctt    3120
tga                                                                3123
```

<210> SEQ ID NO 61
<211> LENGTH: 1040
<212> TYPE: PRT
<213> ORGANISM: Homo sapiens

<400> SEQUENCE: 61

```
Met Gly Glu Glu Gly Ser Ala Ser His Asp Glu Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140
```

```
Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
        195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Ser Pro Gln Lys Ser
                260                 265                 270

Pro Ala Thr Leu Gly Leu Glu Glu Leu Phe Ser Thr Pro Gly His Leu
            275                 280                 285

Asn Asp Asp Ala Asp Thr Val Leu Val Val Gly Glu Ala Gly Ser Gly
        290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
        355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
        435                 440                 445

Glu Gln Gly Ile Glu Leu Tyr Leu Arg Lys His His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
        515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
545                 550                 555                 560
```

-continued

```
Cys Cys Tyr Val Phe Ser Ala Gln Gln Leu Gln Ala Ala Gln Val Ser
            565                 570                 575

Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
            595                 600                 605

Phe Phe Ala Ala Phe Tyr Leu Ala Leu Ser Ala Asp Val Pro Pro Ala
            610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                    645                 650                 655

Ser Ser Val Ala Ala Leu Leu Gln Lys Ala Glu Pro His Asn Leu Gln
                    660                 665                 670

Ile Thr Ala Ala Phe Leu Ala Gly Leu Leu Ser Arg Glu His Trp Gly
                    675                 680                 685

Leu Leu Ala Glu Cys Gln Thr Ser Glu Lys Ala Leu Leu Arg Arg Gln
690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
                    725                 730                 735

Pro Gly Phe Ile Trp Leu Ile Arg Ser Leu Tyr Glu Met Gln Glu Glu
                    740                 745                 750

Arg Leu Ala Arg Lys Ala Ala Arg Gly Leu Asn Val Gly His Leu Lys
                    755                 760                 765

Leu Thr Phe Cys Ser Val Gly Pro Thr Glu Cys Ala Ala Leu Ala Phe
                    770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                    805                 810                 815

Cys Lys Ala Leu Tyr Leu Arg Asp Asn Asn Ile Ser Asp Arg Gly Ile
                    820                 825                 830

Cys Lys Leu Ile Glu Cys Ala Leu His Cys Glu Gln Leu Gln Lys Leu
                    835                 840                 845

Ala Leu Phe Asn Asn Lys Leu Thr Asp Gly Cys Ala His Ser Met Ala
850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                    885                 890                 895

Gly Asn Thr Ser Leu Gln Phe Leu Gly Phe Trp Arg Asn Arg Val Gly
                    900                 905                 910

Asp Glu Gly Ala Gln Ala Leu Ala Glu Ala Leu Gly Asp His Gln Ser
                    915                 920                 925

Leu Arg Trp Leu Ser Leu Val Gly Asn Asn Ile Gly Ser Val Gly Ala
                    930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                    965                 970                 975

Glu Gly Leu Lys Lys Asn Ser Ser Leu Lys Ile Leu Lys Leu Ser Asn
```

-continued

```
                    980             985             990
Asn Cys Ile Thr Tyr Leu Gly Ala  Glu Ala Leu Leu Gln  Ala Leu Glu
        995                 1000                1005

Arg Asn Asp Thr Ile Leu Glu  Val Trp Leu Arg Gly  Asn Thr Phe
       1010             1015             1020

Ser Leu Glu Glu Val Asp Lys  Leu Gly Cys Arg Asp  Thr Arg Leu
       1025             1030             1035

Leu Leu
   1040

<210> SEQ ID NO 62
<211> LENGTH: 20
<212> TYPE: DNA
<213> ORGANISM: Artificial
<220> FEATURE:
<223> OTHER INFORMATION: synthetic

<400> SEQUENCE: 62
gtcatccagc cagatttagg                                              20
```